(12) United States Patent
Faatz et al.

(10) Patent No.: US 11,319,351 B2
(45) Date of Patent: *May 3, 2022

(54) SOLUBLE AND IMMUNOREACTIVE FLAVIVIRAL NS1 POLYPEPTIDES COMPRISING THE WING DOMAIN

(71) Applicant: Roche Diagnostics Operations, Inc., Indianapolis, IN (US)

(72) Inventors: Elke Faatz, Huglfing (DE); Alexander Riedel, Munich (DE); Christian Scholz, Penzberg (DE); Peter Muench, Penzberg (DE); Gloria Tabares, Munich (DE); Mario Gloeck, Geretsried (DE); Silke Luebcke, Munich (DE); Juliane Benz, Weilheim (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 111 days.

This patent is subject to a terminal disclaimer.

(21) Appl. No.: 16/663,457

(22) Filed: Oct. 25, 2019

(65) Prior Publication Data

US 2020/0048313 A1    Feb. 13, 2020

Related U.S. Application Data

(63) Continuation of application No. PCT/EP2018/060330, filed on Apr. 23, 2018.

(30) Foreign Application Priority Data

Apr. 26, 2017    (EP) .................................... 17168197

(51) Int. Cl.
  *C07K 14/005*    (2006.01)
  *C07K 14/18*    (2006.01)
  *C12N 7/00*    (2006.01)
  *G01N 33/569*    (2006.01)

(52) U.S. Cl.
  CPC ........ *C07K 14/1825* (2013.01); *C07K 14/005* (2013.01); *C12N 7/00* (2013.01); *G01N 33/56983* (2013.01); *C07K 2319/33* (2013.01); *C07K 2319/35* (2013.01); *C12N 2770/24031* (2013.01); *C12N 2770/24122* (2013.01); *C12N 2770/24131* (2013.01); *C12N 2770/24151* (2013.01); *G01N 2333/185* (2013.01); *G01N 2469/20* (2013.01); *G01N 2800/26* (2013.01)

(58) Field of Classification Search
  CPC ............ C07K 14/1825; C07K 2319/35; C07K 14/005; C12N 2770/24122; G01N 2333/185

See application file for complete search history.

(56) References Cited

U.S. PATENT DOCUMENTS

2019/0031722 A1*    1/2019    Bremel .................. A61K 39/12

FOREIGN PATENT DOCUMENTS

| WO | 1998/013496 A1 | 4/1998 |
|---|---|---|
| WO | 2003/000877 A2 | 1/2003 |
| WO | 2014/054990 A1 | 4/2014 |
| WO | 2017/144173 A1 | 8/2017 |

OTHER PUBLICATIONS

Akey, David L. et al., Flavivirus NS1 crystal structures reveal a surface for membrane association and regions of interaction with the immune system, Science, 2014, pp. 881-885, vol. 343, No. 6173.
Akey, David L. et al., Structure-guided insights on the role of NS1 in flavivirus infection, Bioessays, 2015, pp. 489-494, vol. 37.
Brown, W. Clay et al., Extended surface for membrane association in Zika virus NS1 structure, Nature Structural & Molecular Biology, 2016, pp. 865-868, vol. 23, No. 9.
Collins, Matthew H. and Metz, Stefan W., Progress and Works in Progress: Update on Flavivirus Vaccine Development, Clinical Therapeutics, 2017, pp. 1519-1536, vol. 39, No. 8.
Cox, Bryan D. et al., Predicting Zika virus structural biology: Challenges and opportunities for intervention, Antiviral Chemistry and Chemotherapy, 2015, pp. 118-126, vol. 24, No. 3-4.
Hilgenfeld, Rolf, Zika virus NS1, a pathogenicity factor with many faces, EMBO Journal, 2016, pp. 2631-2633, vol. 35, No. 4.
Huzly, D. et al., High specificity of a novel Zika virus ELISA in European patients after exposure to different flaviviruses, Euro Surveillance, 2016, 4 pp., vol. 21, No. 16.
International Search Report dated Jun. 26, 2018, in Application No. PCT/EP2018/060330, 5 pp.
Olliaro, Piero et al., Improved tools and strategies for the prevention and control of arboviral diseases: A research-to-policy forum, PLoS Neglected Tropical Diseases, 2018, 13 pp., vol. 2, No. 2, e0005967.
Panning, Marcus, Zika Virus Serology: More Diagnostic Targets, more Reliable Answers?, EBioMedicine, 2017, pp. 12-13, vol. 16.
Rastogi, Meghana et al., Flavivirus NS1: a multifaced enigmatic viral protein, Virology Journal, 2016, 10 pp., vol. 13, No. 131.

(Continued)

*Primary Examiner* — Jeffrey S Parkin
(74) *Attorney, Agent, or Firm* — Stinson LLP

(57) ABSTRACT

The disclosure relates to a polypeptide suitable for detecting antibodies against a flavivirus in an isolated biological sample having a flavivirus NS1 wing domain specific amino acid sequence, wherein no amino acid sequences from the NS1 ß-ladder domain of said flavivirus are present in the polypeptide. In an embodiment, the flavivirus is selected from Zika virus (ZIKV), West-Nile virus (WNV), Dengue virus types 1-4 (DENV1-4), tick-borne encephalitis virus (TBEV), yellow fever virus (YFV) and Japanese encephalitis virus (JEV). Also disclosed is a method for producing said flaviviral NS1 wing domain specific polypeptides, a method for detecting antibodies specific for a first flavivirus species, the use of said flaviviral NS1 wing domain specific polypeptides for detecting antibodies as well as a reagent kit for detecting said flavivirus antibodies that has a flavivirus NS1 wing domain polypeptide.

10 Claims, No Drawings

Specification includes a Sequence Listing.

(56) References Cited

OTHER PUBLICATIONS

Scaturro, Pietro et al., Dengue Virus Non-structural Protein 1 Modulates Infectious Particle Production via Interaction with the Structural Proteins, PLOS Pathogens, 2015, e100527, 32 pp., vol. 11, No. 11.
Scholz, Christian et al., Functional Solubilization of Aggregation-prone HIV Envelope Proteins by Covalent Fusion with Chaperone Modules, Journal of Molecular Biology, 2005, pp. 1229-1241, vol. 345.
Song, Hao et al., Zika virus NS1 structure reveals diversity of electrostatic surfaces among flaviviruses, Nature Structural & Molecular Biology, 2016, pp. 456-459, vol. 23, No. 5.
Steinhagen, K et al., Serodiagnosis of Zika virus (ZIKV) infections by a novel NS1-based ELISA devoid of cross-reactivity with dengue virus antibodies: a multicohort study of assay performance, 2015 to 2016, Euro Surveillance, 2016, 16 pp., vol. 21, No. 50.
Stettler, Karin et al., Specificity, cross-reactivity and function of antibodies elicited by Zika virus infection, Science, 2016, pp. 823-826, vol. 353, Issue 6301.
Wong, Susan J. et al., A Multiplex Microsphere Immunoassay for Zika Virus Diagnosis, EBioMedicine, 2017, pp. 136-140, vol. 16.
Xu, Xiaoying et al., Contribution of interwined loop to membrane association revealed by Zika virus full-length NS1 structure, The EMBO journal, 2016, pp. 2170-2178, vol. 35, No. 20.

\* cited by examiner

SOLUBLE AND IMMUNOREACTIVE FLAVIVIRAL NS1 POLYPEPTIDES COMPRISING THE WING DOMAIN

CROSS-REFERENCE TO RELATED APPLICATIONS

This application is a continuation of International Application No. PCT/EP2018/060330 filed Apr. 23, 2018, which claims priority to European Application No. 17168197.6 filed Apr. 26, 2017, the disclosures of which are hereby incorporated by reference in their entirety.

BACKGROUND OF THE INVENTION

According to the World Health Organization tropical diseases transferred by flaviviruses such as Zika virus, Dengue virus and others, continue to spread worldwide (Olliaro et al. PLOS Neglected Tropical Diseases Feb. 1, 2018, 1-13). Flavivirus is a genus of the family Flaviviridae, including e.g. Zika virus, Dengue virus, West Nile virus, tick-borne encephalitis virus, yellow fever virus and Japanese encephalitis virus. Flaviviruses are transmitted by arthropod vectors such as insects, mosquitos or ticks, e.g. the Egyptian and the Asian mosquito strains *Aedes aegypti* and *Aedes albopictus*, and are therefore classified as arboviruses (arthropod-borne virus).

Infection of an otherwise healthy person with a flavivirus may lead to mild symptoms like fever, fatigue, rash and body aches. However, depending on the person's general health and immune status the infection may also lead to severe and sometimes even lethal sequelae. While the mild symptoms share some similarity the serious complications are very different, depending on the respective flavivirus.

Zika virus can be transmitted from an expectant mother to her fetus in utero and is suspected to cause severe brain malformations and defects such as microcephaly in the unborn child. Microcephaly (derived from Greek for "small head") is a condition in which a baby's brain does not develop properly, and thus its head has a smaller size than normal. Infection in adults may lead to the so-called Guillan-Barré syndrome (muscle weakness caused by the immune system which attacks the peripheral nervous system).

An infection with Dengue virus may lead to medical complications like hemorrhagic fever and death, in particular if the infection is not recognized timely followed by immediate supportive treatment. To date, four types of Dengue virus are known (Dengue virus 1-4) and an infection with one type of Dengue does not confer immunity to the remaining types. Usually, secondary infections with Dengue hit harder than the first one and vaccinated persons, especially children, often face severe medical complications upon a Dengue infection.

Infection with West Nile virus may affect the central nervous system leading to encephalitis (inflammation of the brain) or meningitis (inflammation of the membranes that surround the brain and spinal cord) and may also cause a long lasting paralysis that is similar to polio.

Vaccines for several flavivirus infections are available, e.g. for Dengue, West Nile virus, tick-borne encephalitis virus, yellow fever virus and Japanese encephalitis virus, but not for Zika virus. However, vaccination is not always effective or may lead to severe complications as e.g. for secondary Dengue infections (for review see Collins and Metz, Clin Therap, 2017 Vol. 39, 8 p. 1519-1536). Efficacious medical treatment after infection is lacking. In order to receive timely supportive treatment it is crucial to know if a patient has been infected with a flavivirus and in particular with what specific kind of flavivirus. Therefore highly sensitive and specific serological diagnostics need to be developed in order to reliably confirm or rule out an infection of a patient with a flavivirus, in particular with any of Zika, Dengue or West Nile virus. In particular, highly specific immunoassays are utterly needed in regions with high prevalence of multiple flaviviral infections. As a matter of course, it is a daunting task to reliably diagnose, e.g., a recent Zika infection in an individual that has undergone other flaviviral infections such as Dengue or Yellow fever in the past and whose serum is characterized by polyclonal antibodies against the main immunogens of Dengue and Yellow fever virus.

Since 2016 a couple of ELISA-based immunoassays detecting antibodies against the Zika virus NS1 antigen are commercially available (e.g. Huzly et al., Euro Surveill. 2016; 21 (16) pii=30203, 1-4). However, these assays are suspected to cross-react with antibodies that have originally been raised against related viruses such as Dengue virus and other arboviruses that belong to the family of flaviviruses like West Nile virus, yellow fever virus, tick-borne encephalitis virus (FSME) or Japanese encephalitis virus. This cross-reactivity would lead to false positive results and erroneous interpretation of a patient's immune status and seems to be due to the structural and sequence homologies of Zika NS1 (non-structural antigen 1) with its counterparts in other flaviviruses such as West Nile and Dengue viruses (Hilgenfeld 27 Oct. 2016, Embo J. 1-3). It is conceivable that the incidence and prevalence data that have been reported for the Zika epidemic in Brazil in 2015/2016, have suffered the flaw of an exaggeration bias due to the limited specificity of the immunoassays that have been used at the time. In order to evaluate prevalence and incidence data and to assess the objective risk of an emerging epidemic, clear-cut diagnostics are an indispensable prerequisite. Serologic assays with poor specificity would overemphasize the extent of an epidemic and therefore lead to panic-driven decisions not only by the authorities, but also by unsettled and frightened individuals. For instance, it has been reported that the number of abortions in Brazil has significantly increased in the wake of the medial reporting on the true or ostensible Zika epidemic.

Dengue virus and West Nile virus IgG and IgM immunoassays based on the ELISA principle are commercially available. However, the known immunoassays evidently use the full length NS1 antigen that on the one hand is highly immunoreactive (i.e., it is highly reactive as an immunogen in the flavivirus infection, and it is well-suited as an antigen for the detection of the immunoglobulins that have been produced in the course of the immune response) but on the other hand is prone to cross-react with antibodies originally produced against other flaviviruses.

The crystal structure of full-length, glycosylated NS1 from West Nile and Dengue virus has been solved at high resolution and reveals distinct domains and a rather complex protein topology (Akey et al., Science (2014; 343 (6173): 881-885). Recently, the crystal structure of a C-terminal fragment (amino acid residues 172-352) of the Zika virus nonstructural protein 1 (NS1) has been published, revealing a head-to-head dimer and confirming the oligomeric character of NS1 (Song et al. Nature Struct. Mol. Biol. 2016 (23) 5, 456-459). In addition, the complete three-dimensional structure of full-length Zika virus NS1 has been published by Brown et al. Nature Struct. Mol. Biol. 2016 (23) 9, 865-868, describing the NS1 structure in further detail. Thus, NS1 turns out to be a very intricate and complex protein due to its oligomeric state, its glycosylation pattern and its abundance in cysteine residues. Yet, publications on dedicated flaviviral antigens, in particular for the diagnosis of Zika, Dengue and West Nile virus are scarce, and reliable information on linear or conformational B-cell epitopes that are unique in the individual flavivirus antigens and would allow for a clear-cut discrimination between the envisaged virus and related flaviviruses has not been available so far.

International patent applications WO2017/144173 and WO2017/144173 describe variants of the full length Zika NS1 antigen of 352 amino acids, listing several essential epitopes, wherein a ß-ladder domain epitope (positions 322 to 326) in the C-terminal part of the NS1 antigen is regarded as essential for reactivity.

The problem underlying the invention therefore is the limited specificity of the hitherto available immunoassays detecting antibodies against a specific flavivirus, in particular Zika virus, Dengue virus and West Nile virus. The problem is solved by the current invention as specified in the claims.

SUMMARY OF THE INVENTION

The invention relates to a polypeptide suitable for detecting antibodies against a flavivirus in an isolated biological sample comprising a flavivirus NS1 wing domain specific amino acid sequence, wherein no amino acid sequences from the NS1 ß-ladder domain of said flavivirus are present in said polypeptide. In an embodiment no further amino acid sequences of said flavivirus are present in said polypeptide. In an embodiment, said flavivirus is selected from the group consisting of Zika virus (ZIKV), West-Nile virus (WNV), Dengue virus types 1-4 (DENV1-4), tick-borne encephalitis virus (TBEV), yellow fever virus (YFV) and Japanese encephalitis virus (JEV). The invention also relates to a method for producing said flaviviral NS1 wing domain specific polypeptides, a method for detecting antibodies specific for a flavivirus, in particular for detecting a first flavivirus species in the presence of antibodies against at least a second or multiple flavivirus species, the use of said flaviviral NS1 wing domain specific polypeptides for detecting antibodies as well as a reagent kit for detecting said flavivirus antibodies that comprises a flavivirus NS1 wing domain polypeptide.

Legend to the Disclosed Amino Acid Sequences

The mature NS1 protein comprises 352 amino acid residues (NS1, 1-352). Within the NS1 protein, the wing domain comprises 151 amino acid residues and spans the NS1 amino acid region 30-180. Thus, the wing domain positions (1-151) easily translate into the NS1 numbering by adding 29 amino acid positions. Vice versa, the NS1 amino acid positions easily translate into wing domain numbering by subtracting as many as 29 amino acid positions; aa 1 (wing)=aa 30 (NS1), aa 2 (wing)=aa 31 (NS1), aa 3 (wing)=aa 32 (NS1) and so forth. In an analogous way the ß-ladder domain positions (1-162) easily translate into the NS1 numbering by adding 190 amino acid positions as the NS1 positions 191-352 correspond to the ß-ladder domain.

```
SEQ ID NO: 1 Zika virus NS1 wing domain aa 30-180 with position 179 X = A or
S or C
DRYKYHPDSP RRLAAAVKQA WEEGICGISS VSRMENIMWK SVEGELNAIL EENGVQLTVV VGSVKNPMWR

GPQRLPVPVN ELPHGWKAWG KSYFVRAAKT NNSFVVDGDT LKECPLKHRA WNSFLVEDHG FGVFHTSVWL

KVREDYSLEX D,

SEQ ID NO: 2 Zika virus NS1 wing domain aa 30-180 with C55, C143, C179A
DRYKYHPDSP RRLAAAVKQA WEEGICGISS VSRMENIMWK SVEGELNAIL EENGVQLTVV VGSVKNPMWR

GPQRLPVPVN ELPHGWKAWG KSYFVRAAKT NNSFVVDGDT LKECPLKHRA WNSFLVEDHG FGVFHTSVWL

KVREDYSLEA D,

SEQ ID NO: 3 Zika virus NS1 full length aa 1-352; this sequence is also
published as strain MR 766, UniProt ID W8Q7Q3; the corresponding
numbering within the full length Zika precursor polyprotein is aa
795-1146
DVGCSVDFSK RETRCGTGVF IYNDVEAWRD RYKYHPDSPR RLAAAVKQAW EEGICGISSV

SRMENIMWKS VEGELNAILE ENGVQLTVVV GSVKNPMWRG PQRLPVPVNG LPHGWKAWGK

SYFVRAAKTN NSFVVDGDTL KECPLKHRAW NSFLVEDHGF GVFHTSVWLK VREDYSLECD

PAVIGTAVKG REAAHSDLGY WIESEKNDTW RLKRAHLIEM KTCEWPKSHT LWTDGVEESD

LIIPKSLAGP LSHHNTREGY RTQVKGPWHS EELEIRFEEC PGTKVHVEET CGTRGPSLRS

TTASGRVIEE WCCRECTMPP LSFRAKDGCW YGMEIRPRKE PESNLVRSMV TA,

SEQ ID NO: 4 Zika virus NS1 β-ladder domain aa 191-352
REAAHSDLGY WIESEKNDTW RLKRAHLIEM KTCEWPKSHT LWTDGVEESD LIIPKSLAGP

LSHHNTREGY RTQVKGPWHS EELEIRFEEC PGTKVHVEET CGTRGPSLRS TTASGRVIEE

WCCRECTMPP LSFRAKDGCW YGMEIRPRKE PESNLVRSMV TA,
```

SEQ ID NO: 5 Tick-borne encephalitis (FSME) virus NS1 wing domain
aa 30-180 according to UniProt ID P14336; European subtype strain
Neudoerfl; X = A or C or S
DNYAYYPETP GALASAIKET FEEGSCGVVP QNRLEMAMWR SSVTELNLAL AEGEANLTVV

VDKFDPTDYR GGVPGLLKKG KDIKVSWKSW GHSMIWSIPE APRRFMVGTE GQSECPLERR

KTGVFTVAEF GVGLRTKVFL DFRQEPTHEX D,

SEQ ID NO: 6: Tick-borne encephalitis (FSME) virus NS1 full length
aa 1-352; this sequence is also published as European subtype strain
Neudoerfl, UniProt ID P14336; the corresponding numbering within the
full length precursor is aa 777-1128.
DVGCAVDTER MELRCGEGLV VWREVSEWYD NYAYYPETPG ALASAIKETF EEGSCGVVPQ

NRLEMAMWRS SVTELNLALA EGEANLTVVV DKFDPTDYRG GVPGLLKKGK DIKVSWKSWG

HSMIWSIPEA PRRFMVGTEG QSECPLERRK TGVFTVAEFG VGLRTKVFLD FRQEPTHECD

TGVMGAAVKN GMAIHTDQSL WMRSMKNDTG TYIVELLVTD LRNCSWPASH TIDNADVVDS

ELFLPASLAG PRSWYNRIPG YSEQVKGPWK YTPIRVIREE CPGTTVTINA KCDKRGASVR

STTESGKVIP EWCCRACTMP PVTFRTGTDC WYAMEIRPVH DQGGLVRSMV VA

SEQ ID NO: 7 Dengue virus type 1 NS1 wing domain aa 30-180; X = A or C or S
EQYKFQADSP KRLSAAIGKA WEEGVCGIRS ATRLENIMWK QISNELNHIL LENDMKFTVV VGDVAGILAQ

GKKMIRPQPM EHKYSWKSWG KAKIIGADVQ NTTFIIDGPN TPECPDDQRA WNIWEVEDYG FGIFTTNIWL

KLRDSYTQVX D,

SEQ ID NO: 8 Dengue virus type 1 NS1 full length aa 1-352; this sequence is
also published under UniProt ID W8FUV0; the corresponding numbering within
the full length precursor is aa 776-1127.
DSGCVINWKG RELKCGSGIF VTNEVHTWTE QYKFQADSPK RLSAAIGKAW EEGVCGIRSA

TRLENTMWKQ ISNELNHILL ENGMKFTVVV GEVNGILAQG KKMIRPQPME HKYSWKSWGK

AKVIGADVQN TTFIIDGPNT PECPDDQRAW NIWEVEDYGF GIFTTNIWLK LRDSYTQVCD

HRLMSAAIKD SKAVHADMGY WIESEKNETW KLARASFIEV KTCIWPKSHT LWSNGVLESE

MIIPKIYGGP ISQHNYRPGY FTQTAGPWHL GKLELDFELC EGTTVVVDEH CGNRGPSLRT

TTVTGKIIHE WCCRSCTLPP LRFKGEDGCW YGMEIRPVKE KEENLVKSMV SA,

SEQ ID NO: 9 Dengue virus type 2 NS1 wing domain aa 30-180; X = A or C or S
EQYKFQPESP SKLASAIQKA HEEGICGIRS VTRLENLMWK QITPELNHIL SENEVKLTIM TGDIKGIMQA

GKRSLRPQPT ELKYSWKTWG KAKMLSTESH NQTFLIDGPE TAECPNTNRA WNSLEVEDYG FGVFTTNIWL

KLKEKQDVFX D,

SEQ ID NO: 10 Dengue virus type 2 NS1 full length aa 1-352; this
sequence is also published as strain Thailand/16881/1984 according
to UniProt ID P29990, the corresponding numbering within the full
length precursor is aa 776-1127.
DSGCVVSWKN KELKCGSGIF ITDNVHTWTE QYKFQPESPS KLASAIQKAH EEGICGIRSV

TRLENLMWKQ ITPELNHILS ENEVKLTIMT GDIKGIMQAG KRSLRPQPTE LKYSWKTWGK

AKMLSTESHN QTFLIDGPET AECPNTNRAW NSLEVEDYGF GVFTTNIWLK LKEKQDVFCD

SKLMSAAIKD NRAVHADMGY WIESALNDTW KIEKASFIEV KNCHWPKSHT LWSNGVLESE

MIIPKNLAGP VSQHNYRPGY HTQITGPWHL GKLEMDFDFC DGTTVVVTED CGNRGPSLRT

TTASGKLITE WCCRSCTLPP LRYRGEDGCW YGMEIRPLKE KEENLVNSLV TA,

SEQ ID NO: 11 Dengue virus type 3 NS1 wing domain aa 30-180; X = A or C or S)
EQYKFQADSP KRLATAIAGA WENGVCGIRS TTRMENLLWK QIANELNYIL WENNIKLTVV VGDIIGILEQ

GKRTLTPQPM ELKYSWKTWG KAKIVTAETQ NSSFIIDGPN TPECPNASRA WNVWEVEDYG FGVFTTNIWL

KLREMYSQLX D,

-continued

SEQ ID NO: 12 Dengue virus type 3 NS1 full length aa 1-352;
this sequence is also published under UniProt ID W8FRG8; the corresponding numbering within the full length precursor is aa 774-1125.

DMGCVINWKG KELKCGSGIF VTNEVHTWTE QYKFQADSPK RLATAIAGAW ENGVCGIRST

TRMENLLWRQ IANELNYILW ENNIKLTVVV GDIIGILEQG KRTLTPQPME LKYSWKTWGK

AKIVTAETQN SSFIIDGPNT PECPNASRAW NVWEVEDYGF GVETTNIWLK LREMYSQLCD

HRLMSAAVKD ERAVHADMGY WIESQKNGSW KLEKASLIEV KTCTWPKSHT LWSNGVLESD

MIIPKSLAGP ISQHNYRPGY HTQTAGPWHL GKLELDFNYC EGTTVVITEN CGTRGPSLRT

TTVSGKLIHE WCCRSCTLPP LRYMGEDGCW YGMEIRPINE KEENMVKSLV SA,

SEQ ID NO: 13 Dengue virus type 4 NS1 wing domain aa 30-180; X = A or C or S)

EQYKFQPESP ARLASAILNA HKDUVCGIRS TTRLENIMWK QITNELNYVL WEGGHDLTVV AGDVKGVLTK

GKRALTPPVN DLKYSWKTWG KAKIFTPEAR NSTFLIDGPD TSECPNERRA WNFFEVEDYG FGMFTTNIWM

KFREGSSEVX D,

SEQ ID NO: 14 Dengue virus type 4 NS1 full length aa 1-352; this sequence is also published as strain Philippines/H241/1956, UniProt ID Q58HT7; the corresponding numbering within the full length precursor is aa 775-1126.

DTGCAVSWSG KELKCGSGIF VIDNVHTWTE QYKFQPESPA RLASAILNAH EDGVCGIRST

TRLENIMWKQ ITNELNYVLW EGGHDLTVVA GDVKGVLSKG KRALAPPVND LKYSWKTWGK

AKIFTPEAKN STFLIDGPDT SECPNERRAW NFLEVEDYGF GMFTTNIWMK FREGSSEVCD

HRLMSAAIKD QKAVHADMGY WIESSKNQTW QIEKASLIEV KTCLWPKTHT LWSNGVLESQ

MLIPKAYAGP FSQHNTPQGY ATQTVGPWHL GKLEIDFGEC PGTTVTIQED CDHRGPSLRT

TTASGKLVTQ WCCRSCTMPP LRFLGEDGCW YGMEIRPLSE KEENMVKSQV SA,

SEQ ID NO: 15 West-Nile virus NS1 wing domain aa 30-180; X = A or C or S

DRYKFYPETP QGLAKIIQKA HAEGVCGLRS VSRLEHQMWE AIKDELNTLL KENGVDLSVV VEKQNGMYKA

APKRLAATTE KLEMGWKAWG KSIIFAPELA NNTFVIDGPE TEECPTANRA WNSMEVEDFG FGLTSTRMFL

RIRETNTTEX D,

SEQ ID NO: 16 West-Nile virus NS1 full length aa 1-352; this sequence is also published under UniProt ID P06935; the corresponding numbering within the full length precursor is aa 788-1139.

DTGCAIDIGR QELRCGSGVF IHNDVEAWMD RYKFYPETPQ GLAKIIQKAH AEGVCGLRSV

SRLEHQMWEA IKDELNTLLK ENGVDLSVVV EKQNGMYKAA PKRLAATTEK LEMGWKAWGK

SIIFAPELAN NTFVIDGPET EECPTANRAW NSMEVEDFGF GLTSTRMFLR IRETNTTECD

SKIIGTAVKN NMAVHSDLSY WIESGLNDTW KLERAVLGEV KSCTWPETHT LWGDGVLESD

LIIPITLAGP RSNHNRRPGY KTQNQGPWDE GRVEIDFDYC PGTTVTISDS CEHRGPAART

TTESGKLITD WCCRSCTLPP LRFQIENGCW YGMEIRPTRH DEKTLVQSRV NA,

SEQ ID NO: 17 Yellow fever virus NS1 wing domain aa 30-180; X = A or C or S

NKYSYYPEDP VKLASIVKAS FEEGKCGLNS VDSLEHEMWR SRADEINAIF EENEVDISVV

VQDPKNVYQR GTHPFSRIRD GLQYGWKTWG KNLVFSPGRK NGSFIIDGKS RKECPFSNRV

WNSFQIEEFG TGVFTTRVYM DAVFEYTIDX D,

SEQ ID NO: 18 Yellow fever virus NS1 full length aa 1-352; this sequence is also published as strain 17D vaccine, UniProt ID P03314; the corresponding numbering within the full length precursor is aa 779-1130.

DQGCAINFGK RELKCGDGIF IFRDSDDWLN KYSYYPEDPV KLASIVKASF EEGKCGLNSV

DSLEHEMWRS RADEINAIFE ENEVDISVVV QDPKNVYQRG THPFSRIRDG LQYGWKTWGK

NLVFSPGRKN GSFIIDGKSR KECPFSNRVW NSFQIEEFGT GVFTTRVYMD AVFEYTIDCD

GSILGAAVNG KKSAHGSPTF WMGSHEVNGT WMIHTLEALD YKECEWPLTH TIGTSVEESE

```
MFMPRSIGGP VSSHNHIPGY KVQTNGPWMQ VPLEVKREAC PGTSVIIDGN CDGRGKSTRS

TTDSGKVIPE WCCRSCTMPP VSFHGSDGCW YPMEIRPRKT HESHLVRSWV TA,

SEQ ID NO: 19 Japanese encephalitis virus NS1 wing domain aa 30-180;
X = A or C or S
DRYKYLPETP RSLAKIVHKA HKEGVCGVRS VTRLEHQMWE AVRDELNVLL KENAVDLSVV

VNKPVGRYRS APKRLSMTQE KFEMGWKAWG KSILFAPELA NSTFVVDGPE TKECPDEHRA

WNSMQIEDFG FGITSTRYWL KIREESTDEX D,

SEQ ID NO: 20 Japanese encephalitis virus NS1 full length aa 1-352;
this sequence is also published under UniProt ID Q9YJ16; the
corresponding numbering within the full length precursor is aa 795-
1146.
DITCAIDITR KEMRCGSGIF VHNDVEAWVD RYKYLPETPR SLAKIVHKAH KEGVCGVRSV

TRLEHQMWEA VRDELNVLLK ENAVDLSVVV NKPVGRYRSA PKRLSMTQEK FEMGWKAWGK

SILFAPELAN STFVVDGPET KECPDEHRAW NSMQIEDFGF GITSTRVWLK IREESTDECD

GAIIGTAVKG HVAVHSDLSY WIESRYNDTW KLERAVFGEV KSGTWPETHT LWGDGVEFSE

LIIPHTIAGP KSKHNRREGY KTQNQGPWDE NGIVLDFDYC PGTKVTITED CGKRGPSVRT

TIDSGKLITD WCCRSCSLPP LRFRTENGCW YGMEIRPVRH DEATLVRSQV DA,

SEQ ID NO: 21 Fusion protein of tandem E. coli SlyD with Zika
virus NS1 wing domain aa 30-180
MKVAKDLVVS LAYQVRTEDG VLVDESPVSA PLDYLHGHGS LISGLETALE GHEVGDKFDV

AVGANDAYGQ YDENLVQRVP KDVFMGVDEL QVGMRFLAET DQGPVPVEIT AVEDDHVVVD

GNHMLAGQNL KFNVEVVAIR EATEEELAHG HVHGAHDHHH DHDHDGGGSG GGSGGGSGGG

SGGGSGGGKV AKDLVVSLAY QVRTEDGVLV DESPVSAPLD YLHGHGSLIS GLETALEGHE

VGDKFDVAVG ANDAYGQYDE NLVQRVPKDV FMGVDELQVG MRFLAETDQG PVPVEITAVE

DDHVVVDGNH MLAGQNLKFN VEVVAIREAT EEELAHGHVH GAHDHHHDHD HDGGGSGGGS

GGGSGGGSGG GSGGGDRYKY HPDSPRRLAA AVKQAWEEGI CGISSVSRME NIMWKSVEGE

LNAILEENGV QLTVVVGSVK NPMWRGPQRL PVPVNELPHG WKAWGKSYFV RAAKTNNSFV

VDGDTLKECP LKHRAWNSFL VEDHGFGVFH TSVWLKVRED YSLEADLEHH HHHH,

SEQ ID NO: 22 Fusion protein of tandem E. coli SlyD with Zika virus
NS1 β-ladder domain (aa 191-352, strain Mr 766)
MKVAKDLVVS LAYQVRTEDG VLVDESPVSA PLDYLHGHGS LISGLETALE GHEVGDKFDV

AVGANDAYGQ YDENLVQRVP KDVFMGVDEL QVGMRFLAET DQGPVPVEIT AVEDDHVVVD

GNHMLAGQNL KFNVEVVAIR EATEEELAHG HVHGAHDHHH DHDHDGGGSG GGSGGGSGGG

SGGGSGGGKV AKDLVVSLAY QVRTEDGVLV DESPVSAPLD YLHGHGSLIS GLETALEGHE

VGDKFDVAVG ANDAYGQYDE NLVQRVPKDV FMGVDELQVG MRFLAETDQG PVPVEITAVE

DDHVVVDGNH MLAGQNLKFN VEVVAIREAT EEELAHGHVH GAHDHHHDHD HDGGGSGGGS

GGGSGGGSGG GSGGGREAAH SDLGYWIESE KNDTWRLKRA HLIEMKTAEW PKSHTLWTDG

VEESDLIIPK SLAGPLSHHN TREGYRTQVK GPWHSEELEI RFEECPGTKV YVEETCGTRG

PSLRSTTASG RVIEEWCCRE CTMPPLSFRA KDGCWYGMEI RPRKEPESNL VRSMVTALEH

HHHHH,

SEQ ID NO: 23 Fusion protein of E. coli SlyD with Zika virus NS1 β-
ladder domain (aa 191-352, strain Mr 766)
MKVAKDLVVS LAYQVRTEDG VLVDESPVSA PLDYLHGHGS LISGLETALE GHEVGDKFDV

AVGANDAYGQ YDENLVQRVP KDVFMGVDEL QVGMRFLAET DQGPVPVEIT AVEDDHVVVD

GNHMLAGQNL KFNVEVVAIR EATEEELAHG HVHGAHDHHH DHDHDGGGSG GGSGGGSGGG

SGGGSGGGRE AAHSDLGYWI ESEKNDTWRL KRAHLIEMKT AEWPKSHTLW TDGVEESDLI
```

```
-continued
IPKSLAGPLS HHNTREGYRT QVKGPWHSEE LEIRFEECPG TKVYVEETCG TRGPSLRSTT

ASGRVIEEWC CRECTMPPLS FRAKDGCWYG MEIRPRKEPE SNLVRSMVTA LEHHHHHH,

SEQ ID NO: 24 Dengue virus type 1 NS1 β-ladder domain aa 191-352
SKAVHADMGY WIESEKNETW KLARASFIEV KTAIWPKSHT LWSNGVLESE MIIPKIYGGP ISQHNYRPGY

FTQTAGPWHL GKLELDFDLC EGTTVVVDEH CGNRGPSLRT TSVTGKIIHE WCCRSCTLPP LRFRGEDGCW

YGMEIRPVKE KEENLVKSMV SA,

SEQ ID NO: 25 Dengue virus type 2 NS1 β-ladder domain aa 191-352
NRAVHADMGY WIESALNDTW KIEKASFIEV KNAHWPKSHT LWSNGVLESE MIIPKNLAGP VSQHNYRPGY

HTQIAGPWHL GKLEMDFDFC DGTTVVVTED CONRGPSLRT TTASGKLITE WCCRSCTLPP LRYRGEDGCW

YGMEIRPLKE KEENLVNSLV TA,

SEQ ID NO: 26 Dengue virus type 3 NS1 β-ladder domain aa 191-352
ERAVHADMGY WIESQKNGSW KLEKASLIEV KTATWPKSHT LWSNGVLESD MIIPKSLAGP ISQHNYRPGY

HTQTAGPWHL GKLELDFNYC EGTTVVITEN CGTRGPSLRT TTVSGKLIHE WCCRSCTLPP LRYMGEDGCW

YGMEIRPINE KEENMVKSLV SA,

SEQ ID NO: 27 Dengue virus type 4 NS1 β-ladder domain aa 191-352
QKAVHADMGY WIESSKNQTW QIEKASLIEV KTALWPKTHT LWSNGVLESQ MLIPRSYAGP FSQHNYRQGY

ATQTAGPWHL GKLEIDFGEC PGTTVTIQED CDHRGPSLRT TTASGKLVTQ WCCRSCTMPP LRFLGEDGCW

YGMEIRPLSE KEENMVKSQV TA,
```

The sequences of SEQ ID NOs 28-35 are shown in the electronic sequence listing. Amino acid X indicates that this position can be filled by alanine, cysteine or serine (X=A or C or S).

SEQ ID NO:28, Fusion protein of tandem *E. coli* SlyD with Dengue virus type 1 NS1 wing domain aa 30-180

SEQ ID NO:29, Fusion protein of tandem *E. coli* SlyD with Dengue virus type 2 NS1 wing domain aa 30-180

SEQ ID NO:30, Fusion protein of tandem *E. coli* SlyD with Dengue virus type 3 NS1 wing domain aa 30-180

SEQ ID NO:31, Fusion protein of tandem *E. coli* SlyD with Dengue virus type 4 NS1 wing domain aa 30-180

SEQ ID NO:32, Fusion protein of tandem *E. coli* SlyD with Dengue virus type 1 NS1 ß-ladder domain aa 191-352

SEQ ID NO:33, Fusion protein of tandem *E. coli* SlyD with Dengue virus type 2 NS1 ß-ladder domain aa 191-352

SEQ ID NO:34, Fusion protein of tandem *E. coli* SlyD with Dengue virus type 3 NS1 ß-ladder domain aa 191-352

SEQ ID NO:35, Fusion protein of tandem *E. coli* SlyD with Dengue virus type 4 NS1 ß-ladder domain aa 191-352

DETAILED DESCRIPTION OF THE INVENTION

Commercially available immunoassays (both IgG and IgM immunoassays) for detecting flaviviral antibodies such as antibodies against Zika virus, Dengue virus and West Nile virus are based on the ELISA principle. However, the known immunoassays evidently use the full length NS1 antigen that on the one hand is highly immunoreactive but on the other hand shows a high immunological cross-reactivity with antibodies raised against the NS1 homologues of Zika, Dengue and other flaviviruses like West Nile virus, yellow fever virus or other flaviviruses. In addition, due to its complex quaternary structure it is not possible to provide NS1 in a soluble and stable monomeric form which would be a prerequisite in designing an immunoassay for specific IgG detection in the double-antigen sandwich format. Dedicated flaviviral NS1 antigens that would fulfill these requirements and would enable highly specific immunoassays suitable for automation have not been described in prior art. Surprisingly, by confining the flaviviral NS1 antigen to its wing domain and removing the so-called ß-ladder domain sequences of the NS1 antigen, a soluble and stable NS1 antigen variant is obtained that is able to specifically detect antibodies against a specific kind of flavivirus.

When samples positive for anti-Zika virus antibodies were tested with two different fragments of the NS1 antigen of Zika, i.e. with the so-called "wing" domain antigen and the so-called "ß-ladder" domain antigen, it became evident that both antigens are able to detect anti-Zika antibodies. However, we found out that the wing domain antigen does not cross-react with Dengue antibody positive samples whereas the Zika NS1 ß-ladder domain antigen does cross-react with Dengue antibody positive samples, leading to false positive results and to erroneous conclusions. Additional blocking experiments with anti-Zika positive sera and NS1 antigens of related arboviruses conclusively showed that the Zika NS1 wing domain antigen signal can hardly be quenched by these related arboviral NS1 antigens whereas the Zika NS1 ß-ladder domain signal is quenched significantly. We infer that the ß-ladder antigen is considerably blocked from binding to the immunoglobulins by the competing related arboviral NS1 antigens. Thus, we were able to show that the Zika NS1 wing domain antigen is less susceptible to immunological cross-reactivity with other arboviral NS1 homologues. As a consequence, the Zika NS1 wing domain enables an immunoassay for anti-Zika antibodies with superior specificity that is capable of diagnosing Zika virus infections in the presence of other (recent or past) arbovirus infections, in an embodiment discriminating Zika virus infections from Dengue virus infections.

Similarly, for Dengue virus antibody detection we were able to identify NS1 wing domain antigens from all of the four Dengue virus serotypes that we overexpressed in *E. coli* with high yield, and which refold into an immunoreactive form after purification and functional solubilization. We found evidence that the individual Dengue wing domains of DENV 1-4 react very differently with a pre-characterized commercial set of DENV positive sera. The results indicate that an immunological differentiation of the four distinct Dengue virus serotypes is feasible using the Dengue NS1 wing domain as antigen in an immunoassay. Overall, the Dengue NS1 wing domain lacking the ß-ladder domain of NS1 is an antigen suitable for specific Dengue antibody detection.

In a parallel approach for West Nile virus we were also able to overproduce (in *E. coli*) to purify and to functionally refold an NS1 wing domain antigen that allows specific detection of antibodies against West Nile virus.

Based on our experimental findings we conclude that the flaviviral NS1 wing domain that does not contain amino acid sequences of a NS1 ß-ladder domain serves as an excellent antigen for specific detection of antibodies against the flavivirus corresponding to the NS1 wing domain amino acid sequence used, thereby discriminating it from other flaviviruses. In particular, this conclusion is applicable to the specific detection of Zika, Dengue and West Nile virus antibodies.

The invention therefore concerns a polypeptide suitable for detecting antibodies against a flavivirus in an isolated biological sample comprising a flavivirus NS1 wing domain specific amino acid sequence, wherein no amino acid sequences from the NS1 ß-ladder domain of said flavivirus are present in said polypeptide. In an embodiment, no further amino acid sequences of said flavivirus are present in said polypeptide. In another embodiment, the flavivirus is selected from the group consisting of Zika virus (ZIKV), West-Nile virus (WNV), Dengue virus types 1-4 (DENV1-4), tick-borne encephalitis virus (TBEV), yellow fever virus (YFV), Japanese encephalitis virus (JEV), in an embodiment the flavivirus is Dengue virus types 1-4.

In an embodiment, the NS1 wing domain specific amino acid sequence consists essentially of a polypeptide selected from the group consisting of SEQ ID NOs. 1, 2, 5, 7, 9, 11, 13, 15, 17 and 19, in an embodiment selected from the group consisting of SEQ ID NOs. 7, 9, 11, 13 and 15 in an embodiment selected from the group consisting of SEQ ID NOs. 7, 9, 11 and 13 (NS1 domain of Dengue virus types 1-4).

The terms "NS1", "NS1 antigen", NS1 polypeptide" are used synonymously and refer to the non-structural antigen no. 1 (NS1) within the viral precursor polyprotein and relate (unless specified differently) to the full length antigen NS1. The structure of this protein has been described for West Nile virus and Dengue virus 2 in Akey et al, supra. For Zika NS1 the structure of the C-terminal domain (amino acid residues 172-352) has been described by Song et al. (supra) and the complete NS1 three-dimensional structure has been described in further detail by Brown et al. (supra). The Zika NS1 sequence comprises 352 amino acids and is shown in SEQ ID NO: 3, tick-borne encephalitis virus NS1 in SEQ ID NO:5, Dengue virus type 1 NS1 in SEQ ID NO: 8, Dengue virus type 2 NS1 in SEQ ID NO: 10, Dengue virus type 3 NS1 in SEQ ID NO: 12, Dengue virus type 4 NS1 in SEQ ID NO: 14, West Nile virus NS1 in SEQ ID NO:16, yellow fever virus NS1 in SEQ ID NO:18, Japanese fever virus NS1 in SEQ ID NO:20. The term "NS1 wing" or "NS1 wing domain", "variant of NS1 wing" or "NS1 wing region" refers to a domain within the NS1 polypeptide and is therefore a partial sequence of NS1. For the Zika NS1 wing domain this is exemplified in SEQ ID NOs:1 and 2, for NS1 wing domains of further flaviviruses in SEQ IDs NO:5 (TBEV), NO:7 (DENV1), NO:9 (DENV2), NO:11 (DENV3), NO:13 (DENV4), NO:15 (WNV), NO: 17 (YEV) and NO: 19 (JEV). Also the terms "polypeptide", "polypeptides", "antigen" and "antigens" are understood as synonyms unless further specified.

The synonymous terms "ß-ladder", "ß-ladder domain" or "ladder tip antigen" or "ladder tip", "ladder tip domain", "ladder tip polypeptide", "ladder tip antigen" refer to a NS1 domain located C-terminally adjacent to the wing domain. This domain has been described for West Nile virus and Dengue virus 2 in Akey et al, supra. For Zika virus this NS1 domain has been described by Song et al., supra, and Brown et al., supra. For the Zika NS1 ß-ladder domain the amino acid sequence is exemplified in SEQ ID NO:4, for Dengue virus types 1-4 in SEQ ID NOs:24-27. The ß-ladder domains of the other flaviviruses can be seen in the C-terminal parts (aa 191-352) of the full length NS1 sequences corresponding to each virus.

These definitions are applicable to all arboviruses within this specification. The following arboviruses that belong to the flavivirus family can be abbreviated as follows: West Nile virus (West Nile, WNV), tick-borne encephalitis virus (TBEV or FSME), Dengue virus 1-4 (Dengue, the four virus strains of Dengue: DENV 1-4), yellow fever virus (YFV), Japanese encephalitis virus (JEV).

According to the invention, a flavivirus NS1 wing domain specific amino acid sequence is an amino acid sequence wherein no amino acid sequences from the NS1 ß-ladder domain of said flavivirus are present in said polypeptide. In an embodiment, no further amino acid sequences of said flavivirus are present in said polypeptide. For example a Zika NS1 wing domain polypeptide contains only a wing domain sequence, in an embodiment contains SEQ ID NOs. 1 or 2. No further Zika virus in an embodiment, no Zika virus NS1 specific amino acid sequences are present in this sequence, in an embodiment, SEQ ID NO:4 is not present in said polypeptide sequence. In a further example, DENV1 NS1 wing domain contains SEQ ID NO: 7 but does not contain SEQ ID NO:24 (ß-ladder). Other examples are DENV2 NS1 wing (SEQ ID NO:9) wherein SEQ ID NO: 25 is absent; DENV3 NS1 wing (SEQ ID NO: 11) wherein SEQ ID NO: 26 is absent; DENV4 NS1 wing (SEQ ID NO: 13) wherein SEQ ID NO: 27 is absent; WNV NS1 wing (SEQ ID NO: 15) wherein the WNV ß-ladder domain is absent. The absence of NS1 ß-ladder domain specific sequences and in an embodiment the absence of further flavivirus NS1 specific sequences or of further flavivirus specific sequences supports the aim to either reduce or completely avoid cross-reactivities with antibodies raised against other arboviruses.

However, variants of the flavivirus NS1 wing domain polypeptide are encompassed as well. These variants may easily be created by a person skilled in the art by conservative or homologous substitutions of the disclosed amino acid sequences (such as e.g. substitutions of a cysteine by alanine or serine, or substitutions of isoleucine by valine, or vice versa). The term "variants" in this context also relates to a protein or a protein fragment (i.e. a polypeptide or peptide) substantially similar to said protein. For example, modifications such as C- or N-terminal truncations at one end or at both ends by 1 to 10 amino acids, in an embodiment by 1 to 5 amino acids, are within the scope of the claimed flavivirus NS1 wing domain antigens. In particular, a variant may be an isoform which shows amino acid exchanges, deletions or insertions compared to the amino acid sequence of the most prevalent protein isoform. In one embodiment, such a substantially similar protein has a sequence similarity to the most prevalent isoform of the protein of at least 80%, in another embodiment at least 85% or at least 90%, in yet another embodiment at least 95%. The term "variant" also relates to a post-translationally modified protein such as a glycosylated or phosphorylated protein. According to the invention a variant classifies as a favivirus NS1 wing domain variant as long as the immunoreactivity in an in vitro diagnostic immunoassay is unchanged or largely maintained, i.e. the variant is still able to bind and detect anti-flavivirus antibodies present in an isolated sample while antibodies raised against other arboviruses are not detected or detected to a much lower extent. In addition, the overall three-dimensional structure of said flavivirus polypeptide remains unaltered, so that epitopes that were previously (i.e. in the wild type) present and accessible for binding to antibodies are still present and accessible in the variant.

A "variant" is also a protein or antigen which has been modified for example by covalent or non-covalent attachment of a label or carrier moiety to the protein or antigen. Possible labels are radioactive, fluorescent, chemiluminescent, electrochemiluminescent, enzymes or others e.g. like digoxin, digoxigenin or biotin. These labels are known to a person skilled in the art.

When a provided polypeptide sequence information specified in the form of SEQ ID NOs is described by the term "consisting essentially of" (i.e., said sequence) this means that the sequence is present as literally listed but can also be present as variants that do not materially affect the basic characteristics of this polypeptide in terms of immunological binding to antibodies. An example of this would be the deletion or addition of only few amino acids at the N- and/or C-terminal end of this peptide as well as the exchange of a similar amino acid as, e.g., alanine for serine, isoleucine for valine, and vice versa.

The flavivirus NS1 wing domain antigens of the current invention are soluble, stable and immunoreactive, i.e. they are suitable as antigens for use in an immunological assay. This means that the antigens according to the invention are soluble under physiological buffer conditions, for example in a phosphate buffer system at ambient temperature without addition of detergents. The antigens are also capable of binding to or being recognized and bound by antibodies specific for flavivirus NS1 wing domain, like e.g. anti-Zika or anti-Dengue antibodies present in an isolated sample such as human sera.

In an embodiment, the addition of non-flavivirus-specific linker or peptidic fusion amino acid sequences to the flavivirus NS1 wing domain polypeptides is possible as these sequences are not specific for anti-flavivirus antibodies and would not interfere with the in vitro diagnostic immunoassay.

In an embodiment the flavivirus NS1 wing domain antigens may be fused to a chaperone. The term "fusion protein", "fusion polypeptide" or "fusion antigen" refers to a protein comprising a flavivirus NS1 wing domain polypeptide and at least one protein part derived from a chaperone that serves the role of a fusion partner.

Chaperones are well-known folding helper proteins that assist the folding and maintenance of the structural integrity of other proteins. Examples of folding helpers are described in detail in WO 03/000877. According to the invention chaperones of the peptidyl prolyl isomerase class such as chaperones of the FKBP family can be used for fusion to the flavivirus NS1 wing domain antigen variants. Examples of FKBP chaperones suitable as fusion partners are FkpA, SlyD and SlpA. A further chaperone suitable as a fusion partner for the flavivirus NS1 wing antigen is Skp, a trimeric chaperone from the periplasm of E. coli, not belonging to the FKBP family. It is not always necessary to use the complete sequence of a chaperone. Functional fragments of chaperones (so-called binding-competent modules or polypeptide-binding motifs) which still possess the required abilities and functions may also be used (cf. WO 98/13496).

In a further embodiment of the invention at least one or at least two modules of an FKBP chaperone such as e.g. E. coli SlyD, SlpA or FkpA are used as fusion moieties for expression of the flavivirus NS1 wing domain antigen. The chaperone Skp may be used as a fusion partner as well. The fusion of two FKBP-chaperone domains results in improved solubility of the resulting fusion polypeptide. The fusion moieties may be located at the N-terminus or at the C-terminus or at both ends (sandwich-like) of the flavivirus NS1 wing domain antigen.

In an embodiment the flavivirus NS1 wing domain antigen is fused to an oligomeric chaperone. Oligomeric chaperones are chaperones that naturally form dimers, trimers or even higher multimers so that a plurality of monomeric subunits are assembled into a well-defined functional quaternary structure by specific non-covalent interactions. Thereby, the covalently fused antigens are coerced into a higher epitope density as well. Preferred oligomeric chaperones are FkpA and Skp. Multimerized antigens are particularly useful in detecting IgM antibodies and hence early immune responses immediately after infections.

In an embodiment, the flavivirus NS1 wing domain polypeptide is fused to one, two or more chaperone molecules of a bacterial SlyD, SlpA, FkpA or Skp, in an embodiment of E. coli SlyD, SlpA, FkpA or Skp. In a further embodiment the flavivirus NS1 wing domain polypeptide consists of SEQ ID NO:21 (Zika), 28 (DENV1), 29 (DENV2), 30 (DENV3) or 31 (DENV4).

Another embodiment of the invention is a flaviviral NS1 wing domain antigen that does not immunologically cross-react with antibodies raised against structurally related antigens from other flaviviruses. In an example, Zika NS1 wing domain antigen does not immunologically cross-react with antibodies raised against structurally related antigens from tick-borne encephalitis virus comprising any of SEQ ID NOs:5 or 6, and/or from Dengue virus 1-4 comprising any of SEQ ID NOs:7 to 14, and/or from West Nile virus comprising any of SEQ ID NOs:15 or 16, and/or from yellow fever virus comprising any of SEQ ID NOs: 17 or 18, and/or from Japanese encephalitis virus comprising any of SEQ ID NOs: 19 to 20, but immunologically reacts with antibodies raised against full length Zika virus NS1 antigen according to SEQ ID NO:3. In a further embodiment said Zika NS1 antigen is a Zika NS1 wing domain antigen wherein the Zika-specific sequence consists essentially of SEQ ID NO: 1 or 2, in an embodiment consists of SEQ ID NO: 1 or 2. In accordance with Zika NS1 also the other flaviviral NS1 antigens like e.g. NS1 of Dengue types 1-4 do not immunologically cross-react with antibodies raised against structurally related antigens from the other flavivirus, i.e. in the Dengue example do not immunologically cross-react with NS1 wing domains of Zika, TBEV, WNV, YEV and JEV.

The term "does not immunologically cross-react" designates a strongly reduced or completely abolished undesired immunological reactivity. The term "immunological cross-reactivity" has been coined to illustrate an unwanted binding of immunoglobulins which is due to similarities in sequence or structure of an antigen with the immunogen, against which the antibodies have originally been mounted. In an embodiment, Zika virus NS1 wing domain polypeptides show a completely abolished or strongly reduced immunological reactivity towards antibodies or towards a subset of antibodies raised against homologous or related arboviral NS1 antigens named above as compared to the full length Zika virus NS1 polypeptide. In yet another embodiment Zika virus NS1 wing domain polypeptides show a strongly reduced immunological cross-reactivity towards antibodies or towards a subset of antibodies raised against Dengue virus, in an embodiment towards antibodies raised against Dengue virus types 1, 2, 3, 4. In a further embodiment, a strongly reduced immunological cross-reactivity of the Zika virus NS1 wing domain polypeptides applies also to antibodies or a subset of antibodies raised against yellow fever virus. In yet another embodiment Dengue virus types 1-4 virus NS1 wing domain polypeptides show a strongly reduced immunological cross-reactivity towards antibodies or towards a subset of antibodies raised against Zika virus.

The expression "does not immunologically cross-react" also refers to a situation where in an immunoassay in a double antigen sandwich format for detecting antibodies the sample antibodies (i.e., the analyte antibodies) are bound by two specific antigens: one is capable of being bound to a solid phase and the other carries a label, the sample antibody is sandwiched between both antigens. In the presence of analyte antibodies the labeled antigen is recruited—within the resulting ternary immune complex—to the solid phase and yields a signal. In the present case, a flavivirus NS1 wing domain polypeptide, such as e.g. Zika NS1 wing, is labeled and the measured signal is set as 100%. In a parallel or subsequent experiment, the same assay is run with another aliquot of the same (positive) sample and in addition a non-labeled antigen with an amino acid sequence suspected to compete with the labeled antigen is added to the mixture. In the present case, full length NS1 polypeptides of either TBEV, DENV1-4, WNV, YFV or JEV are added. In another embodiment, NS1 polypeptides consisting of or comprising only the NS1 wing domain of either TBEV, DENV1-4, WNV, YFV or JEV are added. When the signal obtained after measurement is maintained at about at least 70% signal recovery, in an embodiment at least 80% signal recovery, in an embodiment at least 85% signal recovery, in an embodiment at least 90% signal recovery of the original signal, the flaviviral (in this example: Zika) NS1 polypeptide is not prone to signal quenching. It is not outcompeted by the added antigens and therefore withstands potentially cross-reactive substances. For illustration, such blocking experiments are described in example 2 (table 2).

In an embodiment, NS1 full length or NS1 wing domain peptides from tick-borne encephalitis virus comprising any of SEQ ID NOs:5 or 6, and/or from Dengue virus 1-4 comprising any of SEQ ID NOs:7 to 14, and/or from West Nile virus comprising any of SEQ ID NOs:15 or 16, and/or from yellow fever virus comprising any of SEQ ID NOs:17 or 18, and/or from Japanese encephalitis virus comprising any of SEQ ID NOs:19 to 20, are added in the above-described blocking experiment.

In another embodiment, the Zika NS1 wing domain polypeptide immunologically reacts with antibodies, or a subset of antibodies, raised against full-length NS1 antigen as shown in SEQ ID NO:3. This means that in the above-disclosed assay setup, the signal of the Zika NS1 wing domain polypeptide should be fully quenched (100%) upon addition of the full-length Zika NS1 polypeptide.

The approach how to determine immunological cross-reactivity to Zika-related viruses is further described in example 2 and can be transferred in an analogous way to blocking experiments with other flaviviruses.

The flavivirus NS1 polypeptides (both wing domain and ß-ladder domain) as well as the polypeptides applied for the blocking experiments of example 2 can be generated and prepared by means of recombinant DNA techniques and protein purification techniques as known in the art.

Another aspect of the invention therefore is a recombinant DNA molecule encoding a flavivirus NS1 wing domain antigen, in an embodiment an antigen according to SEQ ID NOs 1, 2, 21, 5, 7, 9, 11, 13, 15, 17, 19, 28, 29, 30 and 31 and variants thereof as defined further above.

The term "recombinant DNA molecule" refers to a molecule which is made by the combination of two otherwise separated segments of DNA sequence accomplished by the artificial manipulation of isolated segments of polynucleotides by genetic engineering techniques or by chemical synthesis. In doing so one may join together polynucleotide segments of desired functions to generate a desired combination of functions. Recombinant DNA techniques for expression of proteins in prokaryotic or lower or higher eukaryotic host cells are well known in the art. They have been described e.g. by Sambrook et al., (1989, Molecular Cloning: A Laboratory Manual)

The recombinant DNA molecules according to the invention may also contain sequences encoding linker peptides of 5 to 100 amino acid residues in between the flavivirus NS1 wing domain antigen and the fusion moieties and also between several fusion moieties. Such a linker sequence may for example harbor a proteolytic cleavage site.

A further aspect of the invention is an expression vector comprising operably linked a recombinant DNA molecule according to the present invention, i.e., a recombinant DNA molecule encoding a flavivirus NS1 wing domain antigen and optionally a peptidyl prolyl isomerase chaperone, such as an FKBP-chaperone, wherein the FKBP-chaperone is selected from FkpA, SlyD and SlpA. In an alternative embodiment the recombinant DNA molecule encodes a fusion protein comprising a flavivirus NS1 wing domain antigen and Skp. The expression vector comprising a recombinant DNA according to the present invention may be used to express the flavivirus NS1 wing domain antigen in a cell free translation system or may be used to transform a host cell for expression of the flavivirus NS1 wing domain antigen according to methods well known in the art. Another aspect of the invention therefore relates to a host cell transformed with an expression vector according to the present invention. In one embodiment of the current invention the recombinant flavivirus NS1 wing domain antigens are produced in *E. coli* cells.

An additional aspect is a method for producing a soluble, stable and immunoreactive flavivirus NS1 wing domain antigen. Said flavivirus NS1 wing domain antigen may be produced as a fusion protein containing the flavivirus NS1 wing domain antigen and a chaperone. Preferably, a chaperone such as Skp or a peptidyl prolyl isomerase class chaperone like an FKBP chaperone is used. In a further embodiment of the invention said FKBP chaperone is selected from the group consisting of SlyD, FkpA and SlpA.

This method comprises the steps of
a) culturing host cells transformed with the above-described expression vector containing a gene encoding an flavivirus NS1 wing domain antigen
b) expression of the gene encoding said flavivirus NS1 wing domain antigen
c) purification of said flavivirus NS1 wing domain antigen.
 Optionally, as an additional step d), functional solubilization needs to be carried out so that the flavivirus NS1 wing domain antigen is brought into a soluble and immunoreactive conformation by means of refolding techniques known in the art.

Yet another embodiment is a method for producing a soluble, stable and immunoreactive flavivirus NS1 wing domain antigen in a cell-free in vitro translation system.

An additional aspect of the present invention concerns a method for the detection of anti-flavivirus antibodies in an isolated human sample wherein a flavivirus NS1 wing domain antigen according to the invention is used as a binding partner for the antibodies. The invention thus covers a method for the detection of antibodies specific for flavivirus, in particular for a first flavivirus species in an isolated sample, said method comprising a) forming an immunoreaction admixture by admixing a body fluid sample with a flavivirus NS1 wing domain antigen according to the invention, b) maintaining said immunoreaction admixture for a time period sufficient for allowing antibodies against said flavivirus NS1 wing domain antigen present in the body fluid sample to immunoreact with said flavivirus NS1 wing domain antigen to form an immunoreaction product; and c) detecting the presence and/or the concentration of any of said immunoreaction product.

The term "first flavivirus" or "first flavivirus species" throughout this specification means that antibodies specific for one species of flavivirus are detected in the presence of antibodies against at least a second or multiple flavivirus species. Often, patient samples do not only contain one kind of flavivirus antibodies but also contain antibodies from infections that may have occurred in the past. As an example, if a first flavivirus species is Dengue virus then antibodies against a second species like e.g. Zika or West Nile virus or both (multiple) viruses are not detected by the immunoassay.

In an embodiment, said method concerns the detection of anti-Dengue antibodies, applying Dengue virus types 1-4 NS1 wing domain antigens, individually or all four antigen types as a binding partner for the sample antibodies. In an embodiment, the Dengue NS1 wing domain antigens are polypeptides selected from the group consisting of SEQ ID NOs. 7, 9, 11, 13, 28, 29, 30 and 31.

In a further aspect said method is suitable for detecting flavivirus antibodies of the IgG and the IgM subclass or of both classes in the same immunoassay. In an embodiment, said flavivirus antibodies are anti-Dengue virus types 1-4 antibodies.

Immunoassays for detection of antibodies are well known in the art, and so are methods for carrying out such assays and practical applications and procedures. The flavivirus NS1 antigens according to the invention can be used to improve assays for the detection of anti-flavivirus antibodies independently of the labels used and independently of the mode of detection (e.g., radioisotope assay, enzyme immunoassay, electrochemiluminescence assay, etc.) or the assay principle (e.g., test strip assay, sandwich assay, indirect test concept or homogenous assay, etc.).

In an embodiment of the invention the immunoassay is a particle-based immunoassay applying microparticles as solid phase. A "particle" as used herein means a small, localized object to which can be ascribed a physical property such as volume, mass or average size. Microparticles may accordingly be of a symmetrical, globular, essentially globular or spherical shape, or be of an irregular, asymmetric shape or form. The size of a particle envisaged by the present invention may vary. In one embodiment the microparticles used are of globular shape, e.g. microparticles with a diameter in the nanometer and micrometer range. In one embodiment the microparticles used in a method according to the present disclosure have a diameter of 50 nanometers to 20 micrometers. In a further embodiment the microparticles have a diameter of between 100 nm and 10 m. In one embodiment the microparticles used in a method according to the present disclosure have a diameter of 200 nm to 5 m or from 750 nm to 5 m.

Microparticles as defined herein above may comprise or consist of any suitable material known to the person skilled in the art, e.g. they may comprise or consist of or essentially consist of inorganic or organic material. Typically, they may comprise or consist of or essentially consist of metal or an alloy of metals, or an organic material, or comprise or consist of or essentially consist of carbohydrate elements. Examples of envisaged material for microparticles include agarose, polystyrene, latex, polyvinyl alcohol, silica and ferromagnetic metals, alloys or composition materials. In one embodiment the microparticles are magnetic or ferromagnetic metals, alloys or compositions. In further embodiments, the material may have specific properties and e.g. be hydrophobic, or hydrophilic. Such microparticles typically are dispersed in aqueous solutions and retain a small negative surface charge keeping the microparticles separated and avoiding non-specific clustering.

In one embodiment of the present invention, the microparticles are paramagnetic microparticles and the separation of such particles in the measurement method according to the present disclosure is facilitated by magnetic forces. Magnetic forces are applied to pull the paramagnetic or magnetic particles out of the solution/suspension and to retain them as desired while liquid of the solution/suspension can be removed and the particles can e.g. be washed.

All biological liquids known to the expert can be used as isolated samples for the detection of anti-flavivirus antibodies, in an embodiment anti-Dengue antibodies. The samples usually used are bodily liquids like whole blood, blood serum, blood plasma, urine or saliva, in an embodiment blood serum or plasma.

A further embodiment of the invention is an immunoassay for detecting anti-Zika antibodies in an isolated sample performed according to the so-called double antigen sandwich concept (DAGS).

Sometimes this assay concept is also termed double antigen bridge concept, because the two antigens are bridged by an antibody analyte. In such an assay the ability of an antibody to bind at least two different molecules of a given antigen with its two (IgG, IgE), four (IgA) or ten (IgM) paratopes is required and utilized.

In more detail, an immunoassay for the determination of anti-flavivirus antibodies according to the double antigen bridge format is carried out by incubating a sample containing the anti-flavivirus antibodies with two different flavivirus NS1 wing domain antigens of the same flavivirus, i.e. a first ("solid phase" or "capture") flavivirus NS1 wing domain antigen and a second flavivirus NS1 wing domain ("detection" or "reporter") antigen, wherein each of the said antigens binds specifically to said anti-flavivirus antibodies. The first antigen can be bound directly or indirectly to a solid phase and usually carries an effector group which is part of a bioaffine binding pair. In an embodiment, the anti-flavivirus antibody is an anti-Dengue antibody and the two different flavivirus NS1 wing domain antigens are from the same Dengue virus type.

One type of a bioaffine binding pair which is suitable for the method according to the present invention is a hapten and anti-hapten antibody binding pair. A hapten is an organic molecule with a molecular weight of 100 to 2000 Dalton, preferably of 150 to 1000 Dalton. Such small molecule can be rendered immunogenic by coupling it to a carrier molecule and anti-hapten antibodies can be generated according to standard procedures. The hapten may be selected from the group comprising sterols, bile acids, sexual hormones, corticoids, cardenolides, cardenolide-glycosides, bufadienolides, steroid-sapogenines and steroid alkaloids, cardenolides and cardenolide-glycosides. Representatives of these substance classes are digoxigenin, digitoxigenin, gitoxigenin, strophanthidin, digoxin, digitoxin, ditoxin, and strophanthin. Another suitable hapten is for example fluorescein. In an embodiment, a bioaffine binding pair comprises biotin and avidin/streptavidin or digoxin and anti-digoxin.

In yet another embodiment, the first antigen is conjugated to biotin and the complementary solid phase is coated with either avidin or streptavidin. The second antigen carries a label that confers specific detectability to this antigen molecule, either alone or in complex with other molecules. Thus an immunoreaction admixture is formed comprising the first antigen, the sample antibody and the second antigen. This ternary complex consisting of analyte antibody sandwiched in between two antigen molecules is termed immunocomplex or immunoreaction product. A solid phase to which the first antigen can be bound is added either before the addition of the sample to said antigens or after the immunoreaction admixture is formed. This immunoreaction admixture is maintained for a time period sufficient for allowing anti-flavivirus antibodies against said flavivirus NS1 wing domain antigens in the body fluid sample to immunoreact with said flavivirus NS1 wing domain antigens to form an immunoreaction product. Next step is a separation step wherein the liquid phase is separated from the solid phase. Finally, the presence of any of said immunoreaction product is detected in the solid or liquid phase or both.

In said DAGS immunoassay the basic structures of the "solid phase antigen" and the "detection antigen" are essentially the same. It is also possible to use, in a double antigen bridge assay, similar but different flavivirus NS1 wing domain antigens from the same flavivirus, which are immunologically cross-reactive. The essential requirement for performing such assays is that the relevant epitope or the relevant epitopes are present on both antigens. According to the invention it is possible to use the same or different fusion moieties for each flavivirus NS1 wing domain antigen (e.g. SlyD fused to Dengue virus type 1 NS1 wing domain antigen on the solid phase side and, e.g., FkpA fused to Dengue virus type 1 NS1 wing domain antigen on the detection side) as such variations significantly alleviate the problem of non-specific binding and thus mitigate the risk of false-positive results.

A further embodiment is a method for detecting anti-flavivirus virus antibodies (i.e., immunoglobulins) of the M class (IgM detection). In an embodiment of this method a flavivirus NS1 wing domain polypeptide as disclosed further above is applied in such a way that the multivalent IgM antibodies present in a sample specifically bind to the flavivirus NS1 wing domain antigen. In an embodiment, the flavivirus NS1 wing domain antigen is provided in a multimeric form by either chemically cross-linking the antigen or by fusing the antigen to an oligomerizing molecule such as an oligomeric chaperone, in an embodiment to FkpA or Skp. In another embodiment a flavivirus wing domain antigen is present in multiple form by connecting individual antigens in series, adjacent to each other. These individual antigen moieties can also be separated by linker molecules that are not flavivirus specific. In a further embodiment the multiple flavivirus antigens connected in series can additionally be multimerized by an oligomerization molecule such as an oligomeric chaperone like e.g. FkpA or Skp. In yet another embodiment the flavivirus NS1 wing domain polypeptide is used in a multimeric form wherein each polypeptide is present at least in duplicate form, in an embodiment it is present three to ten times.

In yet another embodiment of the IgM detection method of flavivirus-antibodies the IgM class antibodies present in the sample are bound to a solid phase by a so-called μ-capture component which usually is a binding partner or an antibody or antibody fragment that specifically binds to the Fc part of human IgM molecules, independently of the specificity of the IgM molecule. Said μ-capture component carries an effector group (such as biotin) which is part of a bioaffine pair with avidin or streptavidin. In an embodiment also other bioaffine pairs such as e.g. digoxin and anti-digoxin or further hapten and anti-haptens as described further above can be used. In an embodiment, a solid phase covered with avidin or streptavidin then attracts and binds the μ-capture component. In order to specifically detect the flavivirus-specific antibodies a flavivirus NS1 wing domain polypeptide as described is used in a labeled form to detect the anti-flavivirus antibodies of the IgM class.

Another embodiment is the use of a flavivirus NS1 wing domain polypeptide as detailed above in an in vitro diagnostic test, in an embodiment an immunoassay method as defined above, for the detection of anti-flavivirus virus antibodies.

As a further embodiment the maximal total duration of the immunoassay method for detecting flavivirus antibodies is less than one hour, i.e. less than 60 minutes, in an embodiment less than 30 minutes, in a further embodiment less than 20 minutes, in an embodiment between 15 and 30 minutes, in an embodiment between 15 to 20 minutes. The duration includes pipetting the sample and the reagents necessary to carry out the assay as well as incubation time, optional washing steps, the detection step and also the final output of the result.

An additional subject matter of the invention is a reagent kit for the detection of antibodies against flavivirus that comprises a flavivirus NS1 wing domain polypeptide disclosed above. In an embodiment a reagent kit comprises in separate containers or in separated compartments of a single container unit at least microparticles coated with avidin or streptavidin, and a flavivirus NS1 wing domain polypeptide as detailed before. In another embodiment, said microparticles are coated with one partner of other bioaffine pairs as described further above, such as e.g. digoxin and anti-digoxin, hapten and anti-hapten. In an embodiment, said flavivirus NS1 wing domain polypeptide is covalently coupled to biotin. In an embodiment, said flavivirus NS1 wing domain is covalently coupled to the second partner of other bioaffine pairs such as e.g. digoxin and anti-digoxin, hapten and anti-hapten. In another embodiment, said flavivirus NS1 wing domain polypeptide is covalently coupled to a detectable label, in an embodiment to an electrochemiluminescent complex. In a further embodiment also chemiluminescent labels such as e.g. acridinium ester or radioactive or fluorescent compounds or enzymes can be applied as label. In yet another embodiment, said reagent kit comprises in separate containers or in separated compartments of a single container unit at least microparticles coated with avidin or streptavidin, a first flavivirus NS1 wing domain polypeptide covalently coupled to biotin and a second flavivirus NS1 wing domain polypeptide that is covalently coupled to a detectable label, e.g. to an electrochemiluminescent ruthenium complex or an electrochemiluminescent iridium complex. In an embodiment, the peptide sequences of the first and second flavivirus NS1 wing domain polypeptide are identical.

A further embodiment is a reagent kit for detecting anti-flavivirus antibodies of the IgM class, comprising in separate containers or in separated compartments of a single container unit at least microparticles coated with avidin or streptavidin, and a µ-capture binding partner that is covalently coupled to biotin. In a further embodiment said IgM detection reagent kit additionally contains flavivirus NS1 wing domain polypeptide which is covalently coupled to a detectable label, in an embodiment to an electrochemiluminescent complex.

The term single container unit relates to the fact that for many automatic analyzers, like the Elecsys® analyzer series from Roche diagnostics, the reagents required to measure a certain analyte are provided in the form of a "reagent pack", i.e. as one container unit fitting on the analyzer and containing in different compartments all the key reagents required for measurement of the analyte of interest.

In addition, the reagent kits defined above contain controls and standard solutions as well as reagents in one or more solutions with the common additives, buffers, salts, detergents and the like as used by the average man skilled in the art along with instructions for use.

In yet another aspect, the invention concerns a method for detecting antibodies against a first flavivirus (or first flavivirus species) in an isolated biological sample that is presumed to contain antibodies against at least one other, i.e. at least one second flavivirus (or second flavivirus species) that is not identical to the virus in scope of antibody detection. For example, the analyte is an antibody against Dengue virus ("first flavivirus species"). In this method, Dengue virus NS1 polypeptide comprising a complete or partial sequence of the ß-ladder domain is applied as specific binding partner, i.e. not only the NS1 wing domain but the complete NS1 antigen. In this experimental setup, cross-reactivity against other non-Dengue flaviviruses is expected due to the presence of the highly conserved ß-ladder domain peptide sequences in the specific binding partner. In order to eliminate this interference a polypeptide comprising solely the NS1 ß-ladder domain of said first flavivirus (in this example Dengue) is added in an unlabeled form so that the cross-reacting antibodies of non-Dengue origin (at least one second flavivirus species) are bound and quenched. In an embodiment, the ß-ladder domain is added as a quencher, in a further embodiment said ß-ladder domain polypeptide consists essentially of at least one of SEQ ID NOs:24, 25, 26 and 17, in an embodiment consists of at least one of SEQ ID NOs:24, 25, 26 and 17.

Usually Dengue virus types 1 to 4 are not distinguished from each other by means of serology. As a consequence, Dengue 1-4 is regarded as one "flavivirus species", namely Dengue.

The following embodiments are also part of the invention:

Embodiments

1. A polypeptide suitable for detecting antibodies against a flavivirus in an isolated biological sample comprising a flavivirus NS1 wing domain specific amino acid sequence, wherein no amino acid sequences from the NS1 ß-ladder domain of said flavivirus are present in said polypeptide.
2. A polypeptide according to embodiment 1, wherein no further amino acid sequences of said flavivirus are present in said polypeptide.
3. A polypeptide according to any of embodiments 1 or 2, wherein said flavivirus is selected from the group consisting of Zika virus (ZIKV), West-Nile virus (WNV), Dengue virus types 1-4 (DENV1-4), tick-borne encephalitis virus (TBEV), yellow fever virus (YFV), Japanese encephalitis virus (JEV).
4. A polypeptide according to any of embodiments 1 to 3, wherein said flavivirus NS1 wing domain specific amino acid sequence consists essentially of a polypeptide selected from the group consisting of SEQ ID NOs. 1, 2, 5, 7, 9, 11, 13, 15, 17 and 19, in an embodiment selected from the group consisting of SEQ ID NOs. 7, 9, 11, 13 and 15, in an embodiment selected from the group consisting of SEQ ID NOs. 7, 9, 11 and 13 (NS1 domain of Dengue virus types 1-4)
5. A polypeptide according to any of embodiments 1 to 4, wherein said polypeptide is fused to a chaperone.
6. A polypeptide according to any of embodiments 1 to 5, wherein said chaperone is selected from the group consisting of SlyD, SlpA, FkpA and Skp.
7. A polypeptide according to embodiment 6, selected from the group consisting of SEQ ID NOs.:21 (Zika), 28 (DENV1), 29 (DENV2), 30 (DENV3) and 31 (DENV4).
8. A method of producing a soluble and immunoreactive flavivirus NS1 wing domain polypeptide, said method comprising the steps of
    a) culturing host cells transformed with an expression vector comprising operably linked a recombinant DNA molecule encoding a flavivirus NS1 wing domain polypeptide according to any of embodiments 1 to 7,
    b) expression of said flavivirus NS1 wing domain polypeptide and
    c) purification of said flavivirus NS1 wing domain polypeptide.
9. A method for detecting antibodies specific for a first flavivirus species in an isolated sample, wherein a flavivirus NS1 wing domain polypeptide of said first flavivirus species according to any of claims 1 to 7 is used as a capture reagent and/or as a binding partner for said anti-flavivirus antibodies.
10. A method for detecting antibodies specific for a first flavivirus species in an isolated sample said method comprising
    a) forming an immunoreaction admixture by admixing a body fluid sample with a flavivirus NS1 wing domain polypeptide of said first flavivirus species according to any of embodiments 1 to 7
    b) maintaining said immunoreaction admixture for a time period sufficient for allowing antibodies present in the body fluid sample against said flavivirus NS1 wing domain polypeptide to immunoreact with said flavivirus NS1 wing domain polypeptide to form an immunoreaction product; and
    c) detecting the presence and/or the concentration of any of said immunoreaction product.
11. A method for detecting antibodies specific for a first flavivirus species in an isolated sample according to any of embodiments 9 or 10, wherein the detected antibody is an IgG antibody.
12. A method for detecting antibodies specific for a first flavivirus species in an isolated sample according to embodiment 9 to 11 wherein said immunoreaction is carried out in a double antigen sandwich format comprising
    a) adding to said sample a first flavivirus NS1 wing domain polypeptide of a first flavivirus species according to any of embodiments 1 to 7 which can be bound directly or indirectly to a solid phase and said first flavivirus NS1 wing domain polypeptide carries an effector group which is part of a bioaffine binding pair, and a second flavivirus NS1 wing domain polypeptide of said first flavivirus species according to any of embodiments 1 to 7, and said second flavivirus NS1 wing domain polypeptide carries a detectable label, wherein said first and second flavivirus NS1 wing domain polypeptides bind specifically to said anti-flavivirus antibodies, b) forming an immunoreaction admixture comprising said first flavivirus NS1 wing domain polypeptide, said sample antibody and said second flavivirus NS1 wing domain polypeptide, wherein a solid phase carrying a corresponding effector group of said bioaffine binding pair is added before, during or after forming the immunoreaction admixture, c) maintaining said immunoreaction admixture for a time period sufficient for allowing flavivirus antibodies against said first and second flavivirus NS1 wing domain polypeptides in the body fluid sample to immunoreact with said first and second flavivirus NS1 wing domain polypeptides to form an immunoreaction product, d) separating the liquid phase from the solid phase e) detecting the presence of any of said immunoreaction product in the solid or liquid phase or both.

13. A method for detecting antibodies specific for a first flavivirus species according to any of embodiments 9 to 12 wherein antibodies against a flavivirus species that is different from said first flavivirus species are not detected.

14. A method for detecting antibodies specific for a first flavivirus species according to any of embodiments 9 to 13, wherein said first flavivirus species is Dengue virus, in an embodiment each of individual Dengue virus types 1 to 4, in an embodiment all of Dengue virus types 1 to 4.

15. A method for detecting antibodies specific for a first flavivirus species according to any of embodiments 9 to 13, wherein said first flavivirus species is West-Nile virus (WNV).

16. A method for detecting antibodies specific for a first flavivirus species according to any of embodiments 9 to 13, wherein said first flavivirus species is tick-borne encephalitis virus (TBEV).

17. A method for detecting antibodies specific for a first flavivirus species according to any of embodiments 9 to 13, wherein said first flavivirus species is yellow fever virus (YFV).

18. A method for detecting antibodies specific for a first flavivirus species according to any of embodiments 9 to 13, wherein said first flavivirus species is Japanese encephalitis virus (JEV).

19. A method for detecting antibodies specific for a first flavivirus species according to any of embodiments 12 to 18, wherein said first flavivirus NS1 wing domain polypeptide carries a biotin moiety, and said second flavivirus NS1 wing domain polypeptide is labeled with an electrochemiluminescent moiety, in an embodiment with a ruthenium or iridium complex.

20. A method for detecting antibodies specific for a first flavivirus species in an isolated sample according to any of embodiments 9 to 10, wherein the detected antibody is an IgM antibody.

21. A method for detecting antibodies specific for a first flavivirus species of the IgM class according to embodiment 20, wherein said flavivirus NS1 wing domain polypeptide is used in a multimeric form, in an embodiment wherein said polypeptide is present at least in duplicate form, in an embodiment three to ten times.

22. A method according to any of embodiments 9 to 10, wherein said detected antibodies are IgM antibodies and wherein said IgM antibodies are captured on a solid phase by µ-capture binding partner.

23. A method for detecting IgM antibodies specific for a first flavivirus species in an isolated sample according to any of embodiments 20 to 22, wherein said immunoreaction is carried out in a µ-capture format comprising a) adding to said sample a µ-capture binding partner which can be bound directly or indirectly to a solid phase and said µ-capture binding partner carries an effector group which is part of a bioaffine binding pair, and a flavivirus NS1 wing domain polypeptide according to any of embodiments 1 to 6, and said flavivirus NS1 wing domain polypeptide carries a detectable label, wherein said µ-capture binding partner specifically binds to the Fc part of human IgM antibodies and said flavivirus NS1 wing domain polypeptide binds specifically to said anti-flavivirus antibodies, b) forming an immunoreaction admixture comprising said µ-capture binding partner, said sample antibodies and said flavivirus NS1 wing domain polypeptide, wherein a solid phase carrying a corresponding effector group of said bioaffine binding pair is added before, during or after forming the immunoreaction admixture, c) maintaining said immunoreaction admixture for a time period sufficient for allowing IgM antibodies against said flavivirus NS1 wing domain polypeptide in the body fluid sample to immunoreact with said flavivirus NS1 wing domain polypeptide to form an immunoreaction product, d) separating the liquid phase from the solid phase e) detecting the presence of any of said immunoreaction product in the solid or liquid phase or both.

24. A method according to any of embodiments 9 to 23, wherein said method does not use flavivirus NS1 polypeptides from the ß-ladder domain, in an embodiment does not use a polypeptide comprising an amino acid sequence according to any of SEQ ID NOs:4, 24, 25, 26, 27.

25. Use of a flavivirus NS1 wing domain polypeptide according to any of embodiments 1 to 7 in an in vitro diagnostic test for the detection of anti-flavivirus antibodies.

26. Use of a flavivirus NS1 wing domain polypeptide according to any of embodiments 1 to 7 in an in vitro diagnostic test for the detection of anti-flavivirus antibodies according to any of the methods of embodiments 8 to 23.

27. Use of a flavivirus NS1 wing domain polypeptide according to any of embodiment 25 to 26, wherein said flavivirus is selected from the group consisting of Zika virus (ZIKV), West-Nile virus (WNV), Dengue virus types 1-4 (DENV1-4), tick-borne encephalitis virus (TBEV), yellow fever virus (YFV), Japanese encephalitis virus (JEV), in an embodiment selected from the group consisting of Dengue virus types 1-4 (DENV1-4)

and West-Nile virus (WNV), in an embodiment wherein said flavivirus is Dengue virus types 1-4 (DENV1-4).

28. Use of a flavivirus NS1 wing domain polypeptide according to embodiment 27, wherein said NS1 wing domain specific amino acid sequence consists of a polypeptide selected from the group consisting of SEQ ID NOs. 1, 2, 5, 7, 9, 11, 13, 15, 17 and 19, in an embodiment selected from the group consisting of SEQ ID NOs. 7, 9, 11, 13 and 15, in an embodiment selected from the group consisting of SEQ ID NOs. 7, 9, 11 and 13 (NS1 domain of Dengue virus types 1-4).

29. A reagent kit for the detection of anti-flavivirus antibodies, comprising a flavivirus NS1 wing domain polypeptide according to any of embodiments 1 to 7, in an embodiment comprising instructions for use of said reagent kit.

30. A reagent kit according to embodiment 29 comprising in separate containers or in separated compartments of a single container unit at least microparticles coated with avidin or streptavidin, and a flavivirus NS1 wing domain polypeptide according to any of embodiments 1 to 7 that is covalently coupled to biotin.

31. A reagent kit according to embodiment 30 comprising in separate containers or in separated compartments of a single container unit at least microparticles coated with one partner of a bioaffine pair such as hapten/anti-hapten, and a polypeptide according to any of embodiments 1 to 7, wherein said bioaffine pair is hapten/anti-hapten, in an embodiment digoxin/anti-digoxin.

32. A reagent kit according to embodiment 29 additionally comprising a second polypeptide according to any of embodiments 1 to 7 that carries a detectable label.

33. A reagent kit according to embodiment 29, comprising in separate containers or in separated compartments of a single container unit at least microparticles coated with avidin or streptavidin, and a μ-capture binding partner that is covalently coupled to biotin.

34. A reagent kit according to embodiment 29, wherein said flavivirus NS1 wing domain polypeptide carries a detectable label.

35. A method for detecting antibodies against a first flavivirus in an isolated biological sample presumed to contain antibodies against at least one second flavivirus which is different from said first flavivirus, by using a flavivirus NS1 polypeptide comprising a complete or partial sequence of the ß-ladder domain as specific binding partner, wherein the cross-reactivity against at least one second flavivirus which is different from said first flavivirus is eliminated by adding a polypeptide comprising the NS1 ß-ladder domain of said flavivirus in unlabeled form, in an embodiment adding said polypeptide comprising the ß-ladder domain as a quencher.

36. Use of flavivirus NS1 ß-ladder domain polypeptide as a reagent for reducing interferences in an immunoassay for detecting anti-flavivirus antibodies.

37. Use according to embodiment 36, wherein said ß-ladder domain polypeptide is selected from the group consisting of SEQ ID NOs: SEQ ID NOs:4, 24, 25, 26 and 27.

The invention is further illustrated by the Examples.

Example 1: Immunological Reactivity (i.e., Antigenicity) of Different Zika NS1 Antigen Variants in a Zika IgG Immunoassay NS1 antigens and variants were essentially cloned, expressed, purified and labeled as described in WO2014054990A1 or by Scholz et al., J. Mol. Biol. (2005) 345, 1229-1241. The purified and solubilized gene products were subsequently coupled to either biotin or to an electrochemiluminescent ruthenium label.

The immunological reactivity (i.e., antigenicity) of the polypeptide fusion variants of Zika NS1 antigens was assessed in automated Elecsys® 2010 and cobas e 411 analyzers (Roche Diagnostics GmbH). Elecsys® is a registered trademark of the Roche group. Measurements were carried out in the double antigen sandwich format.

Signal detection in Elecsys® 2010 and cobas e 411 is based on electrochemiluminescence. The biotin-conjugate (i.e. the capture-antigen) is immobilized on the surface of a streptavidin coated magnetic bead whereas the detection-antigen bears a complexed Ruthenium cation (switching between the redox states 2+ and 3+) as the signaling moiety. In the presence of a specific immunoglobulin analyte, the chromogenic ruthenium complex is bridged to the solid phase and emits light at 620 nm after excitation at a platinum electrode. The signal output is in relative light units. Typically, the total duration of an assay is 18 minutes.

The recombinant Zika NS1 antigen fusion polypeptides were assessed in a double antigen sandwich (DAGS) immunoassay format. To this end, recombinant Zika NS1 antigen was used as a biotin and a ruthenium conjugate pair, respectively, to detect anti-Zika NS1 antibodies in human sera.

NS1 is one of the immunodominant antigens of Zika Virus, and soluble variants of NS1 antigen—as disclosed in this patent application—are invaluable tools for the detection of Zika virus infections. In all measurements, chemically polymerized and unlabeled SlyD-SlyD was implemented in large excess (~8 μg/ml) in the reaction buffer as anti-interference substances to avoid immunological cross reactions via the chaperone fusion and linker units.

In particular, two Zika NS1 variants were scrutinized in this study, namely the Zika NS1 "wing" domain (see SEQ ID NOs: 1 and 2) and the Zika NS1 "ß-ladder" domain (see SEQ ID NO:4). In order to detect anti-Zika NS1 IgG molecules, SlyD-SlyD-Zika NS1-biotin and SlyD-SlyD-Zika NS1-ruthenium were used in R1 (reagent buffer 1) and R2 (reagent buffer 2), respectively. The concentrations of the antigen conjugates in R1 and R2, respectively, were 500 ng/ml each.

Human serum samples negative for both Zika and Dengue IgG antibodies, human serum samples positive for Zika IgG antibodies and human serum samples positive for Dengue IgG antibodies were tested with both of the Zika NS1 recombinant antigens ("wing" and "ß-ladder") in comparison with a commercially available state of the art immuno assay (indirect ELISA applying a recombinant NS1 antigen coated to a microtiter plate, detection of the sample antibodies against Zika virus by addition of an enzyme-labeled anti-human IgG conjugate), as described by Huzly et al., supra.

In this experiment, the human samples described above were assessed with the aforementioned DAGS immunoassay setup.

The unavoidable system-inherent signal is around 500 counts. Low background signals for human serum samples negative for Zika IgG and Dengue IgG antibodies are indicative of high solubility and generally benign physicochemical properties of the respective antigen ruthenium conjugates. Hydrophobic or, generally spoken, "sticky" antigen-ruthenium conjugates tend to interact with the bead surface and thereby increase the background signal. From table 1 we can infer that the physicochemical properties of Zika NS1 "wing" are excellent (column 1). This holds true for Zika NS1 "ß-ladder" as well (data column 2): When Zika NS1 "wing" (SEQ ID NO:21) is used as an antigen pair in biotinylated form and in ruthenylated form in the DAGS format, or Zika NS1 "ß-ladder" (SEQ ID NO:22) is used as an antigen pair in biotinylated and ruthenylated form in the DAGS format, both antigen pairs yield a signal background of ~600-900 counts with negative human sera, which clearly points to good solubility properties of the antigen conjugates. However, it becomes evident at first glance that the Zika NS1 "wing" and the Zika NS1 "ß-ladder", although being equivalent in their capability to detect anti-Zika antibodies, largely differ in their cross-reactivity with anti-Dengue antibodies as shown in Table 1. Having a closer look at the Zika IgG positive samples, we find that both Zika NS1 "wing" and Zika NS1 "ß-ladder" detect all Zika IgG samples as positive (>2000 counts). Importantly, Zika NS1 "wing" does not cross-react with Dengue IgG positive samples, since all Dengue IgG samples are found negative (<<2000 counts) with the Zika NS1 wing antigen. In marked contrast, Zika NS1 "ß-ladder" detects 9 out of 20 Dengue IgG samples as reactive (>2000 counts), which points to a considerable degree of cross-reactivity. A very similar reactivity pattern with the Zika IgG and the Dengue IgG positive samples is observed with the commercially available Zika IgG assay described by Huzly et al. (Euro Surveill. 2016; 21(16), pii=30203, 1-4), indicating that the commercially available Zika IgG assay suffers from considerable immunological cross-reactivity (i.e., the commercially available Zika IgG assay provokes quite a few false positive Zika results) with Dengue IgG positive samples. In conclusion, both engineered variants of the Zika NS1 antigen (Zika NS1 "wing" and Zika NS1 "ß-ladder") possess outstanding physicochemical and antigenic properties. Yet, the Zika NS1 "wing" antigen outperforms the ß-ladder domain in that it displays superior specificity for Zika IgG antibodies and significantly reduced immunological cross reactivity with Dengue positive sera.

The engineered recombinant Zika NS1 "wing" domain therefore constitutes a superior NS1 variant for specific determination of Zika antibodies as compared to the state of the art commercially available Zika IgG immunoassay (which presumably is based on the full-length NS1) as described by Huzly et al., supra.

Table 1 shows the superior specificity (i.e., the strongly reduced cross-reactivity with anti-Dengue antibodies) of Zika NS1 "wing" as compared to Zika NS1 "ß-ladder" and commercially available state of the art Zika IgG assay.

TABLE 1

| Sample ID | Sample type | Zika NS1 "wing" assay counts | Signal dynamic | Zika NS1 "ß-ladder" assay counts | Signal dynamics* | Commercial Zika IgG assay s/co | Zika NS1 "wing" assay result | Zika NS1 "ß-ladder" assay result | Commercial Zika IgG assay result |
|---|---|---|---|---|---|---|---|---|---|
| BD03 | Negative 1 | 562 | 0.33 | 957 | 0.36 | 0.147 | NR | NR | NR |
| BD09 | Negative 2 | 549 | 0.33 | 975 | 0.37 | 0.018 | NR | NR | NR |
| BD15 | Negative 3 | 577 | 0.34 | 854 | 0.32 | 0.466 | NR | NR | NR |
| BD22 | Negative 4 | 559 | 0.33 | 874 | 0.33 | 0.056 | NR | NR | NR |
| BD23 | Negative 5 | 557 | 0.33 | 879 | 0.33 | 0.034 | NR | NR | NR |
| BD24 | Negative 6 | 567 | 0.34 | 869 | 0.33 | 0.050 | NR | NR | NR |
| BD29 | Negative 7 | 564 | 0.33 | 844 | 0.32 | 0.058 | NR | NR | NR |
| BD34 | Negative 8 | 575 | 0.34 | 971 | 0.37 | 0.028 | NR | NR | NR |
| BD36 | Negative 9 | 546 | 0.32 | 799 | 0.30 | 0.010 | NR | NR | NR |
| BD37 | Negative 10 | 558 | 0.33 | 823 | 0.31 | 0.054 | NR | NR | NR |
| ARSZ16052 | Zika IgG | 28556 | 16.95 | 80129 | 30.19 | 4.66 | reactive | reactive | reactive |
| ARSZ16244 | Zika IgG | 19906 | 11.82 | 10274 | 3.87 | 3.65 | reactive | reactive | reactive |
| 16CDV61200 | Zika IgG | 9157 | 5.44 | 113815 | 42.89 | 5.73 | reactive | reactive | reactive |
| ARSZ16245 | Zika IgG | 17990 | 10.68 | 22353 | 8.42 | 4.89 | reactive | reactive | reactive |
| 16CDV61275 | Zika IgG | 36305 | 21.56 | 241699 | 91.07 | 8.42 | reactive | reactive | reactive |
| ARSZ16271 | Zika IgG | 27026 | 16.05 | 117869 | 44.41 | 7.46 | reactive | reactive | reactive |
| ARSZ16264 | Zika IgG | 7260 | 4.31 | 45774 | 17.25 | 4.63 | reactive | reactive | reactive |
| ARSZ16178 | Zika IgG | 27957 | 16.60 | 241364 | 90.95 | 6.12 | reactive | reactive | reactive |
| ARSZ16013 | Zika IgG | 9658 | 5.73 | 178153 | 67.13 | 6.49 | reactive | reactive | reactive |
| ARSZ16062 | Zika IgG | 21206 | 12.59 | 269333 | 101.49 | 7.66 | reactive | reactive | reactive |
| 8DEN0016 | Dengue IgG | 555 | 0.33 | 604 | 0.23 | 0.050 | NR | NR | NR |
| 8DEN0008 | Dengue IgG | 558 | 0.33 | 616 | 0.23 | 0.213 | NR | NR | NR |
| 8DEN0040 | Dengue IgG | 560 | 0.33 | 574 | 0.22 | 0.089 | NR | NR | NR |
| 8DEN0015 | Dengue IgG | 564 | 0.33 | 596 | 0.22 | 0.066 | NR | NR | NR |
| 8DEN0017 | Dengue IgG | 564 | 0.33 | 588 | 0.22 | −0.019 | NR | NR | NR |
| 8DEN0045 | Dengue IgG | 568 | 0.34 | 584 | 0.22 | 0.112 | NR | NR | NR |
| D117 | Dengue IgG | 569 | 0.34 | 616 | 0.23 | 0.283 | NR | NR | NR |
| 8DEN0024 | Dengue IgG | 570 | 0.34 | 612 | 0.23 | 0.070 | NR | NR | NR |
| 8DEN0023 | Dengue IgG | 572 | 0.34 | 675 | 0.25 | 0.054 | NR | NR | NR |
| 8DEN0041 | Dengue IgG | 572 | 0.34 | 742 | 0.28 | 0.147 | NR | NR | NR |
| D092 | Dengue IgG | 566 | 0.34 | 4366 | 1.65 | 2.48 | NR | NR | NR |
| D096 | Dengue IgG | 567 | 0.34 | 4500 | 1.70 | 2.08 | NR | reactive | reactive |
| D009 | Dengue IgG | 574 | 0.34 | 19740 | 7.44 | 2.42 | NR | reactive | reactive |
| D094 | Dengue IgG | 577 | 0.34 | 2591 | 0.98 | 2.43 | NR | reactive | reactive |
| D109 | Dengue IgG | 583 | 0.35 | 9702 | 3.66 | 1.71 | NR | reactive | reactive |
| D099 | Dengue IgG | 585 | 0.35 | 3186 | 1.20 | 2.52 | NR | reactive | reactive |
| D102 | Dengue IgG | 585 | 0.35 | 13330 | 5.02 | 1.30 | NR | reactive | reactive |
| 8DEN0029 | Dengue IgG | 587 | 0.35 | 38740 | 14.60 | 3.62 | NR | reactive | reactive |
| 8DEN0013 | Dengue IgG | 595 | 0.35 | 37980 | 14.31 | 3.46 | NR | reactive | reactive |
| 8DEN0007 | Dengue IgG | 601 | 0.36 | 11840 | 4.46 | 3.06 | NR | reactive | reactive |

*Signal Dynamics = counts sample/((counts mean negative samples) × 3)
NR = non-reactive

Example 2: Blocking Experiment to Corroborate the Superior Specificity of the Zika NS1 "Wing" Antigen as Compared to Zika NS1 "ß-Ladder" Antigen The immunological reactivity (i.e., the antigenicity) of the polypeptide fusion variants of Zika NS1 antigens was assessed in automated Elecsys® 2010 and cobas e 411 analyzers (Roche Diagnostics GmbH) as described in Example 1.

Three human serum samples positive for Zika IgG antibodies were tested with both of the engineered Zika NS1 recombinant antigens ("wing" and "ß-ladder"). In parallel, these human serum samples positive for Zika IgG antibodies were individually spiked with full-length flavivirus NS1 antigen preparations of either TBEV (tick-borne encephalitis virus, FSME, SEQ ID NO:6), or one antigen of DENV1-4 (Dengue virus 1-4, SEQ ID NOs:8, 10, 12, 14), or WNV (West-Nile virus, SEQ ID NO: 16), or YFV (yellow fever virus, SEQ ID NO: 18), or JEV (Japanese encephalitis virus, SEQ ID NO:20) or ZIKV (Zika virus, SEQ ID NO:3) (tables 2a and 2b).

In this experiment, the human samples (spiked and unspiked) as described above were assessed with the aforementioned DAGS immunoassay setup.

Samples were pre-diluted to a reactivity level (titer) needed for the blocking experiment. This step was needed as the concentration of the flavivirus NS-1 preparations prepared for the blocking experiment and the amount of antibodies in the sample need to be within a reasonable concentration ratio in order to yield a clear blocking result. Then the reactivity of the pre-diluted human anti-Zika IgG positive sample was compared to the signals achieved with the same sample when spiked with full-length flavivirus NS-1 of either TBEV, or DENV1-4, or WNV, or YFV, or JEV or ZIKV. The extent of signal reduction due to competition by the different full-length flavivirus NS-1 preparations of TBEV, DENV1-4, WNV, YFV, JEV and ZIKV was calculated. The signal reduction/extent of blocking was normalized to the maximal blocking achieved with full length Zika NS1, which, as expected, shows the strongest quenching of the signal with both assays (irrespective of the use of either Zika NS1 "wing" or Zika NS1 "ß-ladder"). The degree of the capacity to compete was calculated for all other full-length flavivirus NS1 preparations (TBEV, DENV1-4, WNV, YFV, JEV). It is evident at first glance that the signal of the assay based on the Zika NS1 "wing" antigen is only weakly quenched by the non-Zika NS1 antigens, whereas the signal of the assay based on the Zika NS1 "ß-ladder" antigen is markedly reduced by TBEV, DENV1-4 and JEV. This finding compellingly indicates that the NS1 wing domain and the NS1 ß-ladder domain strongly differ in their structural uniqueness among the arboviral NS1 homologues. Obviously, the wing part of the non-Zika NS1 antigens is not able to efficiently compete with the engineered Zika wing antigen for binding to the anti-Zika analyte antibodies. Conversely, the ß-ladder part of the non-Zika NS1 antigens is perfectly able to efficiently compete with the engineered Zika ß-ladder antigen for binding to the anti-Zika analyte antibodies.

In conclusion, this experiment is perfectly in line with Example 1 as it also demonstrates that the assay based on Zika NS1 "wing" antigen largely detects those anti-Zika IgG antibodies, which are not cross-reactive (or prone to cross-reactivity) with flavivirus NS-1 preparations of other arboviruses (TBEV, DENV1-4, WNV, YFV, JEV). In contrast, the assay based on Zika NS1 "ß-ladder" antigen binds anti-Zika antibodies, which are, in part, cross-reactive (or prone to cross-reactivity) with TBEV, DENV1-4 and JEV (i.e., they can be blocked by TBEV, DENV1-4 and JEV NS-1 preparations). In other words, the ß-ladder domain of the Zika NS1 antigen seems to share significant structural and sequence homology with the ß-ladder domains of related arboviruses, thereby evoking false positive results in immunoassays when used as an antigen. In contrast, the wing domain of the Zika NS1 antigen seems to be rather unique and seems to share little structural homology with its NS counterparts from other arboviruses.

Our data indicate that this principle holds true not only in the discrimination of Zika virus infections from other flaviviral infections, but also in the discrimination of other flaviviral infections from each other. We conclude that the specific detection of antibodies against the wing domain of the NS1 antigen may be an excellent means to clearly distinguish flaviviral infections even on a multiple flaviviral infection background. We reason that our findings bear promise to markedly improve the current serology and to obtain a more appropriate view on prevalence and incidence data in the flavivirus field.

In summary, the Zika NS1 "wing" antigen displays outstanding and superior specificity for Zika IgG, is less susceptible to immunological cross-reactivity with antibodies raised against NS1 homologues from other arboviruses (here: family of flaviviruses) and is therefore much more suitable for specific testing for anti-Zika IgG antibodies.

TABLE 2a

| | SS-ZIKA-NS1-wing counts | S-ZIKA-NS1-ß-ladder counts | SS-ZIKA-NS1-wing Blocking [%] | S-ZIKA-NS1-ß-ladder Blocking [%] | SS-ZIKA-NS1-wing Normalized to Zika Blocking [%] | S-ZIKA-NS1-ß-ladder Normalized to Zika Blocking [%] |
|---|---|---|---|---|---|---|
| Sample 16CDV61275 | | | | | | |
| 1:10 pre-diluted | 3108 | 3432 | | | | |
| Spiked with ZIKV NS1 | 1225 | 947 | 76.3 | 92.0 | 100.0 | 100.0 |
| Spiked with TBEV NS1 | 3064 | 3387 | 1.73 | 1.62 | 2.3 | 1.8 |
| Spiked with DenV1 NS1 | 2946 | 1511 | 6.38 | 69.1 | 8.4 | 75.2 |
| Spiked with DenV2 NS1 | 3042 | 3349 | 2.60 | 2.99 | 3.4 | 3.2 |
| Spiked with DenV3 NS1 | 3014 | 1587 | 3.70 | 66.4 | 4.9 | 72.2 |
| Spiked with DenV4 NS1 | 3045 | 2734 | 2.48 | 25.1 | 3.3 | 27.3 |
| Sample 16CDV61278 | | | | | | |
| 1:20 pre-diluted | 2989 | 2887 | | | | |
| Spiked with ZIKV NS1 | 759 | 1457 | 91.7 | 69.4 | 100.0 | 100.0 |
| Spiked with TBEV NS1 | 2914 | 2911 | 3.10 | −1.07 | 3.4 | −1.5 |

TABLE 2a-continued

|  | SS-ZIKA-NS1-wing counts | S-ZIKA-NS1-ß-ladder counts | SS-ZIKA-NS1-wing Blocking [%] | S-ZIKA-NS1-ß-ladder Blocking [%] | SS-ZIKA-NS1-wing Normalized to Zika Blocking [%] | S-ZIKA-NS1-ß-ladder Normalized to Zika Blocking [%] |
|---|---|---|---|---|---|---|
| Spiked with DenV1 NS1 | 2858 | 1115 | 5.41 | 79.3 | 5.9 | 114.3 |
| Spiked with DenV2 NS1 | 2749 | 1423 | 9.91 | 65.5 | 10.8 | 94.4 |
| Spiked with DenV3 NS1 | 2783 | 1695 | 8.51 | 53.4 | 9.3 | 76.9 |
| Spiked with DenV4 NS1 | 2880 | 2829 | 4.50 | 2.60 | 4.9 | 3.7 |
| Sample 16CDV61197 |  |  |  |  |  |  |
| 1:10 pre-diluted | 2925 | 3089 |  |  |  |  |
| Spiked with ZIKV NS1 | 1127 | 1720 | 76.1 | 62.8 | 100.0 | 100.0 |
| Spiked with TBEV NS1 | 2897 | 3045 | 1.19 | 1.81 | 1.6 | 2.9 |
| Spiked with DenV1 NS1 | 2648 | 2073 | 11.7 | 41.7 | 15.4 | 66.4 |
| Spiked with DenV2 NS1 | 2682 | 2013 | 10.3 | 44.2 | 13.5 | 70.4 |
| Spiked with DenV3 NS1 | 2666 | 1911 | 11.0 | 48.4 | 14.4 | 77.0 |
| Spiked with DenV4 NS1 | 2904 | 2320 | 0.891 | 31.6 | 1.2 | 50.3 |

TABLE 2B

|  | SS-ZIKA-NS1-wing counts | S-ZIKA-NS1-ß-ladder counts | SS-ZIKA-NS1-wing Blocking [%] | S-ZIKA-NS1-ß-ladder Blocking [%] | SS-ZIKA-NS1-wing Normalized to Zika Blocking [%] | S-ZIKA-NS1-ß-ladder Normalized to Zika Blocking [%] |
|---|---|---|---|---|---|---|
| Sample 16CDV61275 |  |  |  |  |  |  |
| 1:10 pre-diluted | 3280 | 3486 |  |  |  |  |
| Spiked with ZIKV NS1 | 920 | 825 | 86.7 | 94.2 | 100.0 | 100.0 |
| Spiked with WNV NS1 | 2596 | 2154 | 25.1 | 47.1 | 29.0 | 50.1 |
| Spiked with YFV NS1 | 3154 | 3257 | 4.63 | 8.10 | 5.3 | 8.6 |
| Spiked with JEV NS1 | 3095 | 3198 | 6.80 | 10.2 | 7.8 | 10.8 |
| Sample 16CDV61278 |  |  |  |  |  |  |
| 1:20 pre-diluted | 2920 | 3314 |  |  |  |  |
| Spiked with ZIKV NS1 | 1098 | 1601 | 77.1 | 64.5 | 100.0 | 100.0 |
| Spiked with WNV NS1 | 2711 | 2477 | 8.85 | 31.5 | 11.5 | 48.9 |
| Spiked with YFV NS1 | 2651 | 3093 | 11.4 | 8.33 | 14.8 | 12.9 |
| Spiked with JEV NS1 | 2885 | 2835 | 1.48 | 18.0 | 1.9 | 28.0 |
| Sample 16CDV61197 |  |  |  |  |  |  |
| 1:10 pre-diluted | 2745 | 2989 |  |  |  |  |
| Spiked with ZIKV NS1 | 1403 | 1528 | 61.3 | 62.7 | 100.0 | 100.0 |
| Spiked with WNV NS1 | 2626 | 2551 | 5.44 | 18.8 | 8.9 | 30.0 |
| Spiked with YFV NS1 | 2664 | 2844 | 3.70 | 6.23 | 6.0 | 9.9 |
| Spiked with JEV NS1 | 2549 | 2704 | 8.96 | 12.2 | 14.6 | 19.5 |

EXPLANATION OF ACRONYMS

ZIKV=Zika virus
DENV1=Dengue Virus Type 1
DENV2=Dengue Virus Type 2
DENV3=Dengue Virus Type 3
DENV4=Dengue Virus Type 4
WNV=West Nile Virus
JEV=Japanese Encephalitis Virus
YFV=Yellow Fever Virus
TBEV=Tick Borne Encephalitis Virus (=FSME Virus)

Example 3: Immunological Reactivity of Dengue Virus NS1 Antigen Variants in a Dengue IgG Immunoassay Cloning, expression, purification and labeling of Dengue NS1 antigens and variants were performed essentially as in example 1. The immunological reactivity (i.e., antigenicity) of the polypeptide fusion variants of Dengue NS1 antigens was assessed in automated cobas e 601 analyzers (Roche Diagnostics GmbH). Elecsys® is a registered trademark of the Roche group. Measurements were carried out in the double antigen sandwich format, also described in example 1.

The recombinant Dengue NS1 antigen fusion polypeptides were assessed in a double antigen sandwich (DAGS) immunoassay format. To this end, recombinant Dengue NS1 antigen was used as a biotin and a ruthenium conjugate, respectively, to detect anti-Dengue NS1 antibodies in human sera.

In all measurements, chemically polymerized and unlabeled SlyD-SlyD was implemented in large excess (~8 μg/ml) in the reaction buffer as anti-interference substances to avoid immunological cross reactions via the chaperone fusion units.

In particular, two Dengue NS1 variants were examined in this study, namely the Dengue NS1 "wing" domain (see SEQ ID NOs:7, 9, 11 and 13 corresponding to DENV1-4) and the Dengue NS1 "ß-ladder" domain (see SEQ ID NOs:24 to 27, corresponding to DENV 1-4). In order to detect anti-Dengue NS1 IgG molecules, SlyD-SlyD-Dengue NS1-biotin and SlyD-SlyD-Dengue NS1-ruthenium were used in R1 (reagent buffer 1) and R2 (reagent buffer 2), respectively. The concentrations of the antigen conjugates in R1 and R2, respectively, were 500 ng/ml each. In preparations comprising antigens of all four Dengue serotypes the concentrations of the antigen conjugates in R1 and R2 were also 500 ng/ml each (2 µg/ml in total). As control and reference the Zika IgG assay of example 1 containing the Zika NS1 wing domain as antigen was used.

Human serum samples negative for both, Zika and Dengue IgG antibodies, human serum samples positive for Dengue IgG antibodies and human serum samples positive for Zika IgG antibodies were tested with Dengue NS1 recombinant antigens derived from all four dengue serotypes for "wing" and derived from DENV2 for "ß-ladder".

In this experiment, the human samples described above were assessed with the aforementioned DAGS immunoassay setup. Table 3 shows the results.

It could be shown that the NS1 wing domain of all four Dengue virus serotypes can be overexpressed in E. coli and that these recombinant antigens can be obtained in high yield. The antigens can be refolded into a soluble native-like and immunoreactive conformation after purification. It could be shown that sera pre-tested as Dengue positive by an immunofluorescence assay were correctly identified as positive in our assay set-up. DENV1-4 wing domain and DENV2 ß-ladder domain indeed do react with the presumably Dengue-positive sera. However, we found evidence that the individual Dengue wing domains of DENV 1-4 react differently with the pre-characterized commercial set of Dengue-positive sera. The results seem to indicate that an immunological differentiation of the Dengue virus serotypes may be possible on the basis of the Dengue NS1 wing domain as an antigen in an immunoassay.

Moreover, the Zika IgG assay of example 1 using the Zika NS1 wing domain as specific antigen does not show any cross-reactivities with the pre-characterized commercial set of Dengue antibody positive sera, underlining once more the excellent specificity of the Zika NS1 wing domain. Most interestingly, the Zika positive sera exclusively react with the Zika NS1 wing domain but do not cross-react with any of the Dengue wing domain antigens. In other words, the Dengue wing domains also hold promise as highly specific antigens in populations that exhibit a high prevalence of multiple flaviviral infections. It is one thing to reliably detect a Dengue infection in a suspected central European returning from a holiday in, e.g., Brazil or Thailand. It is a completely different thing to reliably detect a Dengue infection in a patient that has a medical background of, e.g., previous yellow fever and/or Zika infections in a high-prevalence region. It is therefore especially for emerging countries with high prevalence of multiple flaviviral infections that the specificity of Flavivirus immunoassays is of paramount importance. Our results indicate that the flaviviral NS1 wing domain is an excellent tool for specific detection of antibodies against the flavivirus the wing domain of which is applied as a binding partner in an immunoassay.

TABLE 3

| sample ID | Pre-characterization | Zika NS1 Wing counts | Zika NS1 Wing signal dynamics | DENV1-NS1Wing counts | DENV1-NS1Wing signal dynamics | DENV2-NS1Wing counts | DENV2-NS1Wing signal dynamics |
|---|---|---|---|---|---|---|---|
| Zika_Cal1 | ZikV negative | 796 | 0.98 | 3488 | 0.99 | 642 | 0.95 |
| Zika_Cal2 | ZikV positive | 16553 | 20.39 | 4646 | 1.32 | 779 | 1.16 |
| Zika_Ctr1 | ZikV negative | 788 | 0.97 | 3512 | 1.00 | 651 | 0.97 |
| Zika_Ctr2 | ZikV positive | 11758 | 14.48 | 5279 | 1.50 | 863 | 1.28 |
| 23495200 | ZikV/DenV negative | 782 | 0.96 | 3435 | 0.98 | 653 | 0.97 |
| 22053300 | ZikV/DenV negative | 825 | 1.02 | 3474 | 0.99 | 659 | 0.98 |
| 22053400 | ZikV/DenV negative | 801 | 0.99 | 3656 | 1.04 | 722 | 1.07 |
| 23495400 | ZikV/DenV negative | 840 | 1.03 | 3504 | 1.00 | 662 | 0.98 |
| Panel_Member01 | DENV1 + DENV2 | 1071 | 1.32 | 129359 | 36.78 | 26539 | 39.39 |
| Panel_Member02 | negative | 797 | 0.98 | 3605 | 1.03 | 639 | 0.95 |
| Panel_Member03 | DENV1 + DENV2 | 1063 | 1.31 | 125859 | 35.79 | 23799 | 35.32 |
| Panel_Member04 | DENV1 + DENV2 | 791 | 0.97 | 9812 | 2.79 | 29263 | 43.43 |
| Panel_Member05 | DENV1 + DENV2 | 804 | 0.99 | 8427 | 2.40 | 21884 | 32.48 |
| Panel_Member06 | DENV2 + DENV3 | 824 | 1.01 | 7540 | 2.14 | 17969 | 26.67 |
| Panel_Member07 | DENV1 + DENV2 | 816 | 1.00 | 6937 | 1.97 | 14883 | 22.09 |
| Panel_Member08 | negative | 821 | 1.01 | 3404 | 0.97 | 635 | 0.94 |
| Panel_Member09 | DENV1 + DENV2 | 821 | 1.01 | 6322 | 1.80 | 12743 | 18.91 |
| Panel_Member10 | DENV2 + DENV3 | 844 | 1.04 | 5828 | 1.66 | 10759 | 15.97 |

| sample ID | DENV2-NS1 ß-Ladder counts | DENV2-NS1 ß-Ladder signal dynamics | DENV3-NS1Wing counts | DENV3-NS1Wing signal dynamics | DENV4-NS1Wing counts | DENV4-NS1Wing signal dynamics |
|---|---|---|---|---|---|---|
| Zika_Cal1 | nd | nd | 3566 | 1.12 | 1627 | 1.07 |
| Zika_Cal2 | nd | nd | 8252 | 2.59 | 4411 | 2.89 |
| Zika_Ctr1 | nd | nd | 3555 | 1.12 | 1630 | 1.07 |
| Zika_Ctr2 | nd | nd | 9229 | 2.90 | 4063 | 2.67 |
| 23495200 | 470 | 0.82 | 2986 | 0.94 | 1508 | 0.99 |
| 22053300 | 472 | 0.83 | 3415 | 1.07 | 1515 | 0.99 |
| 22053400 | 599 | 1.05 | 3301 | 1.04 | 1527 | 1.00 |
| 23495400 | 740 | 1.30 | 3044 | 0.96 | 1547 | 1.01 |
| Panel_Member01 | 21145 | 37.10 | 937557 | 294.26 | 10418 | 6.84 |
| Panel_Member02 | 469 | 0.82 | 3488 | 1.09 | 1614 | 1.06 |
| Panel_Member03 | 23389 | 41.03 | 876002 | 274.94 | 9778 | 6.42 |

TABLE 3-continued

| | | | | | | |
|---|---|---|---|---|---|---|
| Panel_Member04 | 57286 | 100.50 | 6980 | 2.19 | 27612 | 18.12 |
| Panel_Member05 | 52546 | 92.19 | 6223 | 1.95 | 21911 | 14.38 |
| Panel_Member06 | 49717 | 87.22 | 5819 | 1.83 | 18810 | 12.34 |
| Panel_Member07 | 46787 | 82.08 | 5299 | 1.66 | 15917 | 10.45 |
| Panel_Member08 | 455 | 0.80 | 3429 | 1.08 | 1603 | 1.05 |
| Panel_Member09 | 44023 | 77.23 | 5346 | 1.68 | 14006 | 9.19 |
| Panel_Member10 | 41559 | 72.91 | 4876 | 1.53 | 11956 | 7.85 |

Dengue positive human sera marked with Panel_Member were purchased from ZeptoMetrix (Catalog# KZMC028);
the pre-characterization of these commercial sera is based on an immunofluorescence test;
nd: not determined;
Zika_Cal1 and Cal2: negative and positive calibrator of Zika IgG assay of example 1;
Zika_Ctr1 and Ctr2: negative and positive control of Zika IgG assay of example 1

---

The invention claimed is:

1. A polypeptide suitable for detecting antibodies against a flavivirus in an isolated biological sample comprising a flavivirus NS1 wing domain specific amino acid sequence, wherein no amino acid sequences from the NS1 β-ladder domain of said flavivirus are present in said polypeptide, wherein said polypeptide is fused to a chaperone.

2. A polypeptide according to claim 1, wherein no further amino acid sequences of said flavivirus are present in said polypeptide.

3. A polypeptide according to claim 1, wherein said flavivirus is selected from the group consisting of Zika virus (ZIKV), West-Nile virus (WNV), Dengue virus types 1-4 (DENV1-4), tick-borne encephalitis virus (TBEV), yellow fever virus (YFV), and Japanese encephalitis virus (JEV).

4. A polypeptide according to claim 1, wherein said flavivirus NS1 wing domain specific amino acid sequence comprises a polypeptide selected from the group consisting of SEQ ID NOs. 1, 2, 5, 7, 9, 11, 13, 15, 17 and 19.

5. A polypeptide according to claim 1, wherein said chaperone is selected from the group consisting of SlyD, SlpA, FkpA and Skp.

6. A polypeptide according to claim 5, selected from the group consisting of SEQ ID NOs.: 21 (Zika), 28 (DENV1), 29 (DENV2), 30 (DENV3) and 31 (DENV4).

7. A method of producing a soluble and immunoreactive flavivirus NS1 wing domain polypeptide, said method comprising the steps of
   a) culturing host cells transformed with an expression vector comprising operably linked a recombinant DNA molecule encoding a flavivirus NS1 wing domain polypeptide according to claim 1,
b) expression of said flavivirus NS1 wing domain polypeptide and
c) purification of said flavivirus NS1 wing domain polypeptide.

8. A method for detecting antibodies specific for a first flavivirus species in an isolated sample said method comprising
a) forming an immunoreaction admixture by admixing a body fluid sample with a flavivirus NS1 wing domain polypeptide of said first flavivirus species according to claim 1;
b) maintaining said immunoreaction admixture for a time period sufficient for allowing antibodies present in the body fluid sample against said flavivirus NS1 wing domain polypeptide to immunoreact with said flavivirus NS1 wing domain polypeptide to form an immunoreaction product; and
c) detecting the presence and/or the concentration of any of said immunoreaction product.

9. A method for detecting antibodies specific for a first flavivirus species in an isolated sample according to claim 8, wherein the detected antibody is an IgG or IgM antibody.

10. A method for detecting antibodies specific for a first flavivirus species in an isolated sample according to claim 8 wherein said first flavivirus species is Dengue virus types 1 to 4.

* * * * *

SEQUENCE LISTING

<160> NUMBER OF SEQ ID NOS: 35

<210> SEQ ID NO 1
<211> LENGTH: 151
<212> TYPE: PRT
<213> ORGANISM: Artificial
<220> FEATURE:
<223> OTHER INFORMATION: Zika virus NS1 wing domain aa 30-180 with
      position 179 X = A or S or C
<220> FEATURE:
<221> NAME/KEY: misc_feature
<222> LOCATION: (150)..(150)
<223> OTHER INFORMATION: Xaa can be Ala or Ser or Cys

<400> SEQUENCE: 1

Asp Arg Tyr Lys Tyr His Pro Asp Ser Pro Arg Arg Leu Ala Ala Ala
1               5                   10                  15

Val Lys Gln Ala Trp Glu Glu Gly Ile Cys Gly Ile Ser Ser Val Ser
            20                  25                  30

Arg Met Glu Asn Ile Met Trp Lys Ser Val Glu Gly Glu Leu Asn Ala
        35                  40                  45

Ile Leu Glu Glu Asn Gly Val Gln Leu Thr Val Val Val Gly Ser Val
    50                  55                  60

Lys Asn Pro Met Trp Arg Gly Pro Gln Arg Leu Pro Val Pro Val Asn
65                  70                  75                  80

Glu Leu Pro His Gly Trp Lys Ala Trp Gly Lys Ser Tyr Phe Val Arg
                85                  90                  95

Ala Ala Lys Thr Asn Asn Ser Phe Val Val Asp Gly Asp Thr Leu Lys
            100                 105                 110

Glu Cys Pro Leu Lys His Arg Ala Trp Asn Ser Phe Leu Val Glu Asp
        115                 120                 125

His Gly Phe Gly Val Phe His Thr Ser Val Trp Leu Lys Val Arg Glu
    130                 135                 140

Asp Tyr Ser Leu Glu Xaa Asp
145                 150

<210> SEQ ID NO 2
<211> LENGTH: 151
<212> TYPE: PRT
<213> ORGANISM: Artificial
<220> FEATURE:
<223> OTHER INFORMATION: Zika virus NS1 wing domain aa 30-180 with C55,
      C143, C179A

<400> SEQUENCE: 2

Asp Arg Tyr Lys Tyr His Pro Asp Ser Pro Arg Arg Leu Ala Ala Ala
1               5                   10                  15

```
Val Lys Gln Ala Trp Glu Glu Gly Ile Cys Gly Ile Ser Ser Val Ser
                20                  25                  30

Arg Met Glu Asn Ile Met Trp Lys Ser Val Glu Gly Glu Leu Asn Ala
            35                  40                  45

Ile Leu Glu Glu Asn Gly Val Gln Leu Thr Val Val Gly Ser Val
    50                  55                  60

Lys Asn Pro Met Trp Arg Gly Pro Gln Arg Leu Pro Val Pro Val Asn
65                  70                  75                  80

Glu Leu Pro His Gly Trp Lys Ala Trp Gly Lys Ser Tyr Phe Val Arg
                85                  90                  95

Ala Ala Lys Thr Asn Asn Ser Phe Val Val Asp Gly Asp Thr Leu Lys
            100                 105                 110

Glu Cys Pro Leu Lys His Arg Ala Trp Asn Ser Phe Leu Val Glu Asp
        115                 120                 125

His Gly Phe Gly Val Phe His Thr Ser Val Trp Leu Lys Val Arg Glu
130                 135                 140

Asp Tyr Ser Leu Glu Ala Asp
145                 150
```

<210> SEQ ID NO 3
<211> LENGTH: 352
<212> TYPE: PRT
<213> ORGANISM: Zika virus

<400> SEQUENCE: 3

```
Asp Val Gly Cys Ser Val Asp Phe Ser Lys Arg Glu Thr Arg Cys Gly
1               5                   10                  15

Thr Gly Val Phe Ile Tyr Asn Asp Val Glu Ala Trp Arg Asp Arg Tyr
                20                  25                  30

Lys Tyr His Pro Asp Ser Pro Arg Arg Leu Ala Ala Ala Val Lys Gln
            35                  40                  45

Ala Trp Glu Glu Gly Ile Cys Gly Ile Ser Ser Val Ser Arg Met Glu
        50                  55                  60

Asn Ile Met Trp Lys Ser Val Glu Gly Glu Leu Asn Ala Ile Leu Glu
65                  70                  75                  80

Glu Asn Gly Val Gln Leu Thr Val Val Gly Ser Val Lys Asn Pro
                85                  90                  95

Met Trp Arg Gly Pro Gln Arg Leu Pro Val Pro Val Asn Gly Leu Pro
            100                 105                 110

His Gly Trp Lys Ala Trp Gly Lys Ser Tyr Phe Val Arg Ala Ala Lys
        115                 120                 125

Thr Asn Asn Ser Phe Val Val Asp Gly Asp Thr Leu Lys Glu Cys Pro
130                 135                 140

Leu Lys His Arg Ala Trp Asn Ser Phe Leu Val Glu Asp His Gly Phe
145                 150                 155                 160

Gly Val Phe His Thr Ser Val Trp Leu Lys Val Arg Glu Asp Tyr Ser
                165                 170                 175

Leu Glu Cys Asp Pro Ala Val Ile Gly Thr Ala Val Lys Gly Arg Glu
            180                 185                 190

Ala Ala His Ser Asp Leu Gly Tyr Trp Ile Glu Ser Glu Lys Asn Asp
        195                 200                 205

Thr Trp Arg Leu Lys Arg Ala His Leu Ile Glu Met Lys Thr Cys Glu
210                 215                 220

Trp Pro Lys Ser His Thr Leu Trp Thr Asp Gly Val Glu Glu Ser Asp
225                 230                 235                 240
```

-continued

Leu Ile Ile Pro Lys Ser Leu Ala Gly Pro Leu Ser His His Asn Thr
            245                 250                 255

Arg Glu Gly Tyr Arg Thr Gln Val Lys Gly Pro Trp His Ser Glu Glu
        260                 265                 270

Leu Glu Ile Arg Phe Glu Glu Cys Pro Gly Thr Lys Val His Val Glu
        275                 280                 285

Glu Thr Cys Gly Thr Arg Gly Pro Ser Leu Arg Ser Thr Thr Ala Ser
    290                 295                 300

Gly Arg Val Ile Glu Glu Trp Cys Cys Arg Glu Cys Thr Met Pro Pro
305                 310                 315                 320

Leu Ser Phe Arg Ala Lys Asp Gly Cys Trp Tyr Gly Met Glu Ile Arg
                325                 330                 335

Pro Arg Lys Glu Pro Glu Ser Asn Leu Val Arg Ser Met Val Thr Ala
            340                 345                 350

<210> SEQ ID NO 4
<211> LENGTH: 162
<212> TYPE: PRT
<213> ORGANISM: Zika virus

<400> SEQUENCE: 4

Arg Glu Ala Ala His Ser Asp Leu Gly Tyr Trp Ile Glu Ser Glu Lys
1               5                   10                  15

Asn Asp Thr Trp Arg Leu Lys Arg Ala His Leu Ile Glu Met Lys Thr
            20                  25                  30

Cys Glu Trp Pro Lys Ser His Thr Leu Trp Thr Asp Gly Val Glu Glu
        35                  40                  45

Ser Asp Leu Ile Ile Pro Lys Ser Leu Ala Gly Pro Leu Ser His His
    50                  55                  60

Asn Thr Arg Glu Gly Tyr Arg Thr Gln Val Lys Gly Pro Trp His Ser
65                  70                  75                  80

Glu Glu Leu Glu Ile Arg Phe Glu Glu Cys Pro Gly Thr Lys Val His
                85                  90                  95

Val Glu Glu Thr Cys Gly Thr Arg Gly Pro Ser Leu Arg Ser Thr Thr
            100                 105                 110

Ala Ser Gly Arg Val Ile Glu Glu Trp Cys Cys Arg Glu Cys Thr Met
        115                 120                 125

Pro Pro Leu Ser Phe Arg Ala Lys Asp Gly Cys Trp Tyr Gly Met Glu
    130                 135                 140

Ile Arg Pro Arg Lys Glu Pro Glu Ser Asn Leu Val Arg Ser Met Val
145                 150                 155                 160

Thr Ala

<210> SEQ ID NO 5
<211> LENGTH: 151
<212> TYPE: PRT
<213> ORGANISM: Artificial
<220> FEATURE:
<223> OTHER INFORMATION: Tick-borne encephalitis (FSME) virus NS1 wing
      domain aa 30-180 according to UniProt ID P14336; European subtype
      strain Neudoerfl; X = A or C or S
<220> FEATURE:
<221> NAME/KEY: misc_feature
<222> LOCATION: (150)..(150)
<223> OTHER INFORMATION: Xaa can be Ala or Ser or Cys

<400> SEQUENCE: 5

Asp Asn Tyr Ala Tyr Tyr Pro Glu Thr Pro Gly Ala Leu Ala Ser Ala

```
 1               5                  10                 15
Ile Lys Glu Thr Phe Glu Glu Gly Ser Cys Gly Val Val Pro Gln Asn
             20                 25                 30

Arg Leu Glu Met Ala Met Trp Arg Ser Ser Val Thr Glu Leu Asn Leu
             35                 40                 45

Ala Leu Ala Glu Gly Glu Ala Asn Leu Thr Val Val Asp Lys Phe
 50                 55                 60

Asp Pro Thr Asp Tyr Arg Gly Val Pro Gly Leu Leu Lys Lys Gly
 65              70                 75                 80

Lys Asp Ile Lys Val Ser Trp Lys Ser Trp Gly His Ser Met Ile Trp
                 85                 90                 95

Ser Ile Pro Glu Ala Pro Arg Arg Phe Met Val Gly Thr Glu Gly Gln
             100                105                110

Ser Glu Cys Pro Leu Glu Arg Arg Lys Thr Gly Val Phe Thr Val Ala
             115                120                125

Glu Phe Gly Val Gly Leu Arg Thr Lys Val Phe Leu Asp Phe Arg Gln
             130                135                140

Glu Pro Thr His Glu Xaa Asp
145                 150
```

<210> SEQ ID NO 6
<211> LENGTH: 352
<212> TYPE: PRT
<213> ORGANISM: Tick-borne encephalitis virus

<400> SEQUENCE: 6

```
Asp Val Gly Cys Ala Val Asp Thr Glu Arg Met Glu Leu Arg Cys Gly
 1               5                  10                 15

Glu Gly Leu Val Val Trp Arg Glu Val Ser Glu Trp Tyr Asp Asn Tyr
             20                 25                 30

Ala Tyr Tyr Pro Glu Thr Pro Gly Ala Leu Ala Ser Ala Ile Lys Glu
             35                 40                 45

Thr Phe Glu Glu Gly Ser Cys Gly Val Val Pro Gln Asn Arg Leu Glu
 50                 55                 60

Met Ala Met Trp Arg Ser Ser Val Thr Glu Leu Asn Leu Ala Leu Ala
 65              70                 75                 80

Glu Gly Glu Ala Asn Leu Thr Val Val Asp Lys Phe Asp Pro Thr
                 85                 90                 95

Asp Tyr Arg Gly Val Pro Gly Leu Leu Lys Lys Gly Lys Asp Ile
             100                105                110

Lys Val Ser Trp Lys Ser Trp Gly His Ser Met Ile Trp Ser Ile Pro
             115                120                125

Glu Ala Pro Arg Arg Phe Met Val Gly Thr Glu Gly Gln Ser Glu Cys
             130                135                140

Pro Leu Glu Arg Arg Lys Thr Gly Val Phe Thr Val Ala Glu Phe Gly
145                 150                155                160

Val Gly Leu Arg Thr Lys Val Phe Leu Asp Phe Arg Gln Glu Pro Thr
                 165                170                175

His Glu Cys Asp Thr Gly Val Met Gly Ala Ala Val Lys Asn Gly Met
             180                185                190

Ala Ile His Thr Asp Gln Ser Leu Trp Met Arg Ser Met Lys Asn Asp
             195                200                205

Thr Gly Thr Tyr Ile Val Glu Leu Leu Val Thr Asp Leu Arg Asn Cys
             210                215                220
```

```
Ser Trp Pro Ala Ser His Thr Ile Asp Asn Ala Asp Val Val Asp Ser
225                 230                 235                 240

Glu Leu Phe Leu Pro Ala Ser Leu Ala Gly Pro Arg Ser Trp Tyr Asn
            245                 250                 255

Arg Ile Pro Gly Tyr Ser Glu Gln Val Lys Gly Pro Trp Lys Tyr Thr
        260                 265                 270

Pro Ile Arg Val Ile Arg Glu Glu Cys Pro Gly Thr Thr Val Thr Ile
    275                 280                 285

Asn Ala Lys Cys Asp Lys Arg Gly Ala Ser Val Arg Ser Thr Thr Glu
290                 295                 300

Ser Gly Lys Val Ile Pro Glu Trp Cys Cys Arg Ala Cys Thr Met Pro
305                 310                 315                 320

Pro Val Thr Phe Arg Thr Gly Thr Asp Cys Trp Tyr Ala Met Glu Ile
            325                 330                 335

Arg Pro Val His Asp Gln Gly Leu Val Arg Ser Met Val Val Ala
        340                 345                 350

<210> SEQ ID NO 7
<211> LENGTH: 151
<212> TYPE: PRT
<213> ORGANISM: Artificial
<220> FEATURE:
<223> OTHER INFORMATION: Dengue virus type 1 NS1 wing domain aa 30-180;
      X = A or C or S
<220> FEATURE:
<221> NAME/KEY: misc_feature
<222> LOCATION: (150)..(150)
<223> OTHER INFORMATION: Xaa can be Ala or Ser or Cys

<400> SEQUENCE: 7

Glu Gln Tyr Lys Phe Gln Ala Asp Ser Pro Lys Arg Leu Ser Ala Ala
1               5                   10                  15

Ile Gly Lys Ala Trp Glu Glu Gly Val Cys Gly Ile Arg Ser Ala Thr
            20                  25                  30

Arg Leu Glu Asn Ile Met Trp Lys Gln Ile Ser Asn Glu Leu Asn His
        35                  40                  45

Ile Leu Leu Glu Asn Asp Met Lys Phe Thr Val Val Val Gly Asp Val
    50                  55                  60

Ala Gly Ile Leu Ala Gln Gly Lys Lys Met Ile Arg Pro Gln Pro Met
65                  70                  75                  80

Glu His Lys Tyr Ser Trp Lys Ser Trp Gly Lys Ala Lys Ile Ile Gly
                85                  90                  95

Ala Asp Val Gln Asn Thr Thr Phe Ile Ile Asp Gly Pro Asn Thr Pro
            100                 105                 110

Glu Cys Pro Asp Asp Gln Arg Ala Trp Asn Ile Trp Glu Val Glu Asp
        115                 120                 125

Tyr Gly Phe Gly Ile Phe Thr Thr Asn Ile Trp Leu Lys Leu Arg Asp
    130                 135                 140

Ser Tyr Thr Gln Val Xaa Asp
145                 150

<210> SEQ ID NO 8
<211> LENGTH: 352
<212> TYPE: PRT
<213> ORGANISM: Dengue virus type 1

<400> SEQUENCE: 8

Asp Ser Gly Cys Val Ile Asn Trp Lys Gly Arg Glu Leu Lys Cys Gly
1               5                   10                  15
```

Ser Gly Ile Phe Val Thr Asn Glu Val His Thr Trp Thr Glu Gln Tyr
            20                  25                  30

Lys Phe Gln Ala Asp Ser Pro Lys Arg Leu Ser Ala Ala Ile Gly Lys
        35                  40                  45

Ala Trp Glu Glu Gly Val Cys Gly Ile Arg Ser Ala Thr Arg Leu Glu
50                  55                  60

Asn Ile Met Trp Lys Gln Ile Ser Asn Glu Leu Asn His Ile Leu Leu
65                  70                  75                  80

Glu Asn Gly Met Lys Phe Thr Val Val Gly Val Glu Val Asn Gly Ile
                85                  90                  95

Leu Ala Gln Gly Lys Lys Met Ile Arg Pro Gln Pro Met Glu His Lys
            100                 105                 110

Tyr Ser Trp Lys Ser Trp Gly Lys Ala Lys Val Ile Gly Ala Asp Val
        115                 120                 125

Gln Asn Thr Thr Phe Ile Ile Asp Gly Pro Asn Thr Pro Glu Cys Pro
130                 135                 140

Asp Asp Gln Arg Ala Trp Asn Ile Trp Glu Val Glu Asp Tyr Gly Phe
145                 150                 155                 160

Gly Ile Phe Thr Thr Asn Ile Trp Leu Lys Leu Arg Asp Ser Tyr Thr
                165                 170                 175

Gln Val Cys Asp His Arg Leu Met Ser Ala Ala Ile Lys Asp Ser Lys
            180                 185                 190

Ala Val His Ala Asp Met Gly Tyr Trp Ile Glu Ser Glu Lys Asn Glu
        195                 200                 205

Thr Trp Lys Leu Ala Arg Ala Ser Phe Ile Glu Val Lys Thr Cys Ile
210                 215                 220

Trp Pro Lys Ser His Thr Leu Trp Ser Asn Gly Val Leu Glu Ser Glu
225                 230                 235                 240

Met Ile Ile Pro Lys Ile Tyr Gly Gly Pro Ile Ser Gln His Asn Tyr
                245                 250                 255

Arg Pro Gly Tyr Phe Thr Gln Thr Ala Gly Pro Trp His Leu Gly Lys
            260                 265                 270

Leu Glu Leu Asp Phe Glu Leu Cys Glu Gly Thr Thr Val Val Val Asp
        275                 280                 285

Glu His Cys Gly Asn Arg Gly Pro Ser Leu Arg Thr Thr Thr Val Thr
290                 295                 300

Gly Lys Ile Ile His Glu Trp Cys Cys Arg Ser Cys Thr Leu Pro Pro
305                 310                 315                 320

Leu Arg Phe Lys Gly Glu Asp Gly Cys Trp Tyr Gly Met Glu Ile Arg
                325                 330                 335

Pro Val Lys Glu Lys Glu Glu Asn Leu Val Lys Ser Met Val Ser Ala
            340                 345                 350

<210> SEQ ID NO 9
<211> LENGTH: 151
<212> TYPE: PRT
<213> ORGANISM: Artificial
<220> FEATURE:
<223> OTHER INFORMATION: Dengue virus type 2 NS1 wing domain aa 30-180;
      X = A or C or S
<220> FEATURE:
<221> NAME/KEY: misc_feature
<222> LOCATION: (150)..(150)
<223> OTHER INFORMATION: Xaa can be Ala or Ser or Cys

<400> SEQUENCE: 9

```
Glu Gln Tyr Lys Phe Gln Pro Glu Ser Pro Ser Lys Leu Ala Ser Ala
1               5                   10                  15

Ile Gln Lys Ala His Glu Glu Gly Ile Cys Gly Ile Arg Ser Val Thr
            20                  25                  30

Arg Leu Glu Asn Leu Met Trp Lys Gln Ile Thr Pro Glu Leu Asn His
        35                  40                  45

Ile Leu Ser Glu Asn Glu Val Lys Leu Thr Ile Met Thr Gly Asp Ile
50                  55                  60

Lys Gly Ile Met Gln Ala Gly Lys Arg Ser Leu Arg Pro Gln Pro Thr
65                  70                  75                  80

Glu Leu Lys Tyr Ser Trp Lys Thr Trp Gly Lys Ala Lys Met Leu Ser
                85                  90                  95

Thr Glu Ser His Asn Gln Thr Phe Leu Ile Asp Gly Pro Glu Thr Ala
                100                 105                 110

Glu Cys Pro Asn Thr Asn Arg Ala Trp Asn Ser Leu Glu Val Glu Asp
                115                 120                 125

Tyr Gly Phe Gly Val Phe Thr Thr Asn Ile Trp Leu Lys Leu Lys Glu
            130                 135                 140

Lys Gln Asp Val Phe Xaa Asp
145                 150

<210> SEQ ID NO 10
<211> LENGTH: 352
<212> TYPE: PRT
<213> ORGANISM: Dengue virus type 2

<400> SEQUENCE: 10

Asp Ser Gly Cys Val Val Ser Trp Lys Asn Lys Glu Leu Lys Cys Gly
1               5                   10                  15

Ser Gly Ile Phe Ile Thr Asp Asn Val His Thr Trp Thr Glu Gln Tyr
            20                  25                  30

Lys Phe Gln Pro Glu Ser Pro Ser Lys Leu Ala Ser Ala Ile Gln Lys
        35                  40                  45

Ala His Glu Glu Gly Ile Cys Gly Ile Arg Ser Val Thr Arg Leu Glu
50                  55                  60

Asn Leu Met Trp Lys Gln Ile Thr Pro Glu Leu Asn His Ile Leu Ser
65                  70                  75                  80

Glu Asn Glu Val Lys Leu Thr Ile Met Thr Gly Asp Ile Lys Gly Ile
                85                  90                  95

Met Gln Ala Gly Lys Arg Ser Leu Arg Pro Gln Pro Thr Glu Leu Lys
                100                 105                 110

Tyr Ser Trp Lys Thr Trp Gly Lys Ala Lys Met Leu Ser Thr Glu Ser
            115                 120                 125

His Asn Gln Thr Phe Leu Ile Asp Gly Pro Glu Thr Ala Glu Cys Pro
130                 135                 140

Asn Thr Asn Arg Ala Trp Asn Ser Leu Glu Val Glu Asp Tyr Gly Phe
145                 150                 155                 160

Gly Val Phe Thr Thr Asn Ile Trp Leu Lys Leu Lys Glu Lys Gln Asp
                165                 170                 175

Val Phe Cys Asp Ser Lys Leu Met Ser Ala Ala Ile Lys Asp Asn Arg
                180                 185                 190

Ala Val His Ala Asp Met Gly Tyr Trp Ile Glu Ser Ala Leu Asn Asp
            195                 200                 205

Thr Trp Lys Ile Glu Lys Ala Ser Phe Ile Glu Val Lys Asn Cys His
210                 215                 220
```

-continued

```
Trp Pro Lys Ser His Thr Leu Trp Ser Asn Gly Val Leu Glu Ser Glu
225                 230                 235                 240

Met Ile Ile Pro Lys Asn Leu Ala Gly Pro Val Ser Gln His Asn Tyr
                245                 250                 255

Arg Pro Gly Tyr His Thr Gln Ile Thr Gly Pro Trp His Leu Gly Lys
            260                 265                 270

Leu Glu Met Asp Phe Asp Phe Cys Asp Gly Thr Thr Val Val Val Thr
        275                 280                 285

Glu Asp Cys Gly Asn Arg Gly Pro Ser Leu Arg Thr Thr Thr Ala Ser
    290                 295                 300

Gly Lys Leu Ile Thr Glu Trp Cys Cys Arg Ser Cys Thr Leu Pro Pro
305                 310                 315                 320

Leu Arg Tyr Arg Gly Glu Asp Gly Cys Trp Tyr Gly Met Glu Ile Arg
                325                 330                 335

Pro Leu Lys Glu Lys Glu Glu Asn Leu Val Asn Ser Leu Val Thr Ala
            340                 345                 350

<210> SEQ ID NO 11
<211> LENGTH: 151
<212> TYPE: PRT
<213> ORGANISM: Artificial
<220> FEATURE:
<223> OTHER INFORMATION: Dengue virus type 3 NS1 wing domain aa 30-180;
      X = A or C or S
<220> FEATURE:
<221> NAME/KEY: misc_feature
<222> LOCATION: (150)..(150)
<223> OTHER INFORMATION: Xaa can be Ala or Ser or Cys

<400> SEQUENCE: 11

Glu Gln Tyr Lys Phe Gln Ala Asp Ser Pro Lys Arg Leu Ala Thr Ala
1               5                   10                  15

Ile Ala Gly Ala Trp Glu Asn Gly Val Cys Gly Ile Arg Ser Thr Thr
            20                  25                  30

Arg Met Glu Asn Leu Leu Trp Lys Gln Ile Ala Asn Glu Leu Asn Tyr
        35                  40                  45

Ile Leu Trp Glu Asn Asn Ile Lys Leu Thr Val Val Val Gly Asp Ile
    50                  55                  60

Ile Gly Ile Leu Glu Gln Gly Lys Arg Thr Leu Thr Pro Gln Pro Met
65                  70                  75                  80

Glu Leu Lys Tyr Ser Trp Lys Thr Trp Gly Lys Ala Lys Ile Val Thr
                85                  90                  95

Ala Glu Thr Gln Asn Ser Ser Phe Ile Ile Asp Gly Pro Asn Thr Pro
            100                 105                 110

Glu Cys Pro Asn Ala Ser Arg Ala Trp Asn Val Trp Glu Val Glu Asp
        115                 120                 125

Tyr Gly Phe Gly Val Phe Thr Thr Asn Ile Trp Leu Lys Leu Arg Glu
    130                 135                 140

Met Tyr Ser Gln Leu Xaa Asp
145                 150

<210> SEQ ID NO 12
<211> LENGTH: 352
<212> TYPE: PRT
<213> ORGANISM: Dengue virus type 3

<400> SEQUENCE: 12

Asp Met Gly Cys Val Ile Asn Trp Lys Gly Lys Glu Leu Lys Cys Gly
```

-continued

```
1               5                   10                  15

Ser Gly Ile Phe Val Thr Asn Glu Val His Thr Trp Thr Glu Gln Tyr
            20                  25                  30

Lys Phe Gln Ala Asp Ser Pro Lys Arg Leu Ala Thr Ala Ile Ala Gly
        35                  40                  45

Ala Trp Glu Asn Gly Val Cys Gly Ile Arg Ser Thr Thr Arg Met Glu
    50                  55                  60

Asn Leu Leu Trp Arg Gln Ile Ala Asn Glu Leu Asn Tyr Ile Leu Trp
65                  70                  75                  80

Glu Asn Asn Ile Lys Leu Thr Val Val Val Gly Asp Ile Ile Gly Ile
                85                  90                  95

Leu Glu Gln Gly Lys Arg Thr Leu Thr Pro Gln Pro Met Glu Leu Lys
            100                 105                 110

Tyr Ser Trp Lys Thr Trp Gly Lys Ala Lys Ile Val Thr Ala Glu Thr
        115                 120                 125

Gln Asn Ser Ser Phe Ile Ile Asp Gly Pro Asn Thr Pro Glu Cys Pro
    130                 135                 140

Asn Ala Ser Arg Ala Trp Asn Val Trp Glu Val Glu Asp Tyr Gly Phe
145                 150                 155                 160

Gly Val Phe Thr Thr Asn Ile Trp Leu Lys Leu Arg Glu Met Tyr Ser
                165                 170                 175

Gln Leu Cys Asp His Arg Leu Met Ser Ala Ala Val Lys Asp Glu Arg
            180                 185                 190

Ala Val His Ala Asp Met Gly Tyr Trp Ile Glu Ser Gln Lys Asn Gly
        195                 200                 205

Ser Trp Lys Leu Glu Lys Ala Ser Leu Ile Glu Val Lys Thr Cys Thr
    210                 215                 220

Trp Pro Lys Ser His Thr Leu Trp Ser Asn Gly Val Leu Glu Ser Asp
225                 230                 235                 240

Met Ile Ile Pro Lys Ser Leu Ala Gly Pro Ile Ser Gln His Asn Tyr
                245                 250                 255

Arg Pro Gly Tyr His Thr Gln Thr Ala Gly Pro Trp His Leu Gly Lys
            260                 265                 270

Leu Glu Leu Asp Phe Asn Tyr Cys Glu Gly Thr Thr Val Val Ile Thr
        275                 280                 285

Glu Asn Cys Gly Thr Arg Gly Pro Ser Leu Arg Thr Thr Thr Val Ser
    290                 295                 300

Gly Lys Leu Ile His Glu Trp Cys Cys Arg Ser Cys Thr Leu Pro Pro
305                 310                 315                 320

Leu Arg Tyr Met Gly Glu Asp Gly Cys Trp Tyr Gly Met Glu Ile Arg
                325                 330                 335

Pro Ile Asn Glu Lys Glu Glu Asn Met Val Lys Ser Leu Val Ser Ala
            340                 345                 350
```

<210> SEQ ID NO 13
<211> LENGTH: 151
<212> TYPE: PRT
<213> ORGANISM: Artificial
<220> FEATURE:
<223> OTHER INFORMATION: Dengue virus type 4 NS1 wing domain aa 30-180;
X = A or C or S
<220> FEATURE:
<221> NAME/KEY: misc_feature
<222> LOCATION: (150)..(150)
<223> OTHER INFORMATION: Xaa can be Ala or Ser or Cys

<400> SEQUENCE: 13

```
Glu Gln Tyr Lys Phe Gln Pro Glu Ser Pro Ala Arg Leu Ala Ser Ala
1               5                   10                  15

Ile Leu Asn Ala His Lys Asp Gly Val Cys Gly Ile Arg Ser Thr Thr
            20                  25                  30

Arg Leu Glu Asn Ile Met Trp Lys Gln Ile Thr Asn Glu Leu Asn Tyr
        35                  40                  45

Val Leu Trp Glu Gly Gly His Asp Leu Thr Val Val Ala Gly Asp Val
    50                  55                  60

Lys Gly Val Leu Thr Lys Gly Lys Arg Ala Leu Thr Pro Pro Val Asn
65                  70                  75                  80

Asp Leu Lys Tyr Ser Trp Lys Thr Trp Gly Lys Ala Lys Ile Phe Thr
            85                  90                  95

Pro Glu Ala Arg Asn Ser Thr Phe Leu Ile Asp Gly Pro Asp Thr Ser
            100                 105                 110

Glu Cys Pro Asn Glu Arg Arg Ala Trp Asn Phe Phe Glu Val Glu Asp
        115                 120                 125

Tyr Gly Phe Gly Met Phe Thr Thr Asn Ile Trp Met Lys Phe Arg Glu
    130                 135                 140

Gly Ser Ser Glu Val Xaa Asp
145                 150
```

<210> SEQ ID NO 14
<211> LENGTH: 352
<212> TYPE: PRT
<213> ORGANISM: Dengue virus type 4

<400> SEQUENCE: 14

```
Asp Thr Gly Cys Ala Val Ser Trp Ser Gly Lys Glu Leu Lys Cys Gly
1               5                   10                  15

Ser Gly Ile Phe Val Ile Asp Asn Val His Thr Trp Thr Glu Gln Tyr
            20                  25                  30

Lys Phe Gln Pro Glu Ser Pro Ala Arg Leu Ala Ser Ala Ile Leu Asn
        35                  40                  45

Ala His Glu Asp Gly Val Cys Gly Ile Arg Ser Thr Thr Arg Leu Glu
    50                  55                  60

Asn Ile Met Trp Lys Gln Ile Thr Asn Glu Leu Asn Tyr Val Leu Trp
65                  70                  75                  80

Glu Gly Gly His Asp Leu Thr Val Val Ala Gly Asp Val Lys Gly Val
            85                  90                  95

Leu Ser Lys Gly Lys Arg Ala Leu Ala Pro Pro Val Asn Asp Leu Lys
            100                 105                 110

Tyr Ser Trp Lys Thr Trp Gly Lys Ala Lys Ile Phe Thr Pro Glu Ala
        115                 120                 125

Lys Asn Ser Thr Phe Leu Ile Asp Gly Pro Asp Thr Ser Glu Cys Pro
    130                 135                 140

Asn Glu Arg Arg Ala Trp Asn Phe Leu Glu Val Glu Asp Tyr Gly Phe
145                 150                 155                 160

Gly Met Phe Thr Thr Asn Ile Trp Met Lys Phe Arg Glu Gly Ser Ser
            165                 170                 175

Glu Val Cys Asp His Arg Leu Met Ser Ala Ala Ile Lys Asp Gln Lys
            180                 185                 190

Ala Val His Ala Asp Met Gly Tyr Trp Ile Glu Ser Ser Lys Asn Gln
        195                 200                 205

Thr Trp Gln Ile Glu Lys Ala Ser Leu Ile Glu Val Lys Thr Cys Leu
```

```
                    210                 215                 220
Trp Pro Lys Thr His Thr Leu Trp Ser Asn Gly Val Leu Glu Ser Gln
225                 230                 235                 240

Met Leu Ile Pro Lys Ala Tyr Ala Gly Pro Phe Ser Gln His Asn Tyr
                245                 250                 255

Arg Gln Gly Tyr Ala Thr Gln Thr Val Gly Pro Trp His Leu Gly Lys
                260                 265                 270

Leu Glu Ile Asp Phe Gly Glu Cys Pro Gly Thr Thr Val Thr Ile Gln
            275                 280                 285

Glu Asp Cys Asp His Arg Gly Pro Ser Leu Arg Thr Thr Thr Ala Ser
        290                 295                 300

Gly Lys Leu Val Thr Gln Trp Cys Cys Arg Ser Cys Thr Met Pro Pro
305                 310                 315                 320

Leu Arg Phe Leu Gly Glu Asp Gly Cys Trp Tyr Gly Met Glu Ile Arg
                325                 330                 335

Pro Leu Ser Glu Lys Glu Glu Asn Met Val Lys Ser Gln Val Ser Ala
            340                 345                 350
```

<210> SEQ ID NO 15
<211> LENGTH: 151
<212> TYPE: PRT
<213> ORGANISM: Artificial
<220> FEATURE:
<223> OTHER INFORMATION: West-Nile virus NS1 wing domain aa 30-180; X = A or C or S
<220> FEATURE:
<221> NAME/KEY: misc_feature
<222> LOCATION: (150)..(150)
<223> OTHER INFORMATION: Xaa can be Ala or Ser or Cys

<400> SEQUENCE: 15

```
Asp Arg Tyr Lys Phe Tyr Pro Glu Thr Pro Gln Gly Leu Ala Lys Ile
1               5                   10                  15

Ile Gln Lys Ala His Ala Glu Gly Val Cys Gly Leu Arg Ser Val Ser
            20                  25                  30

Arg Leu Glu His Gln Met Trp Glu Ala Ile Lys Asp Glu Leu Asn Thr
        35                  40                  45

Leu Leu Lys Glu Asn Gly Val Asp Leu Ser Val Val Val Glu Lys Gln
    50                  55                  60

Asn Gly Met Tyr Lys Ala Ala Pro Lys Arg Leu Ala Ala Thr Thr Glu
65                  70                  75                  80

Lys Leu Glu Met Gly Trp Lys Ala Trp Gly Lys Ser Ile Ile Phe Ala
                85                  90                  95

Pro Glu Leu Ala Asn Asn Thr Phe Val Ile Asp Gly Pro Glu Thr Glu
            100                 105                 110

Glu Cys Pro Thr Ala Asn Arg Ala Trp Asn Ser Met Glu Val Glu Asp
        115                 120                 125

Phe Gly Phe Gly Leu Thr Ser Thr Arg Met Phe Leu Arg Ile Arg Glu
    130                 135                 140

Thr Asn Thr Thr Glu Xaa Asp
145                 150
```

<210> SEQ ID NO 16
<211> LENGTH: 352
<212> TYPE: PRT
<213> ORGANISM: West Nile virus

<400> SEQUENCE: 16

```
Asp Thr Gly Cys Ala Ile Asp Ile Gly Arg Gln Glu Leu Arg Cys Gly
1               5                   10                  15

Ser Gly Val Phe Ile His Asn Asp Val Glu Ala Trp Met Asp Arg Tyr
            20                  25                  30

Lys Phe Tyr Pro Glu Thr Pro Gln Gly Leu Ala Lys Ile Ile Gln Lys
        35                  40                  45

Ala His Ala Glu Gly Val Cys Gly Leu Arg Ser Val Ser Arg Leu Glu
    50                  55                  60

His Gln Met Trp Glu Ala Ile Lys Asp Glu Leu Asn Thr Leu Leu Lys
65                  70                  75                  80

Glu Asn Gly Val Asp Leu Ser Val Val Glu Lys Gln Asn Gly Met
                85                  90                  95

Tyr Lys Ala Ala Pro Lys Arg Leu Ala Ala Thr Thr Glu Lys Leu Glu
            100                 105                 110

Met Gly Trp Lys Ala Trp Gly Lys Ser Ile Ile Phe Ala Pro Glu Leu
        115                 120                 125

Ala Asn Asn Thr Phe Val Ile Asp Gly Pro Glu Thr Glu Glu Cys Pro
    130                 135                 140

Thr Ala Asn Arg Ala Trp Asn Ser Met Glu Val Glu Asp Phe Gly Phe
145                 150                 155                 160

Gly Leu Thr Ser Thr Arg Met Phe Leu Arg Ile Arg Glu Thr Asn Thr
            165                 170                 175

Thr Glu Cys Asp Ser Lys Ile Ile Gly Thr Ala Val Lys Asn Asn Met
        180                 185                 190

Ala Val His Ser Asp Leu Ser Tyr Trp Ile Glu Ser Gly Leu Asn Asp
    195                 200                 205

Thr Trp Lys Leu Glu Arg Ala Val Leu Gly Glu Val Lys Ser Cys Thr
210                 215                 220

Trp Pro Glu Thr His Thr Leu Trp Gly Asp Gly Val Leu Glu Ser Asp
225                 230                 235                 240

Leu Ile Ile Pro Ile Thr Leu Ala Gly Pro Arg Ser Asn His Asn Arg
            245                 250                 255

Arg Pro Gly Tyr Lys Thr Gln Asn Gln Gly Pro Trp Asp Glu Gly Arg
        260                 265                 270

Val Glu Ile Asp Phe Asp Tyr Cys Pro Gly Thr Thr Val Thr Ile Ser
    275                 280                 285

Asp Ser Cys Glu His Arg Gly Pro Ala Ala Arg Thr Thr Thr Glu Ser
    290                 295                 300

Gly Lys Leu Ile Thr Asp Trp Cys Cys Arg Ser Cys Thr Leu Pro Pro
305                 310                 315                 320

Leu Arg Phe Gln Thr Glu Asn Gly Cys Trp Tyr Gly Met Glu Ile Arg
            325                 330                 335

Pro Thr Arg His Asp Glu Lys Thr Leu Val Gln Ser Arg Val Asn Ala
        340                 345                 350
```

<210> SEQ ID NO 17
<211> LENGTH: 151
<212> TYPE: PRT
<213> ORGANISM: Artificial
<220> FEATURE:
<223> OTHER INFORMATION: Yellow fever virus NS1 wing domain aa 30-180;
      X = A or C or S
<220> FEATURE:
<221> NAME/KEY: misc_feature
<222> LOCATION: (150)..(150)
<223> OTHER INFORMATION: Xaa can be Ala or Ser or Cys

<400> SEQUENCE: 17

Asn Lys Tyr Ser Tyr Tyr Pro Glu Asp Pro Val Lys Leu Ala Ser Ile
1               5                   10                  15

Val Lys Ala Ser Phe Glu Glu Gly Lys Cys Gly Leu Asn Ser Val Asp
            20                  25                  30

Ser Leu Glu His Glu Met Trp Arg Ser Arg Ala Asp Glu Ile Asn Ala
        35                  40                  45

Ile Phe Glu Glu Asn Glu Val Asp Ile Ser Val Val Gln Asp Pro
    50                  55                  60

Lys Asn Val Tyr Gln Arg Gly Thr His Pro Phe Ser Arg Ile Arg Asp
65                  70                  75                  80

Gly Leu Gln Tyr Gly Trp Lys Thr Trp Gly Lys Asn Leu Val Phe Ser
                85                  90                  95

Pro Gly Arg Lys Asn Gly Ser Phe Ile Ile Asp Gly Lys Ser Arg Lys
                100                 105                 110

Glu Cys Pro Phe Ser Asn Arg Val Trp Asn Ser Phe Gln Ile Glu Glu
            115                 120                 125

Phe Gly Thr Gly Val Phe Thr Thr Arg Val Tyr Met Asp Ala Val Phe
    130                 135                 140

Glu Tyr Thr Ile Asp Xaa Asp
145                 150

<210> SEQ ID NO 18
<211> LENGTH: 352
<212> TYPE: PRT
<213> ORGANISM: Yellow fever virus

<400> SEQUENCE: 18

Asp Gln Gly Cys Ala Ile Asn Phe Gly Lys Arg Glu Leu Lys Cys Gly
1               5                   10                  15

Asp Gly Ile Phe Ile Phe Arg Asp Ser Asp Asp Trp Leu Asn Lys Tyr
            20                  25                  30

Ser Tyr Tyr Pro Glu Asp Pro Val Lys Leu Ala Ser Ile Val Lys Ala
        35                  40                  45

Ser Phe Glu Glu Gly Lys Cys Gly Leu Asn Ser Val Asp Ser Leu Glu
    50                  55                  60

His Glu Met Trp Arg Ser Arg Ala Asp Glu Ile Asn Ala Ile Phe Glu
65                  70                  75                  80

Glu Asn Glu Val Asp Ile Ser Val Val Gln Asp Pro Lys Asn Val
                85                  90                  95

Tyr Gln Arg Gly Thr His Pro Phe Ser Arg Ile Arg Asp Gly Leu Gln
                100                 105                 110

Tyr Gly Trp Lys Thr Trp Gly Lys Asn Leu Val Phe Ser Pro Gly Arg
            115                 120                 125

Lys Asn Gly Ser Phe Ile Ile Asp Gly Lys Ser Arg Lys Glu Cys Pro
130                 135                 140

Phe Ser Asn Arg Val Trp Asn Ser Phe Gln Ile Glu Glu Phe Gly Thr
145                 150                 155                 160

Gly Val Phe Thr Thr Arg Val Tyr Met Asp Ala Val Phe Glu Tyr Thr
                165                 170                 175

Ile Asp Cys Asp Gly Ser Ile Leu Gly Ala Ala Val Asn Gly Lys Lys
            180                 185                 190

Ser Ala His Gly Ser Pro Thr Phe Trp Met Gly Ser His Glu Val Asn
        195                 200                 205

```
Gly Thr Trp Met Ile His Thr Leu Glu Ala Leu Asp Tyr Lys Glu Cys
        210                 215                 220

Glu Trp Pro Leu Thr His Thr Ile Gly Thr Ser Val Glu Glu Ser Glu
225                 230                 235                 240

Met Phe Met Pro Arg Ser Ile Gly Gly Pro Val Ser Ser His Asn His
                245                 250                 255

Ile Pro Gly Tyr Lys Val Gln Thr Asn Gly Pro Trp Met Gln Val Pro
            260                 265                 270

Leu Glu Val Lys Arg Glu Ala Cys Pro Gly Thr Ser Val Ile Ile Asp
        275                 280                 285

Gly Asn Cys Asp Gly Arg Gly Lys Ser Thr Arg Ser Thr Thr Asp Ser
290                 295                 300

Gly Lys Val Ile Pro Glu Trp Cys Cys Arg Ser Cys Thr Met Pro Pro
305                 310                 315                 320

Val Ser Phe His Gly Ser Asp Gly Cys Trp Tyr Pro Met Glu Ile Arg
                325                 330                 335

Pro Arg Lys Thr His Glu Ser His Leu Val Arg Ser Trp Val Thr Ala
            340                 345                 350

<210> SEQ ID NO 19
<211> LENGTH: 151
<212> TYPE: PRT
<213> ORGANISM: Artificial
<220> FEATURE:
<223> OTHER INFORMATION: Japanese encephalitis virus NS1 wing domain aa
      30-180; X = A or C or S
<220> FEATURE:
<221> NAME/KEY: misc_feature
<222> LOCATION: (150)..(150)
<223> OTHER INFORMATION: Xaa can be Ala or Ser or Cys

<400> SEQUENCE: 19

Asp Arg Tyr Lys Tyr Leu Pro Glu Thr Pro Arg Ser Leu Ala Lys Ile
1               5                   10                  15

Val His Lys Ala His Lys Glu Gly Val Cys Gly Val Arg Ser Val Thr
            20                  25                  30

Arg Leu Glu His Gln Met Trp Glu Ala Val Arg Asp Glu Leu Asn Val
        35                  40                  45

Leu Leu Lys Glu Asn Ala Val Asp Leu Ser Val Val Val Asn Lys Pro
    50                  55                  60

Val Gly Arg Tyr Arg Ser Ala Pro Lys Arg Leu Ser Met Thr Gln Glu
65                  70                  75                  80

Lys Phe Glu Met Gly Trp Lys Ala Trp Gly Lys Ser Ile Leu Phe Ala
                85                  90                  95

Pro Glu Leu Ala Asn Ser Thr Phe Val Val Asp Gly Pro Glu Thr Lys
            100                 105                 110

Glu Cys Pro Asp Glu His Arg Ala Trp Asn Ser Met Gln Ile Glu Asp
        115                 120                 125

Phe Gly Phe Gly Ile Thr Ser Thr Arg Val Trp Leu Lys Ile Arg Glu
    130                 135                 140

Glu Ser Thr Asp Glu Xaa Asp
145                 150

<210> SEQ ID NO 20
<211> LENGTH: 352
<212> TYPE: PRT
<213> ORGANISM: Japanese encephalitis virus

<400> SEQUENCE: 20
```

Asp Thr Gly Cys Ala Ile Asp Ile Thr Arg Lys Glu Met Arg Cys Gly
1               5                   10                  15

Ser Gly Ile Phe Val His Asn Asp Val Glu Ala Trp Val Asp Arg Tyr
            20                  25                  30

Lys Tyr Leu Pro Glu Thr Pro Arg Ser Leu Ala Lys Ile Val His Lys
        35                  40                  45

Ala His Lys Glu Gly Val Cys Gly Val Arg Ser Val Thr Arg Leu Glu
    50                  55                  60

His Gln Met Trp Glu Ala Val Arg Asp Glu Leu Asn Val Leu Leu Lys
65              70                  75                  80

Glu Asn Ala Val Asp Leu Ser Val Val Asn Lys Pro Val Gly Arg
                85                  90                  95

Tyr Arg Ser Ala Pro Lys Arg Leu Ser Met Thr Gln Glu Lys Phe Glu
            100                 105                 110

Met Gly Trp Lys Ala Trp Gly Lys Ser Ile Leu Phe Ala Pro Glu Leu
            115                 120                 125

Ala Asn Ser Thr Phe Val Val Asp Gly Pro Glu Thr Lys Glu Cys Pro
    130                 135                 140

Asp Glu His Arg Ala Trp Asn Ser Met Gln Ile Glu Asp Phe Gly Phe
145                 150                 155                 160

Gly Ile Thr Ser Thr Arg Val Trp Leu Lys Ile Arg Glu Glu Ser Thr
                165                 170                 175

Asp Glu Cys Asp Gly Ala Ile Ile Gly Thr Ala Val Lys Gly His Val
            180                 185                 190

Ala Val His Ser Asp Leu Ser Tyr Trp Ile Glu Ser Arg Tyr Asn Asp
        195                 200                 205

Thr Trp Lys Leu Glu Arg Ala Val Phe Gly Val Lys Ser Cys Thr
210                 215                 220

Trp Pro Glu Thr His Thr Leu Trp Gly Asp Gly Val Glu Glu Ser Glu
225                 230                 235                 240

Leu Ile Ile Pro His Thr Ile Ala Gly Pro Lys Ser Lys His Asn Arg
                245                 250                 255

Arg Glu Gly Tyr Lys Thr Gln Asn Gln Gly Pro Trp Asp Glu Asn Gly
            260                 265                 270

Ile Val Leu Asp Phe Asp Tyr Cys Pro Gly Thr Lys Val Thr Ile Thr
            275                 280                 285

Glu Asp Cys Gly Lys Arg Gly Pro Ser Val Arg Thr Thr Thr Asp Ser
    290                 295                 300

Gly Lys Leu Ile Thr Asp Trp Cys Cys Arg Ser Cys Ser Leu Pro Pro
305                 310                 315                 320

Leu Arg Phe Arg Thr Glu Asn Gly Cys Trp Tyr Gly Met Glu Ile Arg
                325                 330                 335

Pro Val Arg His Asp Glu Ala Thr Leu Val Arg Ser Gln Val Asp Ala
            340                 345                 350

<210> SEQ ID NO 21
<211> LENGTH: 534
<212> TYPE: PRT
<213> ORGANISM: Artificial
<220> FEATURE:
<223> OTHER INFORMATION: Fusion protein of tandem E. coli SlyD with Zika
      virus NS1 wing domain aa 30-180

<400> SEQUENCE: 21

Met Lys Val Ala Lys Asp Leu Val Val Ser Leu Ala Tyr Gln Val Arg

-continued

```
1               5                   10                  15
Thr Glu Asp Gly Val Leu Val Asp Glu Ser Pro Val Ser Ala Pro Leu
                20                  25                  30
Asp Tyr Leu His Gly His Gly Ser Leu Ile Ser Gly Leu Glu Thr Ala
                35                  40                  45
Leu Glu Gly His Glu Val Gly Asp Lys Phe Asp Val Ala Val Gly Ala
                50                  55                  60
Asn Asp Ala Tyr Gly Gln Tyr Asp Glu Asn Leu Val Gln Arg Val Pro
65              70                  75                  80
Lys Asp Val Phe Met Gly Val Asp Glu Leu Gln Val Gly Met Arg Phe
                85                  90                  95
Leu Ala Glu Thr Asp Gln Gly Pro Val Pro Val Glu Ile Thr Ala Val
                100                 105                 110
Glu Asp Asp His Val Val Asp Gly Asn His Met Leu Ala Gly Gln
                115                 120                 125
Asn Leu Lys Phe Asn Val Glu Val Val Ala Ile Arg Glu Ala Thr Glu
130             135                 140
Glu Glu Leu Ala His Gly His Val His Gly Ala His Asp His His His
145             150                 155                 160
Asp His Asp His Asp Gly Gly Ser Gly Gly Ser Gly Gly Gly
                165                 170                 175
Ser Gly Gly Gly Ser Gly Gly Ser Gly Gly Lys Val Ala Lys
                180                 185                 190
Asp Leu Val Val Ser Leu Ala Tyr Gln Val Arg Thr Glu Asp Gly Val
                195                 200                 205
Leu Val Asp Glu Ser Pro Val Ser Ala Pro Leu Asp Tyr Leu His Gly
                210                 215                 220
His Gly Ser Leu Ile Ser Gly Leu Glu Thr Ala Leu Glu Gly His Glu
225             230                 235                 240
Val Gly Asp Lys Phe Asp Val Ala Val Gly Ala Asn Asp Ala Tyr Gly
                245                 250                 255
Gln Tyr Asp Glu Asn Leu Val Gln Arg Val Pro Lys Asp Val Phe Met
                260                 265                 270
Gly Val Asp Glu Leu Gln Val Gly Met Arg Phe Leu Ala Glu Thr Asp
                275                 280                 285
Gln Gly Pro Val Pro Val Glu Ile Thr Ala Val Glu Asp Asp His Val
                290                 295                 300
Val Val Asp Gly Asn His Met Leu Ala Gly Gln Asn Leu Lys Phe Asn
305             310                 315                 320
Val Glu Val Val Ala Ile Arg Glu Ala Thr Glu Glu Glu Leu Ala His
                325                 330                 335
Gly His Val His Gly Ala His Asp His His His Asp His Asp His Asp
                340                 345                 350
Gly Gly Gly Ser Gly Gly Gly Ser Gly Gly Gly Ser Gly Gly Gly Ser
                355                 360                 365
Gly Gly Gly Ser Gly Gly Gly Asp Arg Tyr Lys Tyr His Pro Asp Ser
                370                 375                 380
Pro Arg Arg Leu Ala Ala Val Lys Gln Ala Trp Glu Glu Gly Ile
385             390                 395                 400
Cys Gly Ile Ser Ser Val Ser Arg Met Glu Asn Ile Met Trp Lys Ser
                405                 410                 415
Val Glu Gly Glu Leu Asn Ala Ile Leu Glu Glu Asn Gly Val Gln Leu
                420                 425                 430
```

```
Thr Val Val Val Gly Ser Val Lys Asn Pro Met Trp Arg Gly Pro Gln
        435                 440                 445

Arg Leu Pro Val Pro Val Asn Glu Leu Pro His Gly Trp Lys Ala Trp
    450                 455                 460

Gly Lys Ser Tyr Phe Val Arg Ala Ala Lys Thr Asn Asn Ser Phe Val
465                 470                 475                 480

Val Asp Gly Asp Thr Leu Lys Glu Cys Pro Leu Lys His Arg Ala Trp
                485                 490                 495

Asn Ser Phe Leu Val Glu Asp His Gly Phe Gly Val Phe His Thr Ser
            500                 505                 510

Val Trp Leu Lys Val Arg Glu Asp Tyr Ser Leu Glu Ala Asp Leu Glu
        515                 520                 525

His His His His His His
        530

<210> SEQ ID NO 22
<211> LENGTH: 545
<212> TYPE: PRT
<213> ORGANISM: Artificial
<220> FEATURE:
<223> OTHER INFORMATION: Fusion protein of tandem E. coli SlyD with Zika
      virus NS1 ?-ladder domain (aa 191-352, strain Mr 766)

<400> SEQUENCE: 22

Met Lys Val Ala Lys Asp Leu Val Val Ser Leu Ala Tyr Gln Val Arg
1               5                   10                  15

Thr Glu Asp Gly Val Leu Val

```
                    245                 250                 255
Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
    290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Leu Ala His
            325                 330                 335

Gly His Val His Gly Ala His Asp His His Asp His Asp His Asp
        340                 345                 350

Gly Gly Gly Ser Gly Gly Gly Ser Gly Gly Gly Ser Gly Gly Gly Ser
            355                 360                 365

Gly Gly Gly Ser Gly Gly Gly Arg Glu Ala Ala His Ser Asp Leu Gly
        370                 375                 380

Tyr Trp Ile Glu Ser Glu Lys Asn Asp Thr Trp Arg Leu Lys Arg Ala
385                 390                 395                 400

His Leu Ile Glu Met Lys Thr Ala Glu Trp Pro Lys Ser His Thr Leu
            405                 410                 415

Trp Thr Asp Gly Val Glu Glu Ser Asp Leu Ile Ile Pro Lys Ser Leu
        420                 425                 430

Ala Gly Pro Leu Ser His His Asn Thr Arg Glu Gly Tyr Arg Thr Gln
    435                 440                 445

Val Lys Gly Pro Trp His Ser Glu Glu Leu Glu Ile Arg Phe Glu Glu
    450                 455                 460

Cys Pro Gly Thr Lys Val Tyr Val Glu Glu Thr Cys Gly Thr Arg Gly
465                 470                 475                 480

Pro Ser Leu Arg Ser Thr Thr Ala Ser Gly Arg Val Ile Glu Glu Trp
            485                 490                 495

Cys Cys Arg Glu Cys Thr Met Pro Pro Leu Ser Phe Arg Ala Lys Asp
        500                 505                 510

Gly Cys Trp Tyr Gly Met Glu Ile Arg Pro Arg Lys Glu Pro Glu Ser
    515                 520                 525

Asn Leu Val Arg Ser Met Val Thr Ala Leu Glu His His His His
    530                 535                 540

His
545

<210> SEQ ID NO 23
<211> LENGTH: 358
<212> TYPE: PRT
<213> ORGANISM: Artificial
<220> FEATURE:
<223> OTHER INFORMATION: Fusion protein of E. coli SlyD with Zika virus
      NS1 ?-ladder domain (aa 191-352, strain Mr 766)

<400> SEQUENCE: 23

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45
```

```
Leu Glu Gly His Glu Val Gly Asp Lys Phe Asp Val Ala Val Gly Ala
 50                  55                  60

Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                 85                  90                  95

Leu Ala Glu Thr Asp Gln Gly Pro Val Pro Val Glu Ile Thr Ala Val
                100                 105                 110

Glu Asp Asp His Val Val Asp Gly Asn His Met Leu Ala Gly Gln
                115                 120                 125

Asn Leu Lys Phe Asn Val Glu Val Val Ala Ile Arg Glu Ala Thr Glu
130                 135                 140

Glu Glu Leu Ala His Gly His Val His Gly Ala His Asp His His His
145                 150                 155                 160

Asp His Asp His Asp Gly Gly Ser Gly Gly Ser Gly Gly Gly
                165                 170                 175

Ser Gly Gly Ser Gly Gly Ser Gly Gly Arg Glu Ala Ala
                180                 185                 190

His Ser Asp Leu Gly Tyr Trp Ile Glu Ser Glu Lys Asn Asp Thr Trp
                195                 200                 205

Arg Leu Lys Arg Ala His Leu Ile Glu Met Lys Thr Ala Glu Trp Pro
210                 215                 220

Lys Ser His Thr Leu Trp Thr Asp Gly Val Glu Ser Asp Leu Ile
225                 230                 235                 240

Ile Pro Lys Ser Leu Ala Gly Pro Leu Ser His His Asn Thr Arg Glu
                245                 250                 255

Gly Tyr Arg Thr Gln Val Lys Gly Pro Trp His Ser Glu Glu Leu Glu
                260                 265                 270

Ile Arg Phe Glu Glu Cys Pro Gly Thr Lys Val Tyr Val Glu Glu Thr
                275                 280                 285

Cys Gly Thr Arg Gly Pro Ser Leu Arg Ser Thr Thr Ala Ser Gly Arg
                290                 295                 300

Val Ile Glu Glu Trp Cys Cys Arg Glu Cys Thr Met Pro Pro Leu Ser
305                 310                 315                 320

Phe Arg Ala Lys Asp Gly Cys Trp Tyr Gly Met Glu Ile Arg Pro Arg
                325                 330                 335

Lys Glu Pro Glu Ser Asn Leu Val Arg Ser Met Val Thr Ala Leu Glu
                340                 345                 350

His His His His His His
        355

<210> SEQ ID NO 24
<211> LENGTH: 162
<212> TYPE: PRT
<213> ORGANISM: Dengue virus type 1

<400> SEQUENCE: 24

Ser Lys Ala Val His Ala Asp Met Gly Tyr Trp Ile Glu Ser Glu Lys
 1               5                  10                  15

Asn Glu Thr Trp Lys Leu Ala Arg Ala Ser Phe Ile Glu Val Lys Thr
                 20                  25                  30

Ala Ile Trp Pro Lys Ser His Thr Leu Trp Ser Asn Gly Val Leu Glu
             35                  40                  45

Ser Glu Met Ile Ile Pro Lys Ile Tyr Gly Gly Pro Ile Ser Gln His
         50                  55                  60
```

```
Asn Tyr Arg Pro Gly Tyr Phe Thr Gln Thr Ala Gly Pro Trp His Leu
 65                  70                  75                  80

Gly Lys Leu Glu Leu Asp Phe Asp Leu Cys Glu Gly Thr Thr Val Val
                 85                  90                  95

Val Asp Glu His Cys Gly Asn Arg Gly Pro Ser Leu Arg Thr Thr Ser
            100                 105                 110

Val Thr Gly Lys Ile Ile His Glu Trp Cys Cys Arg Ser Cys Thr Leu
        115                 120                 125

Pro Pro Leu Arg Phe Arg Gly Glu Asp Gly Cys Trp Tyr Gly Met Glu
130                 135                 140

Ile Arg Pro Val Lys Glu Lys Glu Glu Asn Leu Val Lys Ser Met Val
145                 150                 155                 160

Ser Ala

<210> SEQ ID NO 25
<211> LENGTH: 162
<212> TYPE: PRT
<213> ORGANISM: Dengue virus type 2

<400> SEQUENCE: 25

Asn Arg Ala Val His Ala Asp Met Gly Tyr Trp Ile Glu Ser Ala Leu
  1               5                  10                  15

Asn Asp Thr Trp Lys Ile Glu Lys Ala Ser Phe Ile Glu Val Lys Asn
             20                  25                  30

Ala His Trp Pro Lys Ser His Thr Leu Trp Ser Asn Gly Val Leu Glu
         35                  40                  45

Ser Glu Met Ile Ile Pro Lys Asn Leu Ala Gly Pro Val Ser Gln His
 50                  55                  60

Asn Tyr Arg Pro Gly Tyr His Thr Gln Ile Ala Gly Pro Trp His Leu
 65                  70                  75                  80

Gly Lys Leu Glu Met Asp Phe Asp Phe Cys Asp Gly Thr Thr Val Val
                 85                  90                  95

Val Thr Glu Asp Cys Gly Asn Arg Gly Pro Ser Leu Arg Thr Thr Thr
            100                 105                 110

Ala Ser Gly Lys Leu Ile Thr Glu Trp Cys Cys Arg Ser Cys Thr Leu
        115                 120                 125

Pro Pro Leu Arg Tyr Arg Gly Glu Asp Gly Cys Trp Tyr Gly Met Glu
130                 135                 140

Ile Arg Pro Leu Lys Glu Lys Glu Glu Asn Leu Val Asn Ser Leu Val
145                 150                 155                 160

Thr Ala

<210> SEQ ID NO 26
<211> LENGTH: 162
<212> TYPE: PRT
<213> ORGANISM: Dengue virus type 3

<400> SEQUENCE: 26

Glu Arg Ala Val His Ala Asp Met Gly Tyr Trp Ile Glu Ser Gln Lys
  1               5                  10                  15

Asn Gly Ser Trp Lys Leu Glu Lys Ala Ser Leu Ile Glu Val Lys Thr
             20                  25                  30

Ala Thr Trp Pro Lys Ser His Thr Leu Trp Ser Asn Gly Val Leu Glu
         35                  40                  45

Ser Asp Met Ile Ile Pro Lys Ser Leu Ala Gly Pro Ile Ser Gln His
```

```
                    50                  55                  60
Asn Tyr Arg Pro Gly Tyr His Thr Gln Thr Ala Gly Pro Trp His Leu
 65                  70                  75                  80

Gly Lys Leu Glu Leu Asp Phe Asn Tyr Cys Glu Gly Thr Thr Val Val
                     85                  90                  95

Ile Thr Glu Asn Cys Gly Thr Arg Gly Pro Ser Leu Arg Thr Thr Thr
                100                 105                 110

Val Ser Gly Lys Leu Ile His Glu Trp Cys Cys Arg Ser Cys Thr Leu
            115                 120                 125

Pro Pro Leu Arg Tyr Met Gly Glu Asp Gly Cys Trp Tyr Gly Met Glu
        130                 135                 140

Ile Arg Pro Ile Asn Glu Lys Glu Glu Asn Met Val Lys Ser Leu Val
145                 150                 155                 160

Ser Ala

<210> SEQ ID NO 27
<211> LENGTH: 162
<212> TYPE: PRT
<213> ORGANISM: Dengue virus type 4

<400> SEQUENCE: 27

Gln Lys Ala Val His Ala Asp Met Gly Tyr Trp Ile Glu Ser Ser Lys
 1               5                  10                  15

Asn Gln Thr Trp Gln Ile Glu Lys Ala Ser Leu Ile Glu Val Lys Thr
                20                  25                  30

Ala Leu Trp Pro Lys Thr His Thr Leu Trp Ser Asn Gly Val Leu Glu
            35                  40                  45

Ser Gln Met Leu Ile Pro Arg Ser Tyr Ala Gly Pro Phe Ser Gln His
        50                  55                  60

Asn Tyr Arg Gln Gly Tyr Ala Thr Gln Thr Ala Gly Pro Trp His Leu
 65                  70                  75                  80

Gly Lys Leu Glu Ile Asp Phe Gly Glu Cys Pro Gly Thr Thr Val Thr
                 85                  90                  95

Ile Gln Glu Asp Cys Asp His Arg Gly Pro Ser Leu Arg Thr Thr Thr
                100                 105                 110

Ala Ser Gly Lys Leu Val Thr Gln Trp Cys Cys Arg Ser Cys Thr Met
            115                 120                 125

Pro Pro Leu Arg Phe Leu Gly Glu Asp Gly Cys Trp Tyr Gly Met Glu
        130                 135                 140

Ile Arg Pro Leu Ser Glu Lys Glu Glu Asn Met Val Lys Ser Gln Val
145                 150                 155                 160

Thr Ala

<210> SEQ ID NO 28
<211> LENGTH: 534
<212> TYPE: PRT
<213> ORGANISM: Artificial Sequence
<220> FEATURE:
<223> OTHER INFORMATION: Fusion protein of tandem E. coli SlyD with
      Dengue virus type 1 NS1 wing domain aa 30

```
Thr Glu Asp Gly Val Leu Val Asp Glu Ser Pro Val Ser Ala Pro Leu
         20                  25                  30

Asp Tyr Leu His Gly His Gly Ser Leu Ile Ser Gly Leu Glu Thr Ala
         35                  40                  45

Leu Glu Gly His Glu Val Gly Asp Lys Phe Asp Val Ala Val Gly Ala
         50                  55                  60

Asn Asp Ala Tyr Gly Gln Tyr Asp Glu Asn Leu Val Gln Arg Val Pro
65                   70                  75                  80

Lys Asp Val Phe Met Gly Val Asp Glu Leu Gln Val Gly Met Arg Phe
                 85                  90                  95

Leu Ala Glu Thr Asp Gln Gly Pro Val Pro Val Glu Ile Thr Ala Val
             100                 105                 110

Glu Asp Asp His Val Val Asp Gly Asn His Met Leu Ala Gly Gln
         115                 120                 125

Asn Leu Lys Phe Asn Val Glu Val Ala Ile Arg Glu Ala Thr Glu
130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                 165                 170                 175

Ser Gly Gly Gly Ser Gly Gly Gly Ser Gly Gly Gly Lys Val Ala Lys
             180                 185                 190

Asp Leu Val Val Ser Leu Ala Tyr Gln Val Arg Thr Glu Asp Gly Val
         195                 200                 205

Leu Val Asp Glu Ser Pro Val Ser Ala Pro Leu Asp Tyr Leu His Gly
         210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                 245                 250                 255

Gln Tyr Asp Glu Asn Leu Val Gln Arg Val Pro Lys Asp Val Phe Met
             260                 265                 270

Gly Val Asp Glu Leu Gln Val Gly Met Arg Phe Leu Ala Glu Thr Asp
         275                 280                 285

Gln Gly Pro Val Pro Val Glu Ile Thr Ala Val Glu Asp Asp His Val
         290                 295                 300

Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                 325                 330                 335

Gly His Val His Gly Ala His Asp His His Asp His Asp His Asp
             340                 345                 350

Gly Gly Gly Ser Gly Gly Gly Ser Gly Gly Gly Ser Gly Gly Gly Ser
         355                 360                 365

Gly Gly Gly Ser Gly Gly Gly Glu Gln Tyr Lys Phe Gln Ala Asp Ser
         370                 375                 380

Pro Lys Arg Leu Ser Ala Ala Ile Gly Lys Ala Trp Glu Glu Gly Val
385                 390                 395                 400

Cys Gly Ile Arg Ser Ala Thr Arg Leu Glu Asn Ile Met Trp Lys Gln
                 405                 410                 415

Ile Ser Asn Glu Leu Asn His Ile Leu Leu Glu Asn Asp Met Lys Phe
             420                 425                 430
```

```
Thr Val Val Val Gly Asp Val Ala Gly Ile Leu Ala Gln Gly Lys Lys
            435                 440                 445

Met Ile Arg Pro Gln Pro Met Glu His Lys Tyr Ser Trp Lys Ser Trp
450                 455                 460

Gly Lys Ala Lys Ile Ile Gly Ala Asp Val Gln Asn Thr Thr Phe Ile
465                 470                 475                 480

Ile Asp Gly Pro Asn Thr Pro Glu Cys Pro Asp Asp Gln Arg Ala Trp
                485                 490                 495

Asn Ile Trp Glu Val Glu Asp Tyr Gly Phe Gly Ile Phe Thr Thr Asn
            500                 505                 510

Ile Trp Leu Lys Leu Arg Asp Ser Tyr Thr Gln Val Xaa Asp Leu Glu
            515                 520                 525

His His His His His His
            530

<210> SEQ ID NO 29
<211> LENGTH: 534
<212> TYPE: PRT
<213> ORGANISM: Artificial
<220> FEATURE:
<223> OTHER INFORMATION: Fusion protein of tandem E. coli SlyD with
      Dengue virus type 2 NS1 wing domain aa 30-180
<220> FEATURE:
<221> NAME/KEY: misc_feature
<222> LOCATION: (525)..(525)
<223> OTHER INFORMATION: Xaa can be Ala or Ser or Cys

<400> SEQUENCE: 29

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
            35                  40                  45

Leu Glu Gly His Glu Val Gly Asp Lys Phe Asp Val Ala Val Gly Ala
        50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
            115                 120                 125

Asn Leu Lys Phe Asn Val Glu Val Val Ala Ile Arg Glu Ala Thr Glu
130                 135                 140

Glu Glu Leu Ala His Gly His Val His Gly Ala His Asp His His His
145                 150                 155                 160

Asp His Asp His Asp Gly Gly Gly Ser Gly Gly Gly Ser Gly Gly Gly
                165                 170                 175

Ser Gly Gly Gly Ser Gly Gly Gly Ser Gly Gly Gly Lys Val Ala Lys
            180                 185                 190

Asp Leu Val Val Ser Leu Ala Tyr Gln Val Arg Thr Glu Asp Gly Val
            195                 200                 205

Leu Val Asp Glu Ser Pro Val Ser Ala Pro Leu Asp Tyr Leu His Gly
        210                 215                 220

His Gly Ser Leu Ile Ser Gly Leu Glu Thr Ala Leu Glu Gly His Glu
```

```
                225                 230                 235                 240
    Val Gly Asp Lys Phe Asp Val Ala Val Gly Ala Asn Asp Ala Tyr Gly
                    245                 250                 255

Gln Tyr Asp Glu Asn Leu Val Gln Arg Val Pro Lys Asp Val Phe Met
                260                 265                 270

Gly Val Asp Glu Leu Gln Val Gly Met Arg Phe Leu Ala Glu Thr Asp
                275                 280                 285

Gln Gly Pro Val Pro Val Glu Ile Thr Ala Val Glu Asp Asp His Val
                290                 295                 300

Val Val Asp Gly Asn His Met Leu Ala Gly Gln Asn Leu Lys Phe Asn
    305                 310                 315                 320

Val Glu Val Val Ala Ile Arg Glu Ala Thr Glu Glu Leu Ala His
                    325                 330                 335

Gly His Val His Gly Ala His Asp His His Asp His Asp His Asp
                340                 345                 350

Gly Gly Gly Ser Gly Gly Gly Ser Gly Gly Gly Ser Gly Gly Ser
                355                 360                 365

Gly Gly Gly Ser Gly Gly Gly Glu Gln Tyr Lys Phe Gln Pro Glu Ser
                370                 375                 380

Pro Ser Lys Leu Ala Ser Ala Ile Gln Lys Ala His Glu Glu Gly Ile
    385                 390                 395                 400

Cys Gly Ile Arg Ser Val Thr Arg Leu Glu Asn Leu Met Trp Lys Gln
                    405                 410                 415

Ile Thr Pro Glu Leu Asn His Ile Leu Ser Glu Asn Glu Val Lys Leu
                420                 425                 430

Thr Ile Met Thr Gly Asp Ile Lys Gly Ile Met Gln Ala Gly Lys Arg
                435                 440                 445

Ser Leu Arg Pro Gln Pro Thr Glu Leu Lys Tyr Ser Trp Lys Thr Trp
                450                 455                 460

Gly Lys Ala Lys Met Leu Ser Thr Glu Ser His Asn Gln Thr Phe Leu
    465                 470                 475                 480

Ile Asp Gly Pro Glu Thr Ala Glu Cys Pro Asn Thr Asn Arg Ala Trp
                    485                 490                 495

Asn Ser Leu Glu Val Glu Asp Tyr Gly Phe Gly Val Phe Thr Thr Asn
                500                 505                 510

Ile Trp Leu Lys Leu Lys Glu Lys Gln Asp Val Phe Xaa Asp Leu Glu
                515                 520                 525

His His His His His His
                530

<210> SEQ ID NO 30
<211> LENGTH: 534
<212> TYPE: PRT
<213> ORGANISM: artificial
<220> FEATURE:
<223> OTHER INFORMATION: Fusion protein of tandem E. coli SlyD with
      Dengue virus type 3 NS1 wing domain aa 30-180
<220> FEATURE:
<221> NAME/KEY: misc_feature
<222> LOCATION: (525)..(525)
<223> OTHER INFORMATION: Xaa can be Ala or Ser or Cys

<400> SEQUENCE: 30

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
                20                  25                  30
```

```
Asp Tyr Leu His Gly His Gly Ser Leu Ile Ser Gly Leu Glu Thr Ala
         35                  40                  45

Leu Glu Gly His Glu Val Gly Asp Lys Phe Asp Val Ala Val Gly Ala
 50                  55                  60

Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                 85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Val Ala Ile Arg Glu Ala Thr Glu
        130                 135                 140

Glu Glu Leu Ala His Gly His Val His Gly Ala His Asp His His His
145                 150                 155                 160

Asp His Asp His Asp Gly Gly Gly Ser Gly Gly Ser Gly Gly Gly
                165                 170                 175

Ser Gly Gly Gly Ser Gly Gly Ser Gly Gly Gly Lys Val Ala Lys
            180                 185                 190

Asp Leu Val Val Ser Leu Ala Tyr Gln Val Arg Thr Glu Asp Gly Val
            195                 200                 205

Leu Val Asp Glu Ser Pro Val Ser Ala Pro Leu Asp Tyr Leu His Gly
        210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
                245                 250                 255

Gln Tyr Asp Glu Asn Leu Val Gln Arg Val Pro Lys Asp Val Phe Met
            260                 265                 270

Gly Val Asp Glu Leu Gln Val Gly Met Arg Phe Leu Ala Glu Thr Asp
        275                 280                 285

Gln Gly Pro Val Pro Val Glu Ile Thr Ala Val Glu Asp Asp His Val
        290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Glu Leu Ala His
                325                 330                 335

Gly His Val His Gly Ala His Asp His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Glu Gln Tyr Lys Phe Gln Ala Asp Ser
370                 375                 380

Pro Lys Arg Leu Ala Thr Ala Ile Ala Gly Ala Trp Glu Asn Gly Val
385                 390                 395                 400

Cys Gly Ile Arg Ser Thr Thr Arg Met Glu Asn Leu Leu Trp Lys Gln
                405                 410                 415

Ile Ala Asn Glu Leu Asn Tyr Ile Leu Trp Glu Asn Asn Ile Lys Leu
            420                 425                 430

Thr Val Val Val Gly Asp Ile Ile Gly Ile Leu Glu Gln Gly Lys Arg
        435                 440                 445
```

```
Thr Leu Thr Pro Gln Pro Met Glu Leu Lys Tyr Ser Trp Lys Thr Trp
        450                 455                 460

Gly Lys Ala Lys Ile Val Thr Ala Glu Thr Gln Asn Ser Ser Phe Ile
465                 470                 475                 480

Ile Asp Gly Pro Asn Thr Pro Glu Cys Pro Asn Ala Ser Arg Ala Trp
                485                 490                 495

Asn Val Trp Glu Val Glu Asp Tyr Gly Phe Gly Val Phe Thr Thr Asn
                500                 505                 510

Ile Trp Leu Lys Leu Arg Glu Met Tyr Ser Gln Leu Xaa Asp Leu Glu
            515                 520                 525

His His His His His His
        530

<210> SEQ ID NO 31
<211> LENGTH: 534
<212> TYPE: PRT
<213> ORGANISM: Artificial
<220> FEATURE:
<223> OTHER INFORMATION: Fusion protein of tandem E. coli SlyD with
      Dengue virus type 4 NS1 wing domain aa 30-180
<220> FEATURE:
<221> NAME/KEY: misc_feature
<222> LOCATION: (525)..(525)
<223> OTHER INFORMATION: Xaa can be Ala or Ser or Cys

<400> SEQUENCE: 31

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
    50                  55                  60

Asn Asp Ala Tyr Gly Gln Tyr Asp Glu Asn Leu Val Gln Arg Val Pro
65                  70                  75                  80

Lys Asp Val Phe Met Gly Val Asp Glu Leu Gln Val Gly Met Arg Phe
                85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                165                 170                 175

Ser Gly Gly Gly Ser Gly Gly Gly Ser Gly Gly Lys Val Ala Lys
            180                 185                 190

Asp Leu Val Val Ser Leu Ala Tyr Gln Val Arg Thr Glu Asp Gly Val
        195                 200                 205

Leu Val Asp Glu Ser Pro Val Ser Ala Pro Leu Asp Tyr Leu His Gly
    210                 215                 220

His Gly Ser Leu Ile Ser Gly Leu Glu Thr Ala Leu Glu Gly His Glu
225                 230                 235                 240

Val Gly Asp Lys Phe Asp Val Ala Val Gly Ala Asn Asp Ala Tyr Gly
```

```
                    245                 250                 255
Gln Tyr Asp Glu Asn Leu Val Gln Arg Val Pro Lys Asp Val Phe Met
                260                 265                 270

Gly Val Asp Glu Leu Gln Val Gly Met Arg Phe Leu Ala Glu Thr Asp
            275                 280                 285

Gln Gly Pro Val Pro Val Glu Ile Thr Ala Val Glu Asp Asp His Val
        290                 295                 300

Val Val Asp Gly Asn His Met Leu Ala Gly Gln Asn Leu Lys Phe Asn
305                 310                 315                 320

Val Glu Val Val Ala Ile Arg Glu Ala Thr Glu Glu Leu Ala His
                325                 330                 335

Gly His Val His Gly Ala His Asp His His Asp His Asp His Asp
            340                 345                 350

Gly Gly Gly Ser Gly Gly Gly Ser Gly Gly Gly Ser Gly Gly Gly Ser
        355                 360                 365

Gly Gly Gly Ser Gly Gly Gly Glu Gln Tyr Lys Phe Gln Pro Glu Ser
        370                 375                 380

Pro Ala Arg Leu Ala Ser Ala Ile Leu Asn Ala His Lys Asp Gly Val
385                 390                 395                 400

Cys Gly Ile Arg Ser Thr Thr Arg Leu Glu Asn Ile Met Trp Lys Gln
                405                 410                 415

Ile Thr Asn Glu Leu Asn Tyr Val Leu Trp Glu Gly Gly His Asp Leu
            420                 425                 430

Thr Val Val Ala Gly Asp Val Lys Gly Val Leu Thr Lys Gly Lys Arg
        435                 440                 445

Ala Leu Thr Pro Pro Val Asn Asp Leu Lys Tyr Ser Trp Lys Thr Trp
450                 455                 460

Gly Lys Ala Lys Ile Phe Thr Pro Glu Ala Arg Asn Ser Thr Phe Leu
465                 470                 475                 480

Ile Asp Gly Pro Asp Thr Ser Glu Cys Pro Asn Glu Arg Arg Ala Trp
                485                 490                 495

Asn Phe Phe Glu Val Glu Asp Tyr Gly Phe Gly Met Phe Thr Thr Asn
            500                 505                 510

Ile Trp Met Lys Phe Arg Glu Gly Ser Ser Glu Val Xaa Asp Leu Glu
        515                 520                 525

His His His His His His
        530

<210> SEQ ID NO 32
<211> LENGTH: 358
<212> TYPE: PRT
<213> ORGANISM: Artificial
<220> FEATURE:
<223> OTHER INFORMATION: Fusion protein of tandem E. coli SlyD with
      Dengue virus type 1 NS1 ?-ladder domain aa 191-352

<400> SEQUENCE: 32

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
                20                  25                  30

Asp Tyr Leu His Gly His Gly Ser Leu Ile Ser Gly Leu Glu Thr Ala
            35                  40                  45

Leu Glu Gly His Glu Val Gly Asp Lys Phe Asp Val Ala Val Gly Ala
        50                  55                  60
```

```
Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                 85                  90                  95

Leu Ala Glu Thr Asp Gln Gly Pro Val Pro Val Glu Ile Thr Ala Val
            100                 105                 110

Glu Asp Asp His Val Val Asp Gly Asn His Met Leu Ala Gly Gln
        115                 120                 125

Asn Leu Lys Phe Asn Val Glu Val Val Ala Ile Arg Glu Ala Thr Glu
        130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
            165                 170                 175

Ser Gly Gly Gly Ser Gly Gly Gly Ser Gly Gly Gly Ser Lys Ala Val
            180                 185                 190

His Ala Asp Met Gly Tyr Trp Ile Glu Ser Glu Lys Asn Glu Thr Trp
            195                 200                 205

Lys Leu Ala Arg Ala Ser Phe Ile Glu Val Lys Thr Ala Ile Trp Pro
210                 215                 220

Lys Ser His Thr Leu Trp Ser Asn Gly Val Leu Glu Ser Glu Met Ile
225                 230                 235                 240

Ile Pro Lys Ile Tyr Gly Gly Pro Ile Ser Gln His Asn Tyr Arg Pro
                245                 250                 255

Gly Tyr Phe Thr Gln Thr Ala Gly Pro Trp His Leu Gly Lys Leu Glu
            260                 265                 270

Leu Asp Phe Asp Leu Cys Glu Gly Thr Thr Val Val Val Asp Glu His
            275                 280                 285

Cys Gly Asn Arg Gly Pro Ser Leu Arg Thr Thr Ser Val Thr Gly Lys
            290                 295                 300

Ile Ile His Glu Trp Cys Cys Arg Ser Cys Thr Leu Pro Pro Leu Arg
305                 310                 315                 320

Phe Arg Gly Glu Asp Gly Cys Trp Tyr Gly Met Glu Ile Arg Pro Val
                325                 330                 335

Lys Glu Lys Glu Glu Asn Leu Val Lys Ser Met Val Ser Ala Leu Glu
            340                 345                 350

His His His His His His
        355

<210> SEQ ID NO 33
<211> LENGTH: 358
<212> TYPE: PRT
<213> ORGANISM: Artificial
<220> FEATURE:
<223> OTHER INFORMATION: Fusion protein of tandem E. coli SlyD with
      Dengue virus type 2 NS1 ?-ladder domain aa 191-352

<400> SEQUENCE: 33

Met Lys Val Ala Lys Asp Leu Val Val Ser Leu Ala Tyr Gln Val Arg
 1               5                  10                  15

Thr Glu Asp Gly Val Leu Val Asp Glu Ser Pro Val Ser Ala Pro Leu
             20                  25                  30

Asp Tyr Leu His Gly His Gly Ser Leu Ile Ser Gly Leu Glu Thr Ala
         35                  40                  45

Leu Glu Gly His Glu Val Gly Asp Lys Phe Asp Val Ala Val Gly Ala
     50                  55                  60
```

```
Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                 85                  90                  95

Leu Ala Glu Thr Asp Gln Gly Pro Val Pro Val Glu Ile Thr Ala Val
            100                 105                 110

Glu Asp Asp His Val Val Val Asp Gly Asn His Met Leu Ala Gly Gln
        115                 120                 125

Asn Leu Lys Phe Asn Val Glu Val Val Ala Ile Arg Glu Ala Thr Glu
    130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                165                 170                 175

Ser Gly Gly Gly Ser Gly Gly Gly Ser Gly Gly Gly Asn Arg Ala Val
            180                 185                 190

His Ala Asp Met Gly Tyr Trp Ile Glu Ser Ala Leu Asn Asp Thr Trp
        195                 200                 205

Lys Ile Glu Lys Ala Ser Phe Ile Glu Val Lys Asn Ala His Trp Pro
210                 215                 220

Lys Ser His Thr Leu Trp Ser Asn Gly Val Leu Glu Ser Glu Met Ile
225                 230                 235                 240

Ile Pro Lys Asn Leu Ala Gly Pro Val Ser Gln His Asn Tyr Arg Pro
                245                 250                 255

Gly Tyr His Thr Gln Ile Ala Gly Pro Trp His Leu Gly Lys Leu Glu
            260                 265                 270

Met Asp Phe Asp Phe Cys Asp Gly Thr Thr Val Val Val Thr Glu Asp
        275                 280                 285

Cys Gly Asn Arg Gly Pro Ser Leu Arg Thr Thr Thr Ala Ser Gly Lys
    290                 295                 300

Leu Ile Thr Glu Trp Cys Cys Arg Ser Cys Thr Leu Pro Pro Leu Arg
305                 310                 315                 320

Tyr Arg Gly Glu Asp Gly Cys Trp Tyr Gly Met Glu Ile Arg Pro Leu
                325                 330                 335

Lys Glu Lys Glu Glu Asn Leu Val Asn Ser Leu Val Thr Ala Leu Glu
            340                 345                 350

His His His His His His
        355

<210> SEQ ID NO 34
<211> LENGTH: 358
<212> TYPE: PRT
<213> ORGANISM: Artificial
<220> FEATURE:
<223> OTHER INFORMATION: Fusion protein of tandem E. coli SlyD with
      Dengue virus type 3 NS1 ?-ladder domain aa 191-352

<400> SEQUENCE: 34

Met Lys Val Ala Lys Asp Leu Val Val Ser Leu Ala Tyr Gln Val Arg
1               5                   10                  15

Thr Glu Asp Gly Val Leu Val Asp Glu Ser Pro Val Ser Ala Pro Leu
            20                  25                  30

Asp Tyr Leu His Gly His Gly Ser Leu Ile Ser Gly Leu Glu Thr Ala
        35                  40                  45

Leu Glu Gly His Glu Val Gly Asp Lys Phe Asp Val Ala Val Gly Ala
```

```
                 50                  55                  60
Asn Asp Ala Tyr Gly Gln Tyr Asp Glu Asn Leu Val Gln Arg Val Pro
 65                  70                  75                  80

Lys Asp Val Phe Met Gly Val Asp Glu Leu Gln Val Gly Met Arg Phe
                     85                  90                  95

Leu Ala Glu Thr Asp Gln Gly Pro Val Pro Val Glu Ile Thr Ala Val
                100                 105                 110

Glu Asp Asp His Val Val Val Asp Gly Asn His Met Leu Ala Gly Gln
                115                 120                 125

Asn Leu Lys Phe Asn Val Glu Val Ala Ile Arg Glu Ala Thr Glu
                130                 135                 140

Glu Glu Leu Ala His Gly His Val His Gly Ala His Asp His His His
145                 150                 155                 160

Asp His Asp His Asp Gly Gly Ser Gly Gly Gly Ser Gly Gly Gly
                165                 170                 175

Ser Gly Gly Gly Ser Gly Gly Gly Ser Gly Gly Gly Glu Arg Ala Val
                180                 185                 190

His Ala Asp Met Gly Tyr Trp Ile Glu Ser Gln Lys Asn Gly Ser Trp
                195                 200                 205

Lys Leu Glu Lys Ala Ser Leu Ile Glu Val Lys Thr Ala Thr Trp Pro
210                 215                 220

Lys Ser His Thr Leu Trp Ser Asn Gly Val Leu Glu Ser Asp Met Ile
225                 230                 235                 240

Ile Pro Lys Ser Leu Ala Gly Pro Ile Ser Gln His Asn Tyr Arg Pro
                245                 250                 255

Gly Tyr His Thr Gln Thr Ala Gly Pro Trp His Leu Gly Lys Leu Glu
                260                 265                 270

Leu Asp Phe Asn Tyr Cys Glu Gly Thr Thr Val Val Ile Thr Glu Asn
                275                 280                 285

Cys Gly Thr Arg Gly Pro Ser Leu Arg Thr Thr Thr Val Ser Gly Lys
                290                 295                 300

Leu Ile His Glu Trp Cys Cys Arg Ser Cys Thr Leu Pro Pro Leu Arg
305                 310                 315                 320

Tyr Met Gly Glu Asp Gly Cys Trp Tyr Gly Met Glu Ile Arg Pro Ile
                325                 330                 335

Asn Glu Lys Glu Glu Asn Met Val Lys Ser Leu Val Ser Ala Leu Glu
                340                 345                 350

His His His His His His
            355

<210> SEQ ID NO 35
<211> LENGTH: 358
<212> TYPE: PRT
<213> ORGANISM: Artificial
<220> FEATURE:
<223> OTHER INFORMATION: Fusion protein of tandem E. coli SlyD with
      Dengue virus type 4 NS1 ?-ladder domain aa 191-352

<400> SEQUENCE: 35

Met Lys Val Ala Lys Asp Leu Val Val Ser Leu Ala Tyr Gln Val Arg
 1               5                  10                  15

Thr Glu Asp Gly Val Leu Val Asp Glu Ser Pro Val Ser Ala Pro Leu
                20                  25                  30

Asp Tyr Leu His Gly His Gly Ser Leu Ile Ser Gly Leu Glu Thr Ala
                35                  40                  45
```

-continued

```
Leu Glu Gly His Glu Val Gly Asp Lys Phe Asp Val Ala Val Gly Ala
    50              55                  60
Asn Asp Ala Tyr Gly Gln Tyr Asp Glu Asn Leu Val Gln Arg Val Pro
65              70                  75                  80
Lys Asp Val Phe Met Gly Val Asp Glu Leu Gln Val Gly Met Arg Phe
            85                  90                  95
Leu Ala Glu Thr Asp Gln Gly Pro Val Pro Val Glu Ile Thr Ala Val
                100                 105                 110
Glu Asp Asp His Val Val Val Asp Gly Asn His Met Leu Ala Gly Gln
            115                 120                 125
Asn Leu Lys Phe Asn Val Glu Val Val Ala Ile Arg Glu Ala Thr Glu
    130                 135                 140
Glu Glu Leu Ala His Gly His Val His Gly Ala His Asp His His His
145             150                 155                 160
Asp His Asp His Asp Gly Gly Ser Gly Gly Gly Ser Gly Gly Gly
            165                 170                 175
Ser Gly Gly Gly Ser Gly Gly Gly Ser Gly Gly Gly Lys Ala Val
            180                 185                 190
His Ala Asp Met Gly Tyr Trp Ile Glu Ser Ser Lys Asn Gln Thr Trp
            195                 200                 205
Gln Ile Glu Lys Ala Ser Leu Ile Glu Val Lys Thr Ala Leu Trp Pro
    210                 215                 220
Lys Thr His Thr Leu Trp Ser Asn Gly Val Leu Glu Ser Gln Met Leu
225                 230                 235                 240
Ile Pro Arg Ser Tyr Ala Gly Pro Phe Ser Gln His Asn Tyr Arg Gln
            245                 250                 255
Gly Tyr Ala Thr Gln Thr Ala Gly Pro Trp His Leu Gly Lys Leu Glu
            260                 265                 270
Ile Asp Phe Gly Glu Cys Pro Gly Thr Thr Val Thr Ile Gln Glu Asp
        275                 280                 285
Cys Asp His Arg Gly Pro Ser Leu Arg Thr Thr Thr Ala Ser Gly Lys
    290                 295                 300
Leu Val Thr Gln Trp Cys Cys Arg Ser Cys Thr Met Pro Pro Leu Arg
305                 310                 315                 320
Phe Leu Gly Glu Asp Gly Cys Trp Tyr Gly Met Glu Ile Arg Pro Leu
                325                 330                 335
Ser Glu Lys Glu Glu Asn Met Val Lys Ser Gln Val Thr Ala Leu Glu
            340                 345                 350
His His His His His His
        355
```